(12) United States Patent
Steuernagel et al.

(10) Patent No.: US 8,957,020 B2
(45) Date of Patent: *Feb. 17, 2015

(54) MNK KINASE HOMOLOGOUS PROTEINS INVOLVED IN THE REGULATION OF ENERGY HOMEOSTASIS AND ORGANELLE METABOLISM

(75) Inventors: Arnd Steuernagel, Goettingen (DE); Karsten Eulenberg, Bovenden (DE); Guenter Broenner, Goettingen (DE); Thomas Ciossek, Ravensburg (DE); Bettina Rudolph, Hannover (DE); Dorothea Rudolph, Vienna (AT); Funmi Belgore, London (GB); Stefan Jaekel, Goettingen (DE); Christoph Meyer, Goettingen (DE)

(73) Assignee: Boehringer Ingelheim International GmbH, Ingelheim Am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/245,113

(22) Filed: Sep. 26, 2011

(65) Prior Publication Data

US 2012/0045451 A1 Feb. 23, 2012

Related U.S. Application Data

(63) Continuation of application No. 12/174,301, filed on Jul. 16, 2008, now Pat. No. 8,076,098, which is a continuation of application No. 10/494,010, filed as application No. PCT/EP02/12075 on Oct. 29, 2002, now abandoned.

(30) Foreign Application Priority Data

Oct. 29, 2001 (EP) .................................. 01125812
May 17, 2002 (EP) .................................. 02011073

(51) Int. Cl.
*C12N 9/12* (2006.01)
*A61K 38/45* (2006.01)
*A61K 38/00* (2006.01)

(52) U.S. Cl.
CPC .............. *C12N 9/1205* (2013.01); *A61K 38/45* (2013.01); *Y10S 514/909* (2013.01)
USPC ............. 514/4.8; 514/909; 435/183; 435/194

(58) Field of Classification Search
CPC ................................................. G01N 2500/02
See application file for complete search history.

(56) References Cited

U.S. PATENT DOCUMENTS

| | | | |
|---|---|---|---|
| 5,658,903 A | 8/1997 | Adams et al. | |
| 5,786,356 A | 7/1998 | Bell et al. | |
| 5,932,576 A | 8/1999 | Anantanarayan et al. | |
| 5,981,533 A | 11/1999 | Traxler et al. | |
| 2003/0041341 A1* | 2/2003 | Sonenberg et al. | 800/18 |
| 2005/0196787 A1* | 9/2005 | Bhanot et al. | 435/6 |
| 2009/0163520 A1 | 6/2009 | Coulter et al. | |
| 2009/0203605 A1* | 8/2009 | Segatori et al. | 514/12 |

FOREIGN PATENT DOCUMENTS

| | | |
|---|---|---|
| EP | 0 819 129 | 1/1998 |
| JP | 601 85719 | 9/1985 |
| WO | WO 89/11295 | 11/1989 |
| WO | WO 95/06411 | 3/1995 |
| WO | WO 98/25908 A1 | 6/1998 |
| WO | WO 99/02532 A2 | 1/1999 |
| WO | WO 02/055664 | 7/2002 |
| WO | WO 02/103361 | 12/2002 |
| WO | WO 02103361 | 12/2002 |
| WO | 2006066937 | 6/2006 |

OTHER PUBLICATIONS

Tschopp et al. (2000) Phosphorylation of eIF-4E on Ser 209 in Response to Mitogenic and Inflammatory Stimuli Is Faithfully Detected by Specific Antibodies, Mol. Cell Biol. Res. Comm., vol. 3, pp. 205-211.*
Scheper et al. (2002) Phosphorylation of eukaryotic initiation factor 4E markedly reduces its affinity for capped mRNA, J. Biol .Chem., vol. 277, No. 5, pp. 3303-3309.*
La Fontaine et al. (1999) Intracellular localization and loss of copper responsiveness of Mnk, the murine homologue of the Menkes protein, in cells from blotchy (Mo blo) and brindled (Mo br) mouse mutants, Hum. Mol. Genet., vol. 8, No. 6, pp. 1069-1075.*
Scheper et al. (2003) The N and C termini of the splice variants of the human mitogen-activated protein kinase-interacting kinase Mnk2 determine activity and localization, Mol. Cell. Biol., vol. 23, No. 16, pp. 5692-5705.*
Cherkasov et al. (2004) Structural characterization of genomes by large scale sequence-structure threading: application of reliability analysis in structural genomics, BMC Bioinform., 5 (61), 1-11.*
Fukunaga R et al.: Mnk1, a new map kinase-activated protein kinase, isolated by a novel expression screening method for identifying protein kinase substrates, Embo Journal, Oxford University Press, Surrey, GB, vol. 16, No. 8, 1997, pp. 1921-1933, XP000887346.

(Continued)

*Primary Examiner* — Manjunath Rao
*Assistant Examiner* — Samuel Liu
(74) *Attorney, Agent, or Firm* — Thomas Horstemeyer, LLP

(57) ABSTRACT

This invention relates to the use of nucleic acid sequences of the MAP kinase-interacting kinase (Mnk) gene family and amino acid sequences encoded thereby, and to using these sequences or effectors of Mnk nucleic acids or polypeptides, particularly Mnk kinase inhibitors and activators, in the diagnosis and treatment of diseases and disorders related to bodyweight regulation and thermogenesis. One aspect of the disclosure encompasses methods of identifying an animal or human having an elevated probability of having or developing obesity, the method comprising: (a) obtaining a biological sample from an animal or human subject; and (b) determining from the biological sample whether the animal or human subject has a genetic variant of an Mnk2 and/or Mnk1 gene or a homolog thereof, or an expression product of said Mnk2 and/or Mnk1 gene or homolog thereof, wherein said genetic variant is associated with an elevated probability of having or developing obesity.

3 Claims, 33 Drawing Sheets

(56) References Cited

OTHER PUBLICATIONS

Slentz-Kesler K et al.: Identification of the human Mnk2 gene (MKNK2) through protein interaction with estrogen receptor beta, Genomics, Academic Press, San Diego, US, vol. 69, No. 1, Oct. 1, 2000, pp. 63-71, XP002221149.

Database CA Online Chemical Abstracts Service, Columbus, Ohio, US; Li Nenggan et al.: Protein and cDNA sequence of a novel human protein kinase Mnk2, retrieved from STN Database accession No. 136: 19531 8 HCA, XP002246761 & CN 1 301 870 (Nanfang Research Center, State Human Genome Project, Peop. Rep. China) Jul. 4, 2001.

Database Biosis Online Biosciences Information Service, I Philadelphia, PA, US, Apr. 2000, Tschopp et al.: Phosphorylation of eIF-4E on Ser 209 in response to mitogenic and inflammatory stimuli is faithfully detected by specific antibodies, Database accession No. PREV200000389084, XP002246762 cited in the application abstract & Molecular Cell Biology Research Communications, vol. 3, No. 4, Apr. 2000, pp. 205-21 1.

Eatabase Biosis Online Biosciences Information Service, Philadelphia, PA, US, Aug. 2001, Knauf Ursula et al.: Negative regulation of protein translation by mitogen-activated protein kinaseinteracting kinases I and 2, Database accession No. PREV200100384691, XP002246763 cited in the application abstract & Molecular Cellular Biology, vol. 21, No. 16, Apr. 2001, pp. 5500-551 1.

Waskiewicz, A.J. et al. Phosphorylation of the cap-binding protein eukaryotic translation initiation factor 4E by protein kinase Mnk1 in vivo, Mol. Cell. Biol., 1999, vol. 19, pp. 1871-1880.

Wikipedia "Aptamer" Wikipedia "Aptamer".

Tsukiyama-Kohara et al.: Mature Medicine, Oct. 1, 2001 vol. 7, No. 10, pp.1 28-1 132.

Scheper, Gert C et al.: The mitogen-activated protein kinase signal-integrating kinase Mnk2 is / eukaryotic initiation factor 4E Kinase with high levels of basal activity in mammalian cells, Mol. Cell. Biol. Feb. 2001, vol. 21, No. 3, p. 743-754.

Jauch et al.: Crystal structures of the Mnk2 kinase domain reveal an inhibitory conformation and a zinc binding site, Structure, vol. 13, / 1559-1568, Oct. 2005.

Kordik et al.: Pyrazolecarboxamide human neuropeptide Y5 receptor ligands with in vivo antifeedant activity, Bioorganic & Medicinal Chemistry Letters 11 (2001) 2287-2290.

Tocris bioscience.

Extract of the "Lexikon der Biochemie", SpeMrum Akademischer Verlag Heidelberg, 1999.

Waskiewicz, et al. "Mitogen-activated protein kinases activate the serine/theronine kinases Mnk1 and Mnk2", The EMBO Journal vol. 16, No. 8, pp. 1909-1920, 1997.

Ebbert, J.O. & Jensen, M.D. Fat Depots, Free Fatty Acids, and Dyslipidemia. Nutrients, 2013, vol. 5, pp. 498-508.

Heilbronn, L. et al. Failure of fat cell proliferation, mitochondrial function and fat oxidation results in ectopic fat storage, insulin resistance and type II diabetes mellitus. Int. J. Obesity, 2004, vol. 28, pp. S12-S21.

Bucci M., et al. Human obesity is characterized by defective fat storage and enhanced muscle fatty acid oxidation, and trimetazidine gradually counteracts these abnormalities. Am J Physiol Endocrinol Metab., 2011, vol. 301, pp. E105-E112.

Savage, D.B. et al. Disordered Lipid Metabolism and the Pathogenesis of Insulin Resistance. Physiol Rev 2007, vol. 87, pp. 507-520.

\* cited by examiner

```
hsXP_030637   MVQKKPAELQGFHRSFKGQNP--------------------FELAFSLDQPDHGDSD
(SEQ ID NO.: 2)
hsXP_001600   MVSSQ-------------------------------------------KLEKP-----
(SEQ ID NO.: 6)
dmAAB18789    MVEPKSGTAASAAAAKASNNNNNNHPRGSGDSGIRSGSGISCSNTDNSCSQSQSDGQNEL
(SEQ ID NO.: 40)  *. :                                              . .:.

hsXP_030637   FGLQCSARPDMPASQPIDIPDAKKR---------GKKKKRGRATDSFSG-RFEDVYQLQ
hsXP_001600   --------IEMGSSEPLPIADGDRR---------RKKKRRGRATDSLPG-KFEDMYKLT
dmAAB18789    TRYSSEDVSGNESSEAPNMTEVERQAELNRHKEEMQKKRRKKRISSSLHSSTFQELYKLT
                   :*:.  :.:  .::             **::: * :.*: .  *::*:* hsXP_030637   EDVLGEGAHARVQTCINLITSQEYAVKIIEKQPGHIRSRVFREVEMLYQCQGHRNVLELI
hsXP_001600   SELLGEGAYAKVQGAVSLQNGKEYAVKIIEKQAGHSRSRVFREVETLYQCQGNKNILELI
dmAAB18789    GEILGEGAYASVQTCVNIYTDLEYAVKVIDKIPGHARARVFREVETFHHCQGHLGILQLI
              ::*****:*    .:.:   .. ***:*. :****:  :::*: .:*:*** hsXP_030637   EFFEEEDRFYLVFEKMRGGSILSHIHKRRHFNELEASVVVQDVASALDFLHNKGIAHRDL
hsXP_001600   EFFEDDTRFYLVFEKLQGGSILAHIQKQKHFNEREASRVVRDVAAALDFLHTKGIAHRDL
dmAAB18789    EFFEDDKKFYLVFEKINGGPLLSRIQEHICFSEHEPSQIIKEIASGLDFLHKKGIAHRDL
              *::.:***:..:**.:*:::*   *.* *.*  ::::*:.*.****** hsXP_030637   KPENILCEHPNQVSPVKICDFDLGSGIKLNGDCS-PISTPELLTPCGSAEYMAPEVVEAF
hsXP_001600   KPENILCESPEKVSPVKICDFDLGSGMKLNNSCT-PITTPELTTPCGSAEYMAPEVVEVF
dmAAB18789    KPENILCVKTDSLCPIKICDFDLGSGIKFTTDISSPAATPQLLTPVGSAEFMAPEVVDLF
              ******   .:.:.*:**********:*:.. :*  . :  : :  :****: * hsXP_030637   SEEASIYDKRCDLWSLGVILYILLSGYPPFVGRCGSDCGWDRGEACPACQNMLFESIQEG
hsXP_001600   TDQATFYDKRCDLWSLGVVLYIMLSGYPPFVGHCGADCGWDRGEVCRVCQNKLFESIQEG
dmAAB18789    VGEAHYYDKRCDLWSLGVIAYILLCGYPPFSGNCGEDCGWNRGENCRTCQELLFESIQEG
              .:*  ************: **:*.****** * ** ****:*** *  :**: ********:

hsXP_030637   KYEFPDKDWAHISCAAKDLISKLLVRDAKQRLSAAQVLQHPWVQGCAPE---------N
hsXP_001600   KYEFPDKDWAHISSEAKDLISKLLVRDAKQRLSAAQVLQHPWVQGQAPE---------K
dmAAB18789    HFSFPEAEWHDVSDEAKDLISNLLVKKASNRLSAEAVLNHPWIRMCEQEPPASKHGRRHK
              : .**::*  .:*  ******:***: *.:****  **.***::  *           :

hsXP_030637   TLPTPMVLQRN-SCAKDLTSFAAEAIAMNRQLAQH-----------------------
hsXP_001600   GLPTPQVLQRN-SSTMDLTLFAAEAIALNRQLSQH-----------------------
dmAAB18789    ALQTPSNIRRNHQSAREISQFAESAMAVKRVVLQHFSMRYDYMKERPNIYQPSQAYMDAY
               * **  :::**   ::**  ***:* :*: **  .*:*::* : **

hsXP_030637   -DEDLAEEEA------AGQGQPVLVRATSRCLQLSPPSQSKLAQRRQRASLSSAPVVLVG
hsXP_001600   -EENELAEEP------EALADGLCS------MKLSPPCKSRLARRRALAQAGRGEDRSPP
dmAAB18789    SDENYNPKPPGHYTRNRSQRNPASSLCGYG-GRMSSMHGQRANSRRSSRNASRNASAIYP
               :*:  :.       . :        .  :  ::*.    .: **     . .

hsXP_030637   DHA--------------------------------------------------------
hsXP_001600   TAL--------------------------------------------------------
dmAAB18789    NSGGFKTLNVHEEDDDDEGLEAFGHIDDDDEWSRSRREYQQQCETLGEDRFRRQSGSEGD
```

*Fig. 3A*

```
hsXP_030637    ------------------------------------------------------------
hsXP_001600    ------------------------------------------------------------
dmAAB18789     EVEDDEDGENEDYQHYKHYWRELDEEEGDDYLYEQQQRVDDKFGEEEFEDEPKEETQADN hsXP_030637    ------------------------------------------------------------
hsXP_001600    ------------------------------------------------------------
dmAAB18789     LKLSKAYVEQVGETNVEKSKPQDDNGGYIREDLIMDNMDMKKNTQQSEFAKLTIMRNDAQ hsXP_030637    ------------------------------------------------------------
hsXP_001600    ------------------------------------------------------------
dmAAB18789     TEENKIMQQQDEEKKEDKQQDDVDGAKKQGPSSDISATTITDNNKLQTPVMTTTHINNWQ hsXP_030637    ------------------------------------------------------------
hsXP_001600    ------------------------------------------------------------
dmAAB18789     TGDAIEDDDVKLLDSISDLNEKLPEIYETANIVVNSAAVPAASTPAASATRPPTDNPEED hsXP_030637    ------------------------------------------------------------
hsXP_001600    ------------------------------------------------------------
dmAAB18789     DSNVTKPTTTAEGTTMQTTFGMSAEEEKPVALSHTAGHHSKTGRTVNFAPDAYQNDEDAD hsXP_030637    ------------------------------------------------------------
hsXP_001600    ------------------------------------------------------------
dmAAB18789     IDEDDDYDDEENLHEHSKQQLPSNAYTRKQRQQHQRYIVPRYQLADQVPQRQHTENWRYR hsXP_030637    ------------------------------------------------------------
hsXP_001600    ------------------------------------------------------------
dmAAB18789     THHSQEQQPTADYRKYRPPFSTGGGGGHHGNLQRNYLGSFSHSGGAAGYKIAPMPPPMQP hsXP_030637    ------------------------------------------------------------
hsXP_001600    ------------------------------------------------------------
dmAAB18789     PPRHNSAGSSGSGSGSGGSPPSDEQSAIRNWRQDCVYARSCGMNQGPEQQRHNRSSGQRV hsXP_030637    ------------------------------------------------------------
hsXP_001600    ------------------------------------------------------------
dmAAB18789     QQQPRIGSGRFAHLQAAQLMDELPDMRIGLSPPSESVLLQRRLRQQQRANDLSEVLRAGH hsXP_030637    -----------
hsXP_001600    -----------
dmAAB18789     RQWLRGSTVDR
```

Fig. 3A-Contd

```
XM_030637.3   MVQKKPAELQGFHRSFKGQNPFELAPSLDQPDHGDSDFGLQCSARFDMPASQPIDIPDAK
AF237775      MVQKKPAELQGFHRSFKGQNPFELAPSLDQPDHGDSDFGLQCSARFDMPASQPIDIPDAK
NM_017572.1   MVQKKPAELQGFHRSFKGQNPFELAPSLDQPDHGDSDFGLQCSARFDMPASQPIDIPDAK
              ************************************************************

XM_030637.3   KRGKKKKRGRATDSFSGRFEDVYQLQEDVLGEGAHARVQTCINLITSQEYAVKIIEKQPG
AF237775      KRGKKKKRGRATDSFSGRFEDVYQLQEDVLGEGAHARVQTCINLITSQEYAVKIIEKQPG
NM_017572.1   KRGKKKKRGRATDSFSGRFEDVYQLQEDVLGEGAHARVQTCINLITSQEYAVKIIEKQPG
              ************************************************************

XM_030637.3   HIRSEVFREVEMLYQCQGHRNVLELIEFFEEEDRFYLVFEKMRGGSILSHIHKRRHFNEL
AF237775      HIRSEVFREVEMLYQCQGHRNVLELIEFFEEEDRFYLVFEKMRGGSILSHIHKRRHFNEL
NM_017572.1   HIRSEVFREVEMLYQCQGHRNVLELIEFFEEEDRFYLVFEKMRGGSILSHIHKRRHFNEL
              ************************************************************

XM_030637.3   EASVVQDVASALDFLHNKGIAHRDLKPENILCEHPNQVSPVKICDFDLGSGIKLNGDCS
AF237775      EASVVQDVASALDFLHNKGIAHRDLKPENILCEHPNQVSPVKICDFDLGSGIKLNGDCS
NM_017572.1   EASVVQDVASALDFLHNKGIAHRDLKPENILCEHPNQVSPVKICDFDLGSGIKLNGDCS
              ************************************************************

XM_030637.3   PISTPELLTPCGSAEYMAPEVVEAFSEEASIYDKRCDLWSLGVILYILLSGYPPFVGRCG
AF237775      PISTPELLTPCGSAEYMAPEVVEAFSEEASIYDKRCDLWSLGVILYILLSGYPPFVGRCG
NM_017572.1   PISTPELLTPCGSAEYMAPELVEAFSEEASIYDKRCDLWSLGVILYILLSGYPPFVGRCG
              ********************,***************************************

XM_030637.3   SDCGWDRGEACPACQNMLFESIQEGKYEFPDKDWAHISCAAKDLISKLLVRDAKQRLSAA
AF237775      SDCGWDRGEACPACQNMLFESIQEGKYEFPDKDWAHISCAAKDLISKLLVRDAKQRLSAA
NM_017572.1   SDCGWDRGEACPACQNMLFESIQEGKYEFPDKDWAHISCAAKDLISKLLVRDAKQRLSAA
              ************************************************************

XM_030637.3   QVLQHPWVQGCAPENTLFTPMVLQRNSCAKDLTSFAAEAIAMNRQLAQHDEDLAEEEAAG
AF237775      QVLQHPWVQGCAPENTLFTPMVLQRNSCAKDLTSFAAEAIAMNRQLAQHDEDLAEEEAAG
NM_017572.1   QVLQHPWVQGCAPENTLFTPMVLQR-----------------------------------
              *************************,..... .. .... . .. ... ......

XM_030637.3   QGQFVLVRATSRCLQLSPPSQSKLAQRRQRASLSSAPVVLVGDEA
AF237775      QGQFVLVRATSRCLQLSPPSQSKLAQRRQRASLSSAPVVLVGDEA
NM_017572.1   ----------WDSHFLLPPHPCRIBVRPG-----GLVETVYVNE---
              ....    :: .  * **  ..  *   ::  ..,* *.: :
```

Fig. 3B

```
XM_001600.2   MVSSQKLEKPIEMGSSEPLPIADGDRRRKKKRRGRATDSLPGKFEDMYKLTSELLGEGAY
NM_003684.2   MVSSQKLEKPIEMGSSEPLPIADGDRRRKKKRRGRATDSLPGKFEDMYKLTSELLGEGAY
AB000409.1    MVSSQKLEKPIEMGSSEPLPIADGDRRRKKKRRGRATDSLPGKFEDMYKLTSELLGEGAY
              ************************************************************

XM_001600.2   AKVQGAVSLQNGKEYAVKIIEKQAGHSRSRVFREVETLYQCQGNKNILELIEFFEDDTRF
NM_003684.2   AKVQGAVSLQNGKEYAVKIIEKQAGHSRSRVFREVETLYQCQGNKNILELIEFFEDDTRF
AB000409.1    AKVQGAVSLQNGKEYAVKIIEKQAGHSRSRVFREVETLYQCQGNKNILELIEFFEDDTRF
              ************************************************************

XM_001600.2   YLVFEKLQGGSILAHIQKQKHFNEREASRVVRDVAAALDFLHTK----------------
NM_003684.2   YLVFEKLQGGSILAHIQKQKHFNEREASRVVRDVAAALDFLHTEDKVSLCHLGWSAMAPS
AB000409.1    YLVFEKLQGGSILAHIQKQKHFNEREASRVVRDVAAALDFLHTK----------------
              *******************************************

XM_001600.2   ------------------------------GIAHRDLKPENILCESPEKVSPVKICDFDLGSGMK
NM_003684.2   GLTAAPTSLGSSDPPTSASQVAGTTGIAHRDLKPENILCESPEKVSPVKICDFDLGSGMK
AB000409.1    ------------------------------GIAHRDLKPENILCESPEKVSPVKICDFDLGSGMK
                                            *******************************

XM_001600.2   LNNSCTPITTPELTTPCGSAEYMAPEVVEVFTDQATFYDKRCDLWSLGVVLYIMLSGYPP
NM_003684.2   LNNSCTPITTPELTTPCGSAEYMAPEVVEVFTDQATFYDKRCDLWSLGVVLYIMLSGYPP
AB000409.1    LNNSCTPITTPELTTPCGSAEYMAPEVVEVFTDQATFYDKRCDLWSLGVVLYIMLSGYPP
              ************************************************************

XM_001600.2   FVGHCGADCGWDRGEVCRVCQNKLFESIQEGKYEFPDKDWAHISSEAKDLISKLLVRDAK
NM_003684.2   FVGHCGADCGWDRGEVCRVCQNKLFESIQEGKYEFPDKDWAHISSEAKDLISKLLVRDAK
AB000409.1    FVGHCGADCGWDRGEVCRVCQNKLFESIQEGKYEFPDKDWAHISSEAKDLISKLLVRDAK
              ************************************************************

XM_001600.2   QRLSAAQVLQHPWVQGQAPEKGLPTPQVLQRNSSTMDLTLFAAEAIALNRQLSQHEENEL
NM_003684.2   QRLSAAQVLQHPWVQGQAPEKGLPTPQVLQRNSSTMDLTLFAAEAIALNRQLSQHEENEL
AB000409.1    QRLSAAQVLQHPWVQGQAPEKGLPTPQVLQRNSSTMDLTLFAAEAIALNRQLSQHEENEL
              ************************************************************

XM_001600.2   AEEPEALADXLCSMKLSPPCKSRLARRRALAQAGRGEDRSPPTAL
NM_003684.2   AEEPEALADXLCSMKLSPPCKSRLARRRALAQAGRGEDRSPPTAL
AB000409.1    AEEPEALADXLCSMKLSPPCKSRLARRRALAQAGRGEDRSPPTAL
              *********************************************
```

*Fig. 3C*

SEQ ID NO.: 1

1 cggtcccctc ccccgctggc ggggcccgga cagaagatgg tgcagaagaa accagccgaa
61 cttcagggtt tccaccgttc gttcaagggg cagaacccct tcgagctggc cttctcccta
121 gaccagcccg accacggaga ctctgacttt ggcctgcagt gctcagcccg ccctgacatg
181 cccgccagcc agcccattga catcccggac gccaagaaga ggggcaagaa gaagaagcgc
241 ggccggggcca ccgacagctt ctcgggcagg tttgaagacg tctaccagct gcaggaagat
301 gtgctggggg agggcgctca tgcccgagtg cagacctgca tcaacctgat caccagccag
361 gagtacgccg tcaagatcat tgagaagcag ccaggccaca ttcggagcag ggttttcagg
421 gaggtggaga tgctgtacca gtgccaggga cacaggaacg tcctagagct gattgagttc
481 ttcgaggagg aggaccgctt ctacctggtg tttgagaaga tgcggggagg ctccatcctg
541 agccacatcc acaagcgccg gcacttcaac gagctggagg ccagcgtggt ggtgcaggac
601 gtggccagcg ccttggactt tctgcataac aaaggcatcg cccacaggga cctaaagccg
661 gaaaacatcc tctgtgagca ccccaaccag gtctcccccg tgaagatctg tgacttcgac
721 ctgggcagcg gcatcaaact caacggggac tgctcccccta tctccacccc ggagctgctc
781 actccgtgcg gctcggcgga gtacatggcc ccggaggtag tggaggcctt cagcgaggag
841 gctagcatct acgacaagcg ctgcgacctg tggagcctgg gcgtcatctt gtatatccta
901 ctcagcggct acccgccctt cgtgggccgc tgtggcagcg actgcggctg ggaccgcggc
961 gaggcctgcc ctgcctgcca gaacatgctg tttgagagca tccaggaggg caagtacgag
1021 ttccccgaca aggactgggc ccacatctcc tgcgctgcca agacctcat ctccaagctg
1081 ctggtccgtg acgccaagca gaggctgagt gccgcccaag tcctgcagca ccctgggtt
1141 caggggtgcg ccccggagaa caccttgccc actcccatgg tcctgcagag gaacagctgt
1201 gccaaagacc tcacgtcctt cgcggctgag gccattgcca tgaaccggca gctggcccag
1261 cacgacgagg acctggctga ggaggaggcc gcggggcagg gccagcccgt cctggtccga
1321 gctacctcac gctgcctgca gctgtctcca ccctcccagt ccaagctggc gcagcggcgg
1381 caaagggcca gtctgtcctc ggccccagtg gtcctggtgg gagaccacgc ctgaccctcc
1441 catc

*Fig. 3D*

SEQ ID NO.: 2

MVQKKPAELQGFHRSFKGQNPFELAFSLDQPDHGDSDFGLQCSA

RPDMPASQPIDIPDAKKRGKKKKRGRATDSFSGRFEDVYQLQEDVLGEGAHARVQTCI

NLITSQEYAVKIIEKQPGHIRSRVFREVEMLYQCQGHRNVLELIEFFEEEDRFYLVFE

KMRGGSILSHIHKRRHFNELEASVVVQDVASALDFLHNKGIAHRDLKPENILCEHPNQ

VSPVKICDFDLGSGIKLNGDCSPISTPELLTPCGSAEYMAPEVVEAFSEEASIYDKRC

DLWSLGVILYILLSGYPPFVGRCGSDCGWDRGEACPACQNMLFESIQEGKYEFPDKDW

AHISCAAKDLISKLLVRDAKQRLSAAQVLQHPWVQGCAPENTLPTPMVLQRNSCAKDL

TSFAAEAIAMNRQLAQHDEDLAEEEAAGQGQPVLVRATSRCLQLSPPSQSKLAQRRQR
ASLSSAPVVLVGDHA

*Fig. 3E*

SEQ ID NO.: 3

```
gctggcgggg cccggacaga agatggtgca gaagaaacca gccgaacttc agggtttcca
   61 ccgttcgttc aaggggcaga accccttcga gctggccttc tccctagacc agcccgacca
  121 cggagactct gactttggcc tgcagtgctc agcccgccct gacatgcccg ccagccagcc
  181 cattgacatc ccggacgcca agaagagggg caagaagaag aagcgcggcc gggccaccga
  241 cagcttctcg ggcaggtttg aagacgtcta ccagctgcag gaagatgtgc tggggagg
  301 cgctcatgcc cgagtgcaga cctgcatcaa cctgatcacc agccaggagt acgccgtcaa
  361 gatcattgag aagcagccag gccacattcg gagcagggtt tcagggagg tggagatgct
  421 gtaccagtgc cagggacaca ggaacgtcct agagctgatt gagttcttcg aggaggagga
  481 ccgcttctac ctggtgtttg agaagatgcg gggaggctcc atcctgagcc acatccacaa
  541 gcgccggcac ttcaacgagc tggaggccag cgtggtggtg caggacgtgg ccagcgcctt
  601 ggactttctg cataacaaag gcatcgccca cagggaccta aagccggaaa acatcctctg
  661 tgagcacccc aaccaggtct cccccgtgaa gatctgtgac ttcgacctgg gcagcggcat
  721 caaactcaac ggggactgct ccccatctc caccccggag ctgctcactc cgtgcggctc
  781 ggcggagtac atggccccgg agttagtgga ggccttcagc gaggaggcta gcatctacga
  841 caagcgctgc gacctgtgga gctgggcgt catcttgtat atcctactca gcggctaccc
  901 gcccttcgtg ggccgctgtg gcagcgactg cggctgggac cgcggcgagg cctgccctgc
  961 ctgccagaac atgctgtttg agagcatcca ggagggcaag tacgagttcc ccgacaagga
 1021 ctgggcccac atctcctgcg ctgccaaaga cctcatctcc aagctgctgg tccgtgacgc
 1081 caagcagagg ctgagtgccg cccaagtcct gcaacacccc tgggttcagg ggtgcgcccc
 1141 ggagaacacc ttgcccactc ccatggtcct gcagaggtgg gacagtcact tcctcctccc
 1201 tccccacccc tgtcgcatcc acgtgcgacc tggaggactg gtcagaaccg ttactgtgaa
 1261 tgagtgaaga tcctggagga ccctggcccc aggccagctc ccatcgctgg gggacggtga
 1321 acggccatgt gttaatgtta cgatgttttt aaaagacaaa aaaaaaaaa aaacctcaaa
 1381 agttttttta aagtggggga aaaacatcca agcactttaa ttccaatgta ccaggtgaac
 1441 tgacggagct cagaagtttt cctttacacc aactgtcaat gccggaattt tgtattctgt
 1501 tttgtaaaga tttaataaaa gtcaaaaaac ttgcaaaaaa aaaaaaaa
```

*Fig. 3F*

SEQ ID NO.: 4

MVQKKPAELQGFHRSFKGQNPFELAFSLDQPDHGDSDFGLQCSA

RPDMPASQPIDIPDAKKRGKKKKRGRATDSFSGRFEDVYQLQEDVLGEGAHARVQTCI

NLITSQEYAVKIIEKQPGHIRSRVFREVEMLYQCQGHRNVLELIEFFEEEDRFYLVFE

KMRGGSILSHIHKRRHFNELEASVVVQDVASALDFLHNKGIAHRDLKPENILCEHPNQ

VSPVKICDFDLGSGIKLNGDCSPISTPELLTPCGSAEYMAPEVVEAFSEEASIYDKRC

DLWSLGVILYILLSGYPPFVGRCGSDCGWDRGEACPACQNMLFESIQEGKYEFPDKDW

AHISCAAKDLISKLLVRDAKQRLSAAQVLQHPWVQGCAPENTLPTPMVLQRWDSHFLL
PPHPCRIHVRPGGLVRTVTVNE

*Fig. 3G*

SEQ ID NO.: 5

```
   1 ggcacgaggg cgaccgctcc ccggcgggag ccagcgaagg tttccatgtc agaggccgat
  61 ggagaactga agattgccac ctacgcacaa aggccattga gacacttcgt gtagctggaa
 121 gacaccaact tcctgacagg agctttattt catttgggat ttcaagttta cagatggtat
 181 cttctcaaaa gttggaaaaa cctatagaga tgggcagtag cgaaccccct cccatcgcag
 241 atggtgacag gaggaggaag aagaagcgga gggggccgggc cactgactcc ttgccaggaa
 301 agtttgaaga tatgtacaag ctgacctctg aattgcttgg agagggagcc tatgccaaag
 361 ttcaaggtgc cgtgagccta cagaatggca aagagtatgc cgtcaaaatc atcgagaaac
 421 aagcagggca cagtcggagt agggtgtttc gagaggtgga gacgctgtat cagtgtcagg
 481 gaaacaagaa catttggag ctgattgagt tctttgaaga tgacacaagg ttttacttgg
 541 tctttgagaa attgcaagga ggttccatct tagcccacat ccagaagcaa aagcacttca
 601 atgagcgaga agccagccga gtggtgcggg acgttgctgc tgcccttgac ttcctgcata
 661 ccaaagacaa agtctctctc tgtcacctag gctggagtgc tatggcgcca tcagggctca
 721 ctgcagcccc aacctccctg ggctccagtg atcctcccac ctcagcctcc caagtagctg
 781 ggactacagg cattgctcat cgtgatctga aaccagaaaa tatattgtgt gaatctccag
 841 aaaaggtgtc tccagtgaaa atctgtgact ttgacttggg cagtgggatg aaactgaaca
 901 actcctgtac ccccataacc acaccagagc tgaccacccc atgtggctct gcagaataca
 961 tggcccctga ggtagtggag gtcttcacgg accaggccac attctacgac aagcgctgtg
1021 acctgtggag cctgggcgtg gtcctctaca tcatgctgag tggctaccca cccttcgtgg
1081 gtcactgcgg ggccgactgt ggctgggacc ggggcgaggt ctgcagggtg tgccagaaca
1141 agctgtttga aagcatccag gaaggcaagt atgagtttcc tgacaaggac tgggcacaca
1201 tctccagtga agccaaagac ctcatctcca agctcctggt gcgagatgca aagcagagac
1261 ttagcgccgc ccaagttctg cagcacccat gggtgcaggg gcaagctcca gaaaagggac
1321 tccccacgcc gcaagtcctc cagaggaaca gcagcacaat ggacctgacg ctcttcgcag
1381 ctgaggccat cgcccttaac cgccagctat ctcagcacga agagaacgaa ctagcagagg
1441 agccagaggc actagctgat ggcctctgct ccatgaagct ttccctccc tgcaagtcac
1501 gcctggcccg gagacgggcc ctggcccagg caggccgtgg tgaagacagg agcccgccca
1561 cagcactctg aaatgctcca gtcacaccctt ataggcccta ggcctggcca ggcattgtcc
1621 cctggaaacc tgtgtggcta aagtctgctg agcaggcagc agcctctgct ctgtggctcc
1681 attcaggctt tttcatctac gaaggccctg aggttcccat caaccccat ttccctaggg
1741 tcctggagga aaaagctttt tccaaagggg ttgtctttga aaaggaaagc aatcactttct
1801 cactttgcat aattgcctgc agcaggaaca tctcttcact gggctccacc tgctcacccg
1861 cctgcagatc tgggatccag cctgctctca ccgctgtagc tgtggcggct ggggctgcag
1921 cctgcaggga gaagcaagaa gcatcagttg acagaggctg ccgacacgtg cctcttccct
1981 ctcttctctg tcaccctcct ctggcggtcc ttccaccttc ctctgtcctc cggatgtcct
2041 ctttgcccgt cttctccctt ggctgagcaa agccatcccc tcaattcagg gaagggcaag
2101 gagccttcct cattcaggaa atcaaatcag tcttccggtc tgcagcacgg aaaagcacat
2161 aatcttttctt tgctgtgact gaaatgtatc cctcgtttat catcccctt gtttgtgatt
2221 gctgctaaag tcagtagtat cgttttttta aaaaaaaagt ttggtgtttt taaccatgct
2281 gttccagcaa agatgatacc ttaaactccc actgcaagcc catgaacttc ccagagagtg
2341 gaacggcttg ctcttcttc tagaatgtcc atgcacttgg gttttaatca gcagttccct
2401 attattctga ttttaagctg ttcctgtgat gaacttagag acagcatcgg tgtctgctgc
2461 tgtgtcccca ggtcttgtgt gggtggcaca gatctgggca gttagatagt gctctgtgcc
2521 taaggtgaag ccacactagg gtgaagcctc acttccctgt ttgagcaatg cagtgcctgc
2581 tgcccgtgtg catgaaggta cagccattca gataagtgga actattgagt tacataaaga
2641 aaatagattt gcatttgtca ggcagacgtt tatacaacac cacggtgctt ttatacattg
2701 tgcttatttt aataaaactg aaattctaaa aaaaaaaaaa aaaaa
```

*Fig. 3H*

SEQ ID NO.: 6

MVSSQKLEKPIEMGSSEPLPIADGDRRRKKKRRGRATDSLPGKF

EDMYKLTSELLGEGAYAKVQGAVSLQNGKEYAVKIIEKQAGHSRSRVFREVETLYQCQ

GNKNILELIEFFEDDTRFYLVFEKLQGGSILAHIQKQKHFNEREASRVVRDVAAALDF

LHTKDKVSLCHLGWSAMAPSGLTAAPTSLGSSDPPTSASQVAGTTGIAHRDLKPENIL

CESPEKVSPVKICDFDLGSGMKLNNSCTPITTPELTTPCGSAEYMAPEVVEVFTDQAT

FYDKRCDLWSLGVVLYIMLSGYPPFVGHCGADCGWDRGEVCRVCQNKLFESIQEGKYE

FPDKDWAHISSEAKDLISKLLVRDAKQRLSAAQVLQHPWVQGQAPEKGLPTPQVLQRN

SSTMDLTLFAAEAIALNRQLSQHEENELAEEPEALADGLCSMKLSPPCKSRLARRRAL
AQAGRGEDRSPPTAL

*Fig. 3l*

SEQ ID NO.: 7

CGAGNAAGTGTTACTATCTAAACACATTTCAAACAATTCTTAACAAACAATTCCAAACATACAATTCCACTTACCACTTA
CCGACCAAATTACGAGTTTACAATGGACAAAGCTGAACGCGACTACTGGCATCTTCGATCCTTGGAAATCGAAGAGGAGC
CGCGATTTCCGCCAACAAACGTCGCTGATCCACTAACCGCACGCAATCTGTTCCAGCTCTACGTCAACACCTTCATTGGA
GCCAATCTGGCCGAGTCGTGTGTTTTCCCATTGGACGTGGCCAAGACCCGGATGCAGGTAGATGGCGAGCAGGCCAAGAA
GACGGGTAAAGCGATGCCAACTTTCCGTGCAACTCTTACCAACATGATCCGAGTGGAGGGATTCAAGTCGCTCTACGCCG
GCTTCTCGGCAATGGTGACCCGAAACTTTATCTTCAACTCGTTACGTGTTGTTCTCTACGACGTTTTCCGGCqCCCTTTT
CTCTACCAqAACGAACGGAACGAGGAAGTGCTCAAGATCTACATGGCGCTGGGATGCAGCTTCACCGCAGGCTGCATTGC
CCAqGCACTGqCCAATCCcTTTGACATCGTCAAGGTGCqAATGCAGAcGGAAGqaCqCCqCCGCCAGcTGGqcTATGATG
TGCGGGTqAACAGCATGGTGCAGGCcTTcGTGqACATCTACCGCcGTGGCGGAcTGCCCAGTATGTGqAAGGGTGTAGGq
CCCAGCTGCATGCGTGCCTGCCTqATGACGACCGGCGATGTGGqCAGTTACqATATCAGTAAGCGCACCTTCAAGCGCcT
GcTGGACTTGGAGGAAGGCCTGCCACTGcGTTTcGTGTcTTCCATGtGCGCCGGACTAACGGCATCCGTGCTCAGCACGC
CGGCGaACGTGaTCAAGTCGCGGATGATGAaCCAGCCGGTGaACGAGAGCGGCAAGAATCTGTACTACAAGAACTCCCTC
GacTGCATTAGGAAGCTGGTCAGGGAGGAGGGTGTCCTCACGTTGTATAAGGGCCTCATGCCCAcTTGGTTTCGCCTGGG
ACCGTTCTCAGTGCTCTTTTGGCTGTCCGTCGAGCAGCTGCGTCAGTGGAaAAGGCCAGAGTGGATTTTAGGAGCAAACTA
TCAATCTTACTATCGTATTTTGTATGTCTTTTAACACGCAATAAAAAGGGTGCAAGTCAAACCATCTATTATACATATTA
TAAATATAaCTTTAATCCCAAAAAAAAAAAAAAAAAACTCGTGCCGAATTCGAT

*Fig. 7A*

SEQ ID NO.: 8

MDKAERDYWHLRSLEIEEEPRFPPTNVADPLTARNLFQLYVNTFIGANLAESCVFPLDVAKTRMQVDGEQAKKTGKAMPT
FRATLTNMIRVEGFKSLYAGFSAMVTRNFIFNSLRVVLYDVFRRPFLYQNERNEEVLKIYMALGCSFTAGCIAQALANPF
DIVKVRMQTEGRRRQLGYDVRVNSMVQAFVDIYRRGGLPSMWKGVGPSCMRACLMTTGDVGSYDISKRTFKRLLDLEEGL
PLRFVSSMCAGLTASVLSTPANVIKSRMMNQPVNESGKNLYYKNSLDCIRKLVREEGVLTLYKGLMPTWFRLGPFSVLFW
LSVEQLRQWKGQSGF

*Fig. 7B*

| Exon | Exon position in cDNA (bp) | Intron length (bp) | 5' Intron-Exon Junction | 3' Exon-Intron Junction |
|---|---|---|---|---|
| 1 | 1-48 | 92 | SEQ ID No.:60<br>ccttagacctgGCCCAGCACAGG | SEQ ID No.: 61<br>GAAGCCCGACCTgtgagccccca |
| 2 | 49-151 | 80 | SEQ ID No.:62<br>ctctctctacaGACATGCCTTCC | SEQ ID No.: 63<br>GCAGGTTCGAAGgtgagctgcaga |
| 3 | 152-249 | >1kb, max. 1.3 | SEQ ID No.:64<br>ctcgcattccagATGTCTATCAGC | SEQ ID No.: 65<br>TATGCTGTCAAGagctgggtctg |
| 4 | 250-330 | 191 | SEQ ID No.:66<br>cctacattgtagATCATTGAGAAG | SEQ ID No.: 67<br>CAGGGACATAGGtaaggtggcctg |
| 5 | 331-402 | 226 | SEQ ID No.:68<br>tcccaactcaggAATGTTCTAGAA | SEQ ID No.: 69<br>GAAGATGCGTGGCggtaggtaggtactgg |
| 6 | 403-509 | 87 | SEQ ID No.:70<br>ctggcctgcacaGGATCCATCCTA | SEQ ID No.: 71<br>GCATAACAAAGGtgtggcagggac |
| 7 | 510-566 | 114 | SEQ ID No.:72<br>cacctcactaggCATCGCCCACAG | SEQ ID No.: 73<br>CCCCAACCAGGTgaggctgcctga |
| 8 | 567-659 | 229 | SEQ ID No.:74<br>ccattcccaggtCTCGCCAGTGAA | SEQ ID No.: 75<br>GCTGCTCACCCCggtgagggcagt |
| 9 | 660-1020 | 309 | SEQ ID No.:76<br>ccctgccccacaGTGTGGGTCAGC | SEQ ID No.: 77<br>TGGGTGCAGGGGgtaagccttggg |
| 10 | 1021-1062 | 280 | SEQ ID No.:78<br>gacttcttacagTGTGCCCCAGAG | SEQ ID No.: 79<br>TTGGTTCTGCAGaggtgaggcctg |
| 11 | 1063-3073 | 127 | SEQ ID No.:80<br>catcctatccccAGGAACAGCTGT | SEQ ID No.: 81<br>GTCATTTAAAAAtttctgtgcagt |
| 12 | | | SEQ ID No.:82<br>aaacacaagcctAAAAAAAAAacaagcatggg | |

*Fig. 12* ously understood. Even if several
MNK KINASE HOMOLOGOUS PROTEINS INVOLVED IN THE REGULATION OF ENERGY HOMEOSTASIS AND ORGANELLE METABOLISM This application is a continuation of U.S. Ser. No. 12/174,301 filed Jul. 16, 2008 now U.S. Pat. No. 8,076,098, which is a continuation of U.S. Ser. No. 10/494,010 filed Aug. 12, 2004 now abandoned which is a 371 of International Application PCT/EP2002/12075 filed Oct. 29, 2002, which claims the benefit of European Patent Applications No. 01125812.6 filed on Oct. 29, 2001 and EP02011 073.0 filed on May 17, 2002, the disclosure of which is incorporated herein in its entirety by reference.

This invention relates to the use of nucleic acid sequences of the Mitogen Activating Protein (MAP) kinase-interacting kinase (Mnk) gene family and amino acid sequences encoded thereby, and to the use of these sequences or effectors of Mnk nucleic acids or polypeptides, particularly Mnk kinase inhibitors and activators, in the diagnosis, study, prevention, and treatment of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs.

There are several metabolic diseases of human and animal metabolism, e.g., obesity and severe weight loss that relate to energy imbalance where caloric intake versus energy expenditure is imbalanced. Obesity is one of the most prevalent metabolic disorders in the world. It is a still poorly understood human disease that becomes more and more relevant for western society. Obesity is defined as a body weight more than 20% in excess of the ideal body weight, frequently resulting in a significant impairment of health. It is associated with an increased risk for cardiovascular disease, hypertension, diabetes, hyperlipidemia and an increased mortality rate. Besides severe risks of illness, individuals suffering from obesity are often isolated socially.

Obesity is influenced by genetic, metabolic, biochemical, psychological, and behavioral factors. As such, it is a complex disorder that must be addressed on several fronts to achieve lasting positive clinical outcome. Since obesity is not to be considered as a single disorder but as a heterogeneous group of conditions with (potential) multiple causes, it is also characterized by elevated fasting plasma insulin and an exaggerated insulin response to oral glucose intake (Koltermann, J. Clin. Invest 65, 1980, 1272-1284). A clear involvement of obesity in type 2 diabetes mellitus can be confirmed (Kopelman, Nature 404, 2000, 635-643).

The molecular factors regulating food intake and body weight balance are incompletely understood. Even if several candidate genes have been described which are supposed to influence the homeostatic system(s) that regulate body mass/weight, like leptin, VCPI, VCPL or the peroxisome proliferator-activated receptor-gamma co-activator, the distinct molecular mechanisms and/or molecules influencing obesity or body weight/body mass regulations are not known. In addition, several single-gene mutations resulting in obesity have been described in mice, implicating genetic factors in the etiology of obesity (Friedman and Leibel, 1990, Cell 69: 217-220). In the obese mouse, a single gene mutation (obese) results in profound obesity, which is accompanied by diabetes (Friedman et al., 1991, Genomics 11: 1054-1062).

Therefore, the technical problem underlying the present invention was to provide for means and methods for modulating (pathological) metabolic conditions influencing thermogenesis, body-weight regulation and/or energy homeostatic circuits. The solution to said technical problem is achieved by providing the embodiments characterized in the claims.

BRIEF DESCRIPTION OF THE DRAWINGS

FIGS. 3A and 3B show the comparison of Mnk proteins.

FIG. 3A shows the comparison (CLUSTAL X 1.8) multiple-sequence alignment of Mnk proteins from *Drosophila* and human Mnk proteins: hXP 030637 (SEQ ID NO.: 2) refers to human Mnk2 (identical to the protein encoded by Genbank Accession No. AF237775 (SEQ ID NO.: 1); hXP__001600 (SEQ ID NO.: 6) refers to human Mnk1 (identical to the protein encoded by the nucleic acid sequence having the Genbank Accession No. AB000409.1 (SEQ ID NO.: 56); dmAB18789 refers to the protein having the amino acid sequence SEQ ID NO.: 40 and encoded by *Drosophila* Lk6 gene with GadFly Accession No. CG17342. Gaps in the alignment are represented as -.

FIG. 3B shows the comparison (CLUSTAL W 1.82) of human Mnk2 proteins. Amino acid sequence having Genbank Accession Number XM 030637.3 is identical to the amino acid sequence having Genbank Accession Number AF237775 (SEQ ID NO.: 2). The amino acid sequence labeled NM__017572.1 (SEQ ID NO.: 4) shows a different variant of the human Mnk2 protein.

FIG. 3C shows the comparison (CLUSTAL W 1.82) of human Mnk1 proteins. Amino acid sequence having Genbank Accession Number XM 001600.2 is identical to Genbank Accession Number AB000409.1 (SEQ ID NO.: 56), and Genbank Accession Number NM__003684.2 (SEQ ID NO.: 59) shows a different variant of the Mnk1 protein.

FIG. 3D. Nucleic acid sequence of human MAP kinase-interacting kinase (Mnk) 2a (SEQ ID NO.: 1) having GenBank Accession Number AF237775 (alternatively designated as GenBank Accession Number XM__030637).

FIG. 3E. Amino acid sequence of human MAP kinase-interacting kinase (Mnk) 2a (SEQ ID NO.: 2) encoded by the nucleic acid sequence SEQ ID NO.: 1 (alternatively designated as GenBank Accession Number XM__030637).

FIG. 3F. Nucleic acid sequence of human MAP kinase-interacting kinase (Mnk) 2b (SEQ ID NO.: 3) contained within the nucleic acid sequence having GenBank Accession Number AF237776 (SEQ ID NO.: 54) which is a variant of the nucleic acid sequence labeled NM__17572.2 (SEQ ID NO.: 55).

FIG. 3G. Amino acid sequence of human MAP kinase-interacting kinase (Mnk) 2b (SEQ ID NO.: 4) encoded by the nucleic acid sequence SEQ ID NO.: 3, or nucleic acid sequences having the GenBank Accession Numbers AF237776 (SEQ ID NO.: 54), which is a variant of the nucleic acid sequence having the GenBank Accession Number NM_017572.2 (SEQ ID NO.: 55).

FIG. 3H. Nucleic acid sequence of human MAP kinase-interacting kinase (Mnk) 1 (SEQ ID NO.: 5); GenBank Accession Number AB000409 (SEQ ID NO: 56), alternatively designated as GenBank Accession Number NM 003684 (SEQ ID NO.: 87) or XM_001600).

FIG. 3I. Amino acid sequence of human MAP kinase-interacting kinase (Mnk) 1 (SEQ ID NO.: 6) encoded by the nucleic acid sequence having GenBank Accession Number AB000409 (SEQ ID NO: 56), alternatively designated as GenBank Accession Number NM 003684 (SEQ ID NO.: 87) or XM_001600).

FIG. 5A shows the real-time PCR analysis of Mnk2 in wild-type mouse tissues

FIG. 5B shows the expression of mouse Mnk2 gene in fasted and obese (ob/ob) mice models.

FIG. 6A shows the real-time PCR analysis of Mnk1 in wildtype mouse tissues

FIG. 6B shows the real-time PCR mediated comparison of Mnk1 expression in different mouse models.

FIGS. 7A and 7B show the UCPy sequences SEQ ID NOs.: 7 and 8.

FIG. 7A shows the nucleic acid sequence (SEQ ID NO.: 7) of a full-length cDNA encoding the *Drosophila* UCPy protein (SEQ ID NO.: 8). The open reading frame is underlined.

FIG. 7B shows the amino acid sequence *Drosophila* UCPy protein (SEQ ID NO.: 8) encoded by the underlined sequence shown in FIG. 7A.

FIG. 8A shows reduction in cellular triglyceride levels (μg/mg protein) in cells over-expressing Mnk2 compared to control cells. All samples were analyzed in duplicates (s1; sample 1, s2; sample 2). The Y-axis shows cellular triglyceride levels (μg/mg protein) and the X-axis shows days of cell differentiation.

FIGS. 9A and 9B show the expression of human Mnk2 in different human tissues.

FIG. 9A shows the expression of human Mnk2A and Mnk2B in different human tissues.

FIG. 9B shows the expression of human Mnk2A and human Mnk2B during adipocyte differentiation.

FIG. 12 shows the nucleic acid regions (SEQ ID NOs.: 60-82) encompassing the exon/intron boundaries of the mouse Mnk2 gene. Exon/intron boundaries of the mouse Mnk2 gene are illustrated in this figure. Exon numbers, the position of the exons of the cDNA having GenBank accession number BC010256 (SEQ ID NO.: 57) and intron lengths are indicated. Intron sequences are shown in lowercase letters, exon sequences are shown in capital, bold letters.

Figure 1:
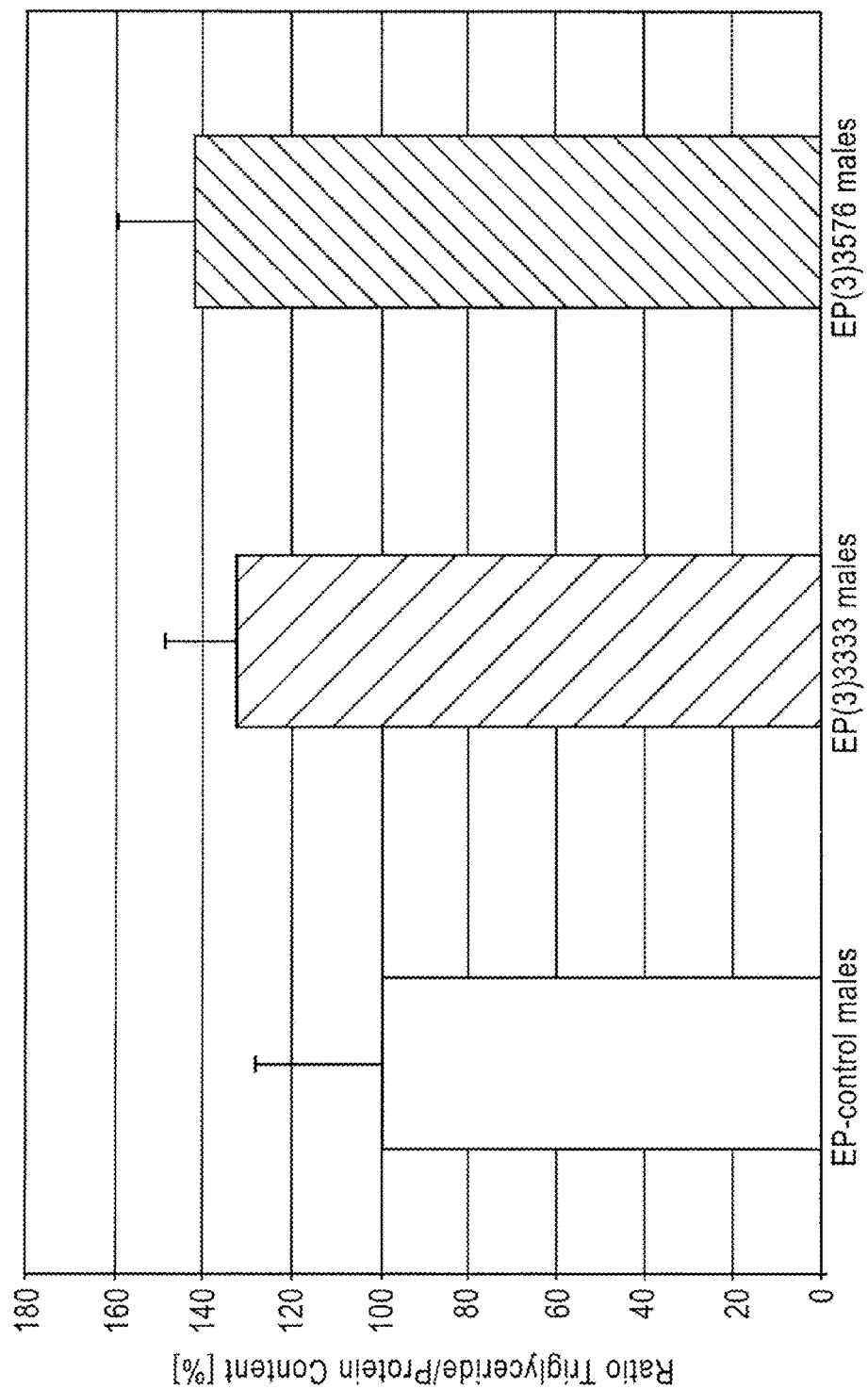
FIG. 1 shows the increase of triglyceride content of EP(3) 3333 and EP(3)3576 male flies caused by homozygous viable integration of the P-vector (in comparison to EP-control males). Shown is the ratio of the triglyceride to protein content of the mutants in percent (%)).

Accordingly, the present invention relates to genes with novel functions in body-weight regulation, energy homeostasis, metabolism, and obesity. The present invention provides for a specific gene involved in the regulation of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, cancers of the reproductive organs, and sleep apnea, and disorders related to ROS defence, such as diabetes mellitus, neurodegenerative disorders, and cancer. The present invention describes the human Mnk genes as being involved in those conditions mentioned above, in particular the human Mnk2 gene variants.

The term "GenBank Accession number" relates to National Center for Biotechnology Information (NCBI) GenBank database entries (Benson et al, Nucleic Acids Res. 28, 2000, 15-18).

Protein kinases are important molecules involved in the regulation of many cellular functions. The Drosophila melanogaster LK6 serine/threonine kinase gene has been described as a short-lived kinase that can associate with microtubules (J. Cell Sci. 1997 110(2):209-219). Genetic analysis in the development of the Drosophila compound eye suggested a role in the modulation of the RAS signaling pathway (Genetics 2000 156(3):1219-1230). As described in this invention, the closest human homologues of Drosophila LK6 kinase are the MAP kinase-interacting kinase 2 (Mnk2, for example the variants Mnk2a and Mnk2b) and MAP kinase-interacting kinase 1 (Mnk1). All three proteins are predominantly localized in the cytoplasm. Mnks are phosphorylated by the pk42 MAP kinases Erk1 and Erk2 and the p38 MAP kinases. This phosphorylation is triggered in response to growth factors, phorbol esters and oncogenes like Ras and Mos as well as by stress signaling molecules and cytokines. The phosphorylation of Mnk proteins stimulates its kinase activity towards eukaryotic initiation factor 4E (EMBO J. 16: 1909-1920 (1997), Mol Cell Biol 19:1871-1880 (1999), Mol Cell Biol 21: 743-754 (2001)). Phosphorylation of eukaryotic initiation factor 4E (eIF4E) results in a regulation of protein translation (Mol Cell Biol 22: 5500-5511 (2001)).

There are different hypothesis describing the mode of stimulation of the protein translation by Mnk proteins. Most publications described a positive stimulatory effect on the cap-dependent protein translation upon activation of MAP kinase-interacting kinases. Thus, activation of Mnk proteins might lead to an indirect stimulation or regulation of protein translation, for example by the action on cytosolic phospholipase 2 alpha (BBA 1488:124-138, 2000).

Inhibitors of Mnk (referred to as CGP57380 and CGP052088) were described in the prior art (see, Knauf et al., 2001, Mol. Cell. Biol. 21:5500, Tschopp et al., 2000, Mol Cell Biol Res Comm 3:205 and Slentz-Kesler et al., 2000, Genomics 69:63). CGP052088 is a staurosporine derivative with an IC50 of 70 nM for inhibition of in vitro kinase activity of Mnk1. CGP57380 is a selective low-molecular weight, non cytotoxic inhibitor of Mnk2 (Mnk2a or Mnk2b) or Mnk1. The addition of CGP57380 to cell culture cells transfected with Mnk2 (Mnk2a or Mnk2b) or Mnk1 resulted in a strong reduction in phosphorylated eIF4E.

So far, it has not been described that Mnk kinases are involved in the regulation of body-weight and thermogenesis, and thus may be associated with metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs. In this application we demonstrate that the correct gene doses of Mnk kinases are essential for maintenance of energy homeostasis. A genetic screen was used to identify that mutation of Mnk kinase homologous genes causes obesity, reflected by a significant increase of triglyceride content, the major energy storage substance. Furthermore, in this invention we relate to mutations of Mnk kinases that affect the activity of uncoupling proteins (UCPs), thereby leading to an altered mitochondrial activity. We also relate to the treatment of metabolic disorders with the Mnk-specific inhibitor CGP57380 and derivatives thereof.

In this invention we demonstrate that the correct gene dose of the Drosophila melanogaster homologue of Mnk is essential for maintenance of energy homeostasis in adult flies and for the activity of mitochondrial uncoupling protein. A genetic screen was used to identify that mutation of an Mnk homologous gene causes obesity in Drosophila melanogaster, reflected by a significant increase of triglyceride content, the major energy storage substance. In a second screen designed to identify factors that modulate activity of uncoupling protein, we discovered that mutation of this Mnk homologous gene caused a reduction the activity of uncoupling protein. Thus, the invention is also based on the finding that the Drosophila homologue of Mnk is contributing to membrane stability and/or function of organelles, preferably mitochondria. It was found that mutations in LK6 kinases affect the activity of uncoupling proteins (UCPs), thereby leading to an altered mitochondrial activity.

Further, we show that the mouse homologue of the Mnk2 gene is regulated by fasting and by genetically induced obesity. Furthermore, the Mnk2 mRNA is strongly upregulated during adipocyte differentiation in vitro (see EXAMPLES). This invention shows that Mnk2 transcripts are expressed in most mouse tissues but with highest expression levels in white (WAT) and brown adipose tissue (BAT). The expression in white adipose tissue is reduced by approx. 60% in fasted mice and in ob/ob mice. The analysis of actin-mMnk2DN transgenic mice showed that the ectopic expression of mMnk2DN transgene (see Examples) leads to an clear increase in bodyweight. The effect seems to be diet-independent, as it can be seen on control diet as well as on high fat diet. Thus, we conclude that Mnk2 is playing an important role in the regulation of body-weight.

In addition, we found that the relative expression levels of both human Mnk2 splice variants is the same for all tissues analyzed. Both Mnk2 variants show highest expression levels in human tissues relevant for metabolic disorders namely adipose and muscle tissue. Furthermore, both Mnk2 variants are upregulated during human adipocyte differentiation. Thus, we conclude that Mnk2 (or variants thereof) has a function in the metabolism of mature human adipocytes.

We also found that cellular triglyceride levels in Mnk2 overexpressing cells were significantly lower from day 4 to day 12 of adipogenesis compared to that in the control cells. Furthermore, Mnk2 overexpressing cells were less effective at synthesizing lipids from exogenous glucose. Consequently, the levels of insulin stimulated lipid synthesis are significantly lower at day 12 of adipogenesis when compared to control cells. We also found that transport of exogenous fatty acids across the plasma membrane of Mnk2 overexpressing cells and hence esterification of these metabolites was considerably lower at day 12 of adipogenesis when compared to control cells.

Polynucleotides encoding a protein with homologies to proteins of the Mnk kinase family are suitable to investigate diseases and disorders as described above. Discovery of molecules related to Mnk kinases satisfies a need in the art by providing new compositions useful in diagnosis, treatment, and prognosis of diseases and disorders as described above.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies, which are reported in the publications which might be used in connection with the invention. Nothing herein is to be construed as an admission that the invention is not entitled to antedate such disclosure.

The present invention discloses that Mnk homologous proteins are regulating the energy homeostasis and fat metabolism, especially the metabolism and storage of triglycerides, and polynucleotides, which identify and encode the proteins disclosed in this invention. The present invention also discloses that Mnk homologous proteins are directly or indirectly involved in membrane stability and/or function of organelles, in particular mitochondria, and polynucleotides, which identify and encode the proteins disclosed in this invention. The invention also relates to vectors, host cells, antibodies, and recombinant methods for producing the polypeptides and polynucleotides of the invention. The invention also relates to the use of these sequences in the diagnosis, study, prevention, and treatment of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs.

Mnk homologous proteins and nucleic acid molecules coding therefore are obtainable from insect or vertebrate species, e.g. mammals or birds. Particularly preferred are human Mnk homologous polypeptides and nucleic acids encoding such polypeptides, particularly polypeptides and nucleic acids encoding a human Mnk2 protein (splice variant Mnk2a (SEQ ID NO.: 2) encoded by the nucleic acid sequence having Genbank Accession No. AF237775 (SEQ ID NO.: 1) as shown in FIGS. 3D and 3E, or splice variant Mnk2b (SEQ ID NO.: 4) encoded by the nucleic acid sequences having GenBank Accession AF237776 (SEQ ID NO.: 3) or No. NM_017572.2 (SEQ ID NO.: 55), as shown in FIGS. 3F and 3G. Genbank Accession No. AF237775 (SEQ ID NO.: 1) is identical to formerly Genbank Accession No. XM_030637 which was removed at the submitters request; see a Clustal W multiple sequence alignment in FIG. 3B, see also sequences in FIGS. 3D-G) or a human Mnk1 protein (SEQ ID NO.: 6) encoded by the nucleic acid sequences having Genbank Accession No. AB000409.1 (SEQ ID NO.: 56) and NM_003684.2 (SEQ ID NO.: 5) as shown in FIGS. 3H and 3I); Genbank Accession No. AB000409 is identical to formerly Genbank Accession No. XM_001600 which was removed at the submitters request; see a Clustal W multiple sequence alignment in FIG. 3C).

The invention particularly relates to a nucleic acid molecule encoding a polypeptide contributing to regulating the energy homeostasis and the metabolism of triglycerides, and/or contributing to membrane stability and/or function of organelles, wherein said nucleic acid molecule comprises (a) the nucleotide sequences of Genbank Accession Nos. AF237775 (SEQ ID NO.: 1), NM_017572.2 (SEQ ID NO.: 55), AB000409.1 (SEQ ID NO.: 56), or NM_003684.2 (SEQ ID NO.: 5), and/or the complement thereof, (b) a nucleotide sequence which hybridizes at 50° C. in a solution containing 1×SSC and 0.1% SDS to the nucleic acid molecule of (a), particularly a nucleic acid encoding the amino acid sequences as shown in FIG. 3, (c) a sequence corresponding to the sequences of (a) or (b) within the degeneration of the genetic code, (d) a sequence which encodes a polypeptide which is at least 85%, preferably at least 90%, more preferably at least 95%, more preferably at least 98% and up to 99.6% identical to the amino acid sequences shown in FIG. 3, (e) a sequence which differs from the nucleic acid molecule of (a) to (d) by mutation and wherein said mutation causes an alteration, deletion, duplication or premature stop in the encoded polypeptide or (f) a partial sequence of any of the nucleotide sequences of (a) to (e) having a length of at least 15 bases, preferably at least 20 bases, more preferably at least 25 bases and most preferably at least 50 bases.

The invention is based on the finding that Mnk homologous proteins (herein referred to as Mnk), particularly Mnk2 (Mnk2a or Mnk2b) or Mnk1, and the polynucleotides encoding these, are involved in the regulation of triglyceride storage and therefore energy homeostasis. The present invention also discloses that Mnk homologous proteins are directly or indirectly involved in membrane stability and/or function of organelles, in particular mitochondria, and polynucleotides, which identify and encode the proteins disclosed in this invention. The invention describes the use of compositions comprising the nucleotides, proteins or effectors thereof, e.g. antibodies, aptamers, anti-sense molecules, ribozymes, RNAi molecules, peptides, low-molecular weight organic molecules and other receptors recognizing the nucleic acid molecule or the polypeptide, for the diagnosis, study, prevention, or treatment of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs.

Accordingly, the present invention relates to genes with novel functions in body-weight regulation, energy homeostasis, metabolism, and obesity. To find genes with novel functions in energy homeostasis, metabolism, and obesity, a functional genetic screen was performed with the model organism *Drosophila melanogaster* (Melgen). *Drosophila melanogaster* is one of the most intensively studied organisms in biology and serves as a model system for the investigation of many developmental and cellular processes common to higher eukaryotes, including humans (see, for example, Adams et al., Science 287: 2185-2195 (2000)). The success of *Drosophila melanogaster* as a model organism is largely due to the power of forward genetic screens to identify the genes that are involved in a biological process (see, Johnston Nat Rev Genet. 3: 176-188 (2002); Rorth, Proc Natl Acad Sci USA 93: 12418-12422 (1996)). One resource for screening was a proprietary *Drosophila melanogaster* stock collection of EP-lines. The P-vector of this collection has Gai4-UAS-binding sites fused to a basal promoter that can transcribe adjacent genomic *Drosophila* sequences upon binding of Gal4 to UAS-sites. This enables the EP-line collection for overexpression of endogenous flanking gene sequences. In addition, without activation of the UAS-sites, integration of the EP-element into the gene is likely to cause a reduction of gene activity, and allows determining its function by evaluating the loss-of-function phenotype.

Triglycerides are the most efficient storage for energy in cells, and are significantly increased in obese patients. In this invention, we have used a genetic screen to identify, that mutations of Lk6 homologous genes cause changes in the body weight which is reflected by a significant change in the triglyceride levels. In order to isolate genes with a function in energy homeostasis, several thousand EP-lines were tested for their triglyceride content after a prolonged feeding period. Lines with significantly changed triglyceride content were selected as positive candidates for further analysis. In this invention, the content of triglycerides of a pool of flies with the same genotype after feeding for six days was analyzed using a triglyceride assay, as, for example, but not for limiting the scope of the invention, is described below in the examples section. The change of triglyceride content due to the loss of a gene function suggests gene activities in energy homeostasis in a dose dependent manner that controls the amount of energy stored as triglycerides.

The result of the triglyceride content analysis is shown in FIG. 1. Flies homozygous for EP(3)3333 and EP(3)3576 integrations were analyzed in the triglyceride assay. The average increase of triglyceride content of the homozygous viable lines EP(3)3333 and EP(3)3576 is approx. 140% (FIG. 1). Therefore, the very likely loss of a gene activity in the gene locus 86F7 (estimated, chromosomal localisation where the EP-vector of EP(3)3333 and EP(3)3576 flies is integrated) is responsible for changes in the metabolism of the energy storage triglycerides, therefore representing in both cases an obese fly model. The increase of triglyceride content due to the loss of a gene function suggests gene activities in energy homeostasis in a dose dependent manner that controls the amount of energy stored as triglycerides.

Figure 2:
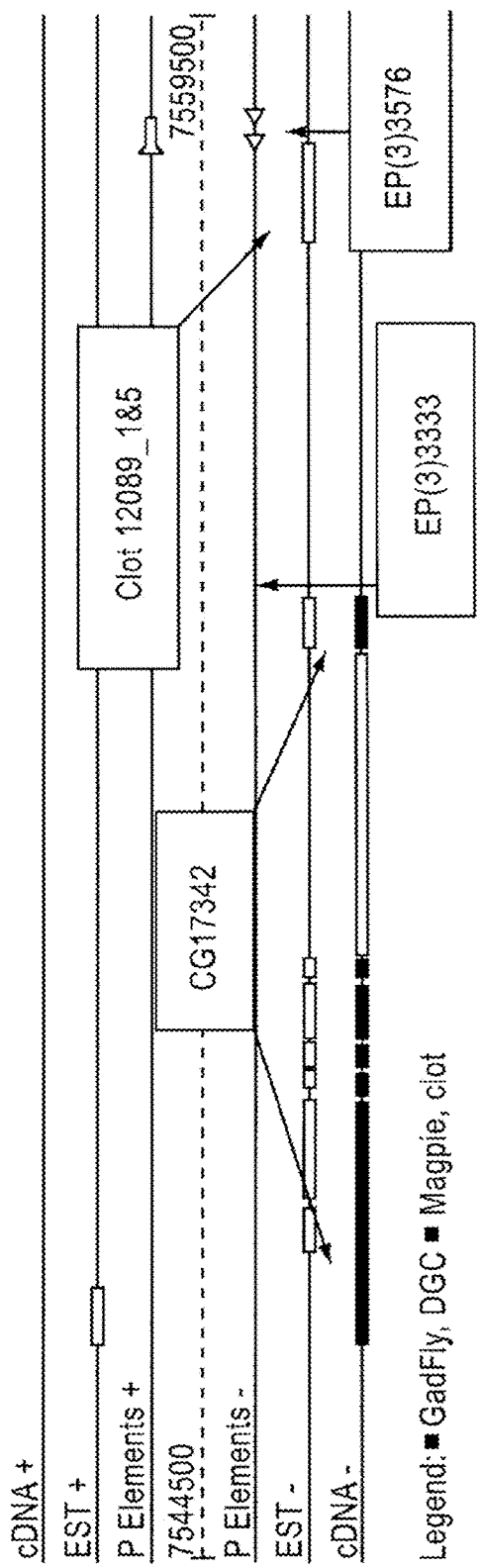
FIG. 2 shows the molecular organization of the mutated LK6 gene locus. The dotted black line represents the position of the cDNA (from position 7544500 to 7559500 on chromosome 3R) that includes the integration sites of EP(3)3333 and EP(3)3576. Transcribed DNA sequences (ESTs) and predicted exons are shown as bars in the lower two lines. Predicted exons of gene CG17342 (GadFly, Lk6) are shown as black bars and introns as open bars. Lk6 encodes for a gene that is predicted by GadFly sequence analysis programs as Gadfly Accession Number CG17342.

Nucleic acids encoding the Mnk protein of the present invention were identified using a plasmid-rescue technique. Genomic DNA sequences were isolated that are localized directly 3' to the EP(3)3333 and EP(3)3576 integrations. Using those isolated genomic sequences public databases like Berkeley *Drosophila* Genome Project (GadFly; see also FlyBase (1999) Nucleic Acids Research 27:85-88) were screened thereby confirming the integration side of EP(3) 3333 in the 5' region of a 5' exon of the Mnk homologous gene and EP(3)3576 in the 5' region of an alternative 5' exon (FIG. 2). FIG. 2 shows the molecular organization of this locus. Genomic DNA sequence is represented by the assembly as a black dotted line in the middle that includes the integration site of EP(3)3333 and EP(3)3576. Numbers represent the coordinates of the genomic DNA (starting at position 7544500 on chromosome 3R). Grey bars on the two "cDNA"-lines represent the predicted genes (Gad Fly & Magpie), and grey symbols on the "P-Elements"-line the EP-vector integration sites. Predicted exons of gene CG17342 are shown as dark grey bars and predicted introns as light grey bars.

Lk6 (the Mnk homologous gene in *Drosophila*) encodes for a gene that is predicted by GadFly sequence analysis programs (GadFly Accession Number CG17342). No functional data described the regulation of obesity and metabolic diseases are available in the prior art for the genes shown in FIG. 3, referred to as Mnk in the present invention.

It is also preferred that the nucleic acid molecule encodes a polypeptide contributing to membrane stability and/or function of organelles and represents a protein of *Drosophila* which has been found to be able to modify UCPs, see also appended examples. As demonstrated in the appended examples, the here described polypeptide (and encoding nucleic acid molecule) was able to modify, e.g. enhance a specific eye phenotype in *Drosophila* which was due to the overexpression of the *Drosophila melanogaster* gene dUCPy. The overexpression of dUCPy (with homology to human UCPs) in the compound eye of *Drosophila* led to a clearly visible eye defect which can be used as a "read-out" for a genetical" modifier screen".

In said "modifier screen" thousands of different genes are mutagenized to modify their expression in the eye. Should one of the mutagenized genes interact with dUCPy and modify its activity an enhancement or suppression of the eye defect will occur. Since such flies are easily to discern they can be selected to isolate the interacting gene. As shown in the appended examples, a gene was deduced that can enhance the eye defect induced by the activity of dUCPy. This gene is called the LK6 gene of *Drosophila* with high homologies to the human Mnk proteins, as described above. It is envisaged that mutations in the herein described Mnk-polypeptides (and genes) lead to phenotypic and/or physiological chances which may comprise a modified and altered mitochondrial activity. This, in turn, may lead to, inter alia, an altered energy metabolism, altered thermogenesis and/or altered energy homeostasis. As shown in the appended examples, a gene was deduced that can enhance the eye defect induced by the activity of dUCPy.

Mnk homologous proteins and nucleic acid molecules coding therefor are obtainable from insect or vertebrate species, e.g. mammals or birds. Particularly preferred are nucleic acids encoding the human Lk6/Mnk homologs, particularly Mnk2 variants (Mnk2a or Mnk2b) or Mnk1. The present invention is describing a polypeptide comprising the amino acid sequence of Mnk, particularly Mnk2 variants (Mnk2a or Mnk2b) or Mnk1. A comparison (Clustal X 1.8) between the Mnk proteins of different species (human and *Drosophila*) was conducted and is shown in FIG. 3A. Based upon homology, Mnk protein of the invention and each homologous protein or peptide may share at least some activity.

In a particular embodiment, the invention encompasses the polynucleotide comprising the nucleic acid sequence of GenBank Accession Number AF237775 (SEQ ID NO.: 1), NM_017572.1 (SEQ ID NO.: 3), AB000409.1 (SEQ ID NO.: 56), or NM_003684.2 (SEQ ID NO.: 5). It will be appreciated by those skilled in the art that as a result of the degeneracy of the genetic code, a multitude of nucleotide sequences encoding Mnk, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequences of naturally occurring Mnk, and all such variations are to be considered as being specifically disclosed. Although nucleotide sequences which encode Mnk and its variants are preferably capable of hybridizing to the nucleotide sequences of the naturally occurring Mnk under appropriately selected conditions of stringency, it may be advantageous to produce nucleotide sequences encoding Mnk or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding Mnk and its derivatives without altering the encoded amino acid sequences include the production of RNA transcripts having more desirable properties, such as a greater half-life, than transcripts produced from the naturally occurring sequences. The invention also encompasses production of DNA sequences, or portions thereof, which encode Mnk and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding Mnk any portion thereof.

Also encompassed by the invention are polynucleotide sequences that are capable of hybridizing to the claimed nucleotide sequences, and in particular, those shown in GenBank Accession Numbers AF237775 (SEQ ID NO.: 1), NM_017572.1 (SEQ ID NO.: 3), AB000409.1 (SEQ ID NO.: 56), or NM_003684.2 (SEQ ID NO.: 5), under various conditions of stringency. Hybridization conditions are based on the melting temperature (Tm) of the nucleic acid binding complex or probe, as taught in Wahl, G. M. and S. L. Berger (1987; Methods Enzymol. 152:399-407) and Kimmel, A. R. (1987; Methods Enzymol. 152:507-511), and may be used at a defined stringency. Preferably, hybridization under stringent conditions means that after washing for 1 h with 1×SSC and 0.1% SDS at 50° C., preferably at 55° C., more preferably at 62° C. and most preferably at 68° C., particularly for 1 h in 0.2×SSC and 0.1% SDS at 50° C., preferably at 55° C., more preferably at 62° C. and most preferably at 68° C., a positive hybridization signal is observed. Altered nucleic acid sequences encoding Mnk which are encompassed by the invention include deletions, insertions, or substitutions of different nucleotides resulting in a polynucleotide that encodes the same or a functionally equivalent Mnk.

The encoded proteins may also contain deletions, insertions, or substitutions of amino acid residues, which produce a silent change and result in a functionally equivalent Mnk. Deliberate amino acid substitutions may be made on the basis of similarity in polarity, charge, solubility, hydrophobicity, hydrophilicity, and/or the amphipathic nature of the residues as long as the biological activity of Mnk is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding Mnk. As used herein, an "allele" or "allelic sequence" is an alternative form of the gene, which may result from at least one mutation in the nucleic acid sequence. Alleles may result in altered mRNAs or polypeptides whose structures or function may or may not be altered. Any given gene may have none, one, or many allelic forms. Common mutational changes, which give rise to alleles, are generally ascribed to natural deletions, additions, or substitutions of nucleotides. Each of these types of changes may occur alone, or in combination with the others, one or more times in a given sequence. Methods for DNA sequencing which are well known and generally available in the art may be used to practice any embodiments of the invention. The methods may employ such enzymes as the Klenow fragment of DNA polymerase I, SEQUENASE DNA Polymerase (US Biochemical Corp, Cleveland Ohio), Taq polymerase (Perkin Elmer), thermostable T7 polymerase (Amersham, Chicago, Ill.), or combinations of recombinant polymerases and proofreading exonucleases such as the ELONGASE Amplification System (GIBCO/BRL, Gaithersburg, Md.). Preferably, the process is automated with machines such as the Hamilton MICROLAB 2200 (Hamilton, Reno Nev.), Peltier thermal cycler (PTC200; MJ Research, Watertown, Mass.) and the ABI 377 DNA sequencers (Perkin Elmer). The nucleic acid sequences encoding Mnk may be extended utilising a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). Inverse PCR may also be used to amplify or extend sequences using divergent primers based on a known region (Triglia, T. et al. (1988) Nucleic Acids Res. 16:8186). Another method which may be used is capture PCR which involves PCR amplification of DNA fragments adjacent to a known sequence in human and yeast artificial chromosome DNA (Lagerstrom, M. et al. (PCR Methods Applic. 1: 111-119). Another method which may be used to retrieve unknown sequences is that of Parker, J. D. et al. (1991; Nucleic Acids Res. 19:3055-3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences, which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions. Capillary electrophoresis systems, which are commercially available, may be used to analyse the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA, which might be present in limited amounts in a particular sample.

In another embodiment of the invention, polynucleotide sequences or fragments thereof which encode Mnk, or fusion proteins or functional equivalents thereof, may be used in recombinant DNA molecules to direct expression of Mnk in appropriate host cells. Due to the inherent degeneracy of the genetic code, other DNA sequences, which encode substantially the same, or a functionally equivalent amino acid sequence may be produced and these sequences may be used to clone and express Mnk. As will be understood by those of skill in the art, it may be advantageous to produce Mnk-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life, which is longer than that of a transcript generated from the naturally occurring sequence. The nucleotide sequences of the present invention can be engineered using methods generally known in the art in order to alter Mnk encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding Mnk may be ligated to a heterologous sequence to encode a fusion protein. For example, to screen peptide libraries for inhibitors of Mnk activities, it may be useful to construct chimeric Mnk proteins that can be recognized by commercially available antibodies. A fusion protein may also be engineered to contain a cleavage site located between the Mnk encoding sequence and the heterologous protein sequences, so that Mnk may be cleaved and purified away from the heterologous moiety. In another embodiment, sequences encoding Mnk may be synthesized, in whole or in part, using chemical methods well known in the art (see Caruthers et al. (1980) Nucl. Acids Res. Symp. Ser. 7:215-223, Horn et al. (1980) Nucl. Acids Res. Symp. Ser. 7:225-232). Alternatively, the proteins themselves may be produced using chemical methods to synthesize the amino acid sequence of Mnk, or a portion thereof. For example, peptide synthesis can be performed using various solid-phase techniques (Roberge et al. (1995) Science 269:202-204) and automated synthesis may be achieved, for example, using the ABI431A peptide synthesizer (Perkin Elmer). The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequences of Mnk, or any part thereof, may be altered during direct synthesis and/or combined using chemical methods with sequences from other proteins, or any part thereof, to produce a variant polypeptide.

In order to express a biologically active Mnk, the nucleotide sequences encoding Mnk functional equivalents, may be inserted into appropriate expression vectors, i.e., a vector, which contains the necessary elements for the transcription and translation of the inserted coding sequence. Methods, which are well known to those skilled in the art, may be used to construct expression vectors containing sequences encoding Mnk and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

Regulatory elements include for example a promoter, an initiation codon, a stop codon, a mRNA stability regulatory element, and a polyadenylation signal. Expression of a polynucleotide can be assured by (i) constitutive promoters such as the Cytomegalovirus (CMV) promoter/enhancer region, (ii) tissue specific promoters such as the insulin promoter (see, Soria et al., 2000, Diabetes 49:157), SOX2 gene promoter (see Li et al., 1998, Curr. Biol. 8:971-4), Msi-1 promoter (see Sakakibara et al., 1997, J. Neuroscience 17:8300-8312), alpha-cardia myosin heavy chain promoter or human atrial natriuretic factor promoter (Kiug et al., 1996, J. Clin. Invest 98:216-24; Wu et al., 1989, J. Biol. Chem. 264:6472-79) or (iii) inducible promoters such as the tetracycline inducible system. Expression vectors can also contain a selection agent or marker gene that confers antibiotic resistance such as the neomycin, hygromycin or puromycin resistance genes. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y. and Ausubel, F. M. et al. (1989) Current Protocols in Molecular Biology, John Wiley & Sons, New York, N.Y. In a further embodiment of the invention, natural, modified or recombinant nucleic acid sequences encoding the proteins of the invention and homologous proteins may be ligated to a heterologous sequence to encode a fusion protein.

A variety of expression vector/host systems may be utilized to contain and express sequences encoding the proteins or fusion proteins. These include, but are not limited to, micro-organisms such as bacteria transformed with recombinant bacteriophage, plasmid or cosmid DNA expression vectors; yeast transformed with yeast expression vectors; insect cell systems infected with virus expression vectors (e.g., baculovirus, adenovirus, adeno-associated virus, lentivirus, retrovirus); plant cell systems transformed with virus expression vectors (e.g., cauliflower mosaic virus, CaMV; tobacco mosaic virus, TMV) or with bacterial expression vectors (e.g., Ti or PBR322 plasmids); or animal cell systems.

The "control elements" or "regulatory sequences" are those non-translated regions of the vectors, e.g. enhancers, promoters, 5' and 3' untranslated regions, which interact with host cellular proteins to carry out transcription and translation. Such elements may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters and enhancers derived from the genomes of plant cells (e.g., heat shock, RUBISCO; and storage protein genes)

or from plant viruses (e.g., viral promoters and leader sequences) may be cloned into the vector. In mammalian cell systems, promoters from mammalian genes or from mammalian viruses are preferable. If it is necessary to generate a cell line that contains multiple copies of the sequences encoding Mnk, vectors based on SV40 or EBV may be used with an appropriate selectable marker.

In bacterial systems, a number of expression vectors may be selected depending upon the use intended for Mnk. For example, when large quantities of Mnk are needed for the induction of antibodies, vectors, which direct high level expression of fusion proteins that are readily purified, may be used. Such vectors include, but are not limited to, the multifunctional E. coli cloning and expression vectors such as the BLUESCRIPT phagemid (Stratagene), in which the sequence encoding Mnk may be ligated into the vector in frame with sequences for the amino-terminal Met and the subsequent 7 residues of r3-galactosidase so that a hybrid protein is produced; piN vectors (Van Heeke, G. and S. M. Schuster (1989) J. Biol. Chem. 264:5503-5509); and the like. Vectors of the pGEX series (Amersham Biosciences, Uppsala, Sweden) may also be used to express foreign polypeptides as fusion proteins with Glutathione S-Transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will. In the yeast, Saccharomyces cerevisiae, a number of vectors containing constitutive or inducible promoters such as alpha factor, alcohol oxidase, and PGH may be used. For reviews, see Ausubel et al., (supra) and Grant et al. (1987) Methods Enzymol. 153:516-544.

In cases where plant expression vectors are used, the expression of sequences encoding Mnk may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17: 85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express Mnk. For example, in one such system, Autographa californica nuclear polyhedrosis virus (AcNPV) is used as a vector to express foreign genes in Spodoptera frugiperda cells or in Trichoplusia larvae. The sequences encoding Mnk may be cloned into a non-essential region of the virus, such as the polyhedrin gene, and place under control of the polyhedrin promoter. Successful insertions of Mnk will render the polyhedrin gene inactive and produce recombinant virus lacking coat protein. The recombinant viruses may then be used to infect, for example, S. frugiperda cells of Trichoplusia larvae in which Mnk may be expressed (Engelhard, E. K. et al. (1994) Proc. Nat. Acad. Sci. 91:3224-3227).

In mammalian host cells, a number of viral-based expression systems may be utilised. In cases where an adenovirus is used as an expression vector, sequences encoding Mnk may be ligated into an adenovirus transcription/translation complex consisting of the late promoter and tripartite leader sequence. Insertion in a non-essential E1 or E3 region of the viral genome may be used to obtain viable viruses which are capable of expressing Mnk in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding Mnk. Such signals include the ATG initiation codon and adjacent sequences. In cases where sequences encoding Mnk, its initiation codons, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, He La, MOCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines, which stably express Mnk may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells, which successfully express the introduced sequences. Resistant clones of stably transformed cells may be proliferated using tissue culture techniques appropriate to the cell type. Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes, which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:804 7-51). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55: 121-131).

In vivo, the enzymatic kinase activity of the unmodified polypeptides of Mnk towards a substrate can be enhanced by appropriate stimuli, triggering the phosphorylation of Mnk. This may be induced in the natural context by extracellular or intracellular stimuli, such as signaling molecules or environmental influences. One may generate a system containing active Mnk, may it be an organism, a tissue, a culture of cells or cell-free environment, by exogenously applying this stimulus or by mimicking this stimulus by a variety of the techniques, some of them described further below. A system containing activated Mnk may be produced (i) for the purpose of diagnosis, study, prevention, and treatment of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs, (ii) for the purpose of identifying or validating therapeutic candidate agents, pharmaceuticals or drugs that influence the genes of the invention or their encoded polypeptides, (iii) for the purpose of generating cell lysates containing activated polypeptides encoded by the genes of the invention, (iv) for the purpose of isolating from this source activated polypeptides encoded by the genes of the invention.

In one embodiment of the invention, one may produce activated Mnk independent of the natural stimuli for the above said purposes by, for example, but not limited to, (i) an agent that mimics the natural stimulus; (ii) an agents, that acts downstream of the natural stimulus, such as activators of the MAP kinase pathway, phorbol ester, anisomycin, constitutive active alleles of the MAP kinase kinase kinases, of the MAP kinase kinases, of the MAP kinase or Mnk itself as they are described or may be developed; (iii) by introduction of single or multiple amino acid substitutions, deletions or insertions within the sequence of Mnk to yield constitutive active forms; (iv) by the use of isolated fragments of Mnk. In addition, one may generate enzymatically active Mnk in an ectopic system, prokaryotic or eukaryotic, in vivo or in vitro, by co-transferring the activating components to this system. These could be, for example, but not limited to, components of the MAP kinase pathway such as constitutive active alleles of the MAP kinase kinases Mek1 or Mkk6, together with the MAP kinases ERK1 or ERK2 or the p38 MAPK isoforms. For example, one may activate isolated Mnk protein in solution with a mutant polypeptide of Mek1 containing the amino acid substitutions S218D and S222E together with isolated ERK2 kinase in the presence of 1.0 mM adenosine triphosphate and suitable buffer conditions such as 50 mM N-(2-Hydroxyethyl)-piperazine-N'-(2-ethanesuflonic acid)/potassium hydroxide pH 7.4, 5 mM magnesium chloride, 0.5 mM dithiothreitol (see FIG. 14).

Although the presence/absence of marker gene expression suggests that the gene of interest is also present, its presence and expression may need to be confirmed. For example, if the sequences encoding Mnk are inserted within a marker gene sequence, recombinant cells containing sequences encoding Mnk can be identified by the absence of marker gene function. Alternatively, a marker gene can be placed in tandem with sequences encoding Mnk under the control of a single promoter. Expression of the marker gene in response to induction or selection usually indicates expression of the tandem gene as well. Alternatively, host cells, which contain the nucleic acid sequences encoding Mnk and express Mnk, may be identified by a variety of procedures known to those of skill in the art. These procedures include, but are not limited to, DNA-DNA, or DNA-RNA hybridization and protein bioassay or immunoassay techniques, which include membrane, solution, or chip based technologies for the detection and/or quantification of nucleic acid or protein.

The presence of polynucleotide sequences encoding Mnk can be detected by DNA-DNA or DNA-RNA hybridization or amplification using probes or portions or fragments of polynucleotides encoding Mnk. Nucleic acid amplification based assays involve the use of oligonucleotides or oligomers based on the sequences encoding Mnk to detect transformants containing DNA or RNA encoding Mnk. As used herein "oligonucleotides" or "oligomers" refer to a nucleic acid sequence of at least about 10 nucleotides and as many as about 60 nucleotides, preferably about 15 to 30 nucleotides, and more preferably about 20-25 nucleotides, which can be used as a probe or amplimer.

A variety of protocols for detecting and measuring the expression of Mnk, using either polyclonal or monoclonal antibodies specific for the protein are known in the art. Examples include enzyme-linked immunosorbent assay (ELISA), radioimmunoassay (RIA), and fluorescence activated cell sorting (FAGS). A two-site, monoclonal-based immunoassay utilizing monoclonal antibodies reactive to two non-interfering epitopes on Mnk is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158: 1211-1216).

A wide variety of labels and conjugation techniques are known by those skilled in the art and may be used in various nucleic acid and amino acid assays. Means for producing labelled hybridization or PCR probes for detecting sequences related to polynucleotides encoding Mnk include oligo-labelling, nick translation, end-labelling or PCR amplification using a labelled nucleotide.

Alternatively, the sequences encoding Mnk, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labelled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio).

Suitable reporter molecules or labels, which may be used, include radionuclides, enzymes, fluorescent, chemiluminescent, or chromogenic agents as well as substrates, co-factors, inhibitors, magnetic particles, and the like.

Host cells transformed with nucleotide sequences encoding Mnk may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode Mnk may be designed to contain signal sequences, which direct secretion of Mnk through a prokaryotic or eukaryotic cell membrane. Other recombinant constructions may be used to join sequences encoding Mnk to nucleotide sequence encoding a polypeptide domain, which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.) The inclusion of cleavable linker sequences such as those specific for Factor XA or Enterokinase (Invitrogen, San Diego, Calif.) between the purification domain and Mnk may be used to facilitate purification. One such expression vector provides for expression of a fusion protein containing Mnk and a nucleic acid encoding 6 histidine residues preceding a Thioredoxin or an Enterokinase cleavage site. The histidine residues facilitate purification on IMIAC (immobilized metal ion affinity chromatography as described in Porath, J. et al. (1992, Prot. Exp. Purif. 3: 263-281)) while the Enterokinase cleavage site provides a means for purifying Mnk from the fusion protein. A discussion of vectors which contain fusion proteins is provided in Kroll, D. J. et al. (1993; DNA Cell Biol. 12:441-453). In addition to recombinant production, fragments of Mnk may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using Applied Biosystems 431 A peptide synthesized (Perkin Elmer). Various fragments of Mnk may be chemically synthesized separately and combined using chemical methods to produce the full length molecule.

Diagnostics and Therapeutics

The data disclosed in this invention show that the nucleic acids and proteins of the invention and effector molecules thereof are useful in diagnostic and therapeutic applications implicated, for example but not limited to, in metabolic disorders like obesity, diabetes, eating disorders, wasting syndromes (cachexia), pancreatic dysfunctions, arteriosclerosis, coronary artery disease (CAD), and other diseases and disorders as described above. Hence, diagnostic and therapeutic uses for the Mnk proteins of the invention are, for example but not limited to, the following: (i) protein therapeutic, (ii) small molecule drug target, (iii) antibody target (therapeutic, diagnostic, drug targeting/cytotoxic antibody), (iv) diagnostic and/or prognostic marker, (v) gene therapy (gene delivery/gene ablation), (vi) research tools, and (vii) tissue regeneration in vitro and in vivo (regeneration for all these tissues and cell types composing these tissues and cell types derived from these tissues).

The nucleic acids and proteins of the invention are useful in diagnostic and therapeutic applications implicated in various diseases and disorders described above and/or other pathologies and disorders. For example, but not limited to, cDNAs encoding the Mnk proteins of the invention and particularly their human homologues may be useful in gene therapy, and the Mnk proteins of the invention and particularly their human homologues may be useful when administered to a subject in need thereof. By way of non-limiting example, the compositions of the present invention will have efficacy for treatment of patients suffering from, for example, but not limited to, in metabolic disorders like obesity, diabetes, eating disorders, wasting syndromes (cachexia), pancreatic dysfunctions, arteriosclerosis, coronary artery disease (CAD), and other diseases and disorders, particularly as described above.

The nucleic acid(s) encoding the Mnk protein(s) of the invention, or fragments thereof, may further be useful in diagnostic applications, wherein the presence or amount of the nucleic acids or the proteins are to be assessed. These materials are further useful in the generation of antibodies that bind immunospecifically to the novel substances of the invention for use in therapeutic or diagnostic methods.

For example, in one aspect, antibodies which are specific for Mnk may be used directly as an antagonist, or indirectly as a targeting or delivery mechanism for bringing a pharmaceutical agent to cells or tissue which express Mnk. The antibodies may be generated using methods that are well known in the art. Such antibodies may include, but are not limited to, polyclonal, monoclonal, chimerical, single chain, Fab fragments, and fragments produced by a Fab expression library. Neutralising antibodies, (i.e., those which inhibit dimer formation) are especially preferred for therapeutic use.

For the production of antibodies, various hosts including goats, rabbits, rats, mice, humans, and others, may be immunised by injection with Mnk any fragment or oligopeptide thereof which has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Among adjuvants used in human, BCG (Bacille Calmette-Guerin) and *Corynebacterium parvum* are especially preferable. It is preferred that the peptides, fragments, or oligopeptides used to induce antibodies to Mnk have an amino acid sequence consisting of at least five amino acids, and more preferably at least 10 amino acids. It is preferable that they are identical to a portion of the amino acid sequence of the natural protein, and they may contain the entire amino acid sequence of a small, naturally occurring molecule. Short stretches of Mnk amino acids may be fused with those of another protein such as keyhole limpet hemocyanin and antibody produced against the chimeric molecule.

Monoclonal antibodies to Mnk may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. Proc. Natl. Acad. Sci. 80:2026-2030; Cole, S. P. et al. (1984) Mol. Cell. Biol. 62:109-120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851-6855; Neuberger, M. S. et al (1984) Nature 312:604-608; Takeda, S. et al. (1985) Nature 314:452-454). Alternatively, techniques described for the production of single chain antibodies may be adapted, using methods known in the art, to produce Mnk-specific single chain antibodies. Antibodies with related specificity, but of distinct idiotypic composition, may be generated by chain shuffling from random combinatorial immunoglobulin libraries (Burton, D. R. (1991) Proc. Natl. Acad. Sci. 88:11120-3). Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

Antibody fragments, which contain specific binding sites for Mnk, may also be generated. For example, such fragments include, but are not limited to proteolytic fragments, e.g. the F(ab')$_2$ fragments which can be produced by Pepsin digestion of the antibody molecule and the Fab fragments which can be generated by reducing the disulfide bridges of F(ab')$_2$ fragments. Alternatively, recombinant fragments may be generated. For example, Fab expression libraries may be constructed to allow rapid and easy identification of monoclonal Fab fragments with the desired specificity (Huse, W. D. et al. (1989) Science 254:1275-1281).

Various immunoassays may be used for screening to identify antibodies having the desired specificity. Numerous protocols for competitive binding and immunoradiometric assays using either polyclonal or monoclonal antibodies with established specificities are well known in the art. Such immunoassays typically involve the measurement of complex formation between Mnk and its specific antibody. A two-site, monoclonal-based immunoassay utilizing monoclonal antibodies reactive to two non-interfering Mnk epitopes is preferred, but a competitive binding assay may also be employed (Maddox, supra).

In another embodiment of the invention, the Mnk polynucleotides or any fragment thereof, or nucleic acid effector molecules, aptamers, anti-sense molecules, ribozymes or RNAi molecules, may be used for therapeutic purposes. In one aspect, aptamers, i.e. nucleic acid molecules, which are capable of binding to a Mnk protein and modulating its activity, may be generated by a screening and selection procedure involving the use of combinational nucleic acid libraries.

In a further aspect, antisense molecules to the polynucleotide encoding Mnk may be used in situations in which it would be desirable to block the transcription of the mRNA. In particular, cells may be transformed with sequences complementary to polynucleotides encoding Mnk. Thus, antisense molecules may be used to modulate Mnk activity, or to achieve regulation of gene function. Such technology is now well known in the art, and sense or antisense oligomers or larger fragments, can be designed from various locations along the coding or control regions of sequences encoding Mnk. Expression vectors derived from retroviruses, adenovirus, herpes or vaccinia viruses, or from various bacterial plasmids may be used for delivery of nucleotide sequences to the targeted organ, tissue or cell population. Methods, which are well known to those skilled in the art, can be used to construct recombinant vectors, which will express antisense molecules complementary to the polynucleotides of the gene encoding Mnk. These techniques are described both in Sambrook et al. (supra) and in Ausubel et al. supra). Genes encoding Mnk can be turned off by transforming a cell or tissue with expression vectors which express high levels of polynucleotide or fragment thereof which encodes Mnk. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, e.g. DNA, RNA, or nucleic acid analogues such as PNA, to the control regions of the gene encoding Mnk, i.e., the promoters, enhancers, and introns. Oligonucleotides derived from the transcription initiation site, e.g., between positions –10 and +10 from the start site, are preferred. Similarly, inhibition can be achieved using "triple helix" base-pairing methodology. Triple helix pairing is useful because it cause inhibition of the ability of the double helix to open sufficiently for the binding of polymerases, transcription factors, or regulatory molecules. Recent therapeutic advances using triplex DNA have been described in the literature (Gee, J. E. et al. (1994) In; Huber, B. E. and B. I. Carr, Molecular and Immunologic Approaches, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples, which may be used, include engineered hammerhead motif ribozyme molecules that can be specifically and efficiently catalyze endonucleolytic cleavage of sequences encoding Mnk. Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Effector molecules, e.g. antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding Mnk. Such DNA sequences may be incorporated into a variety of vectors with suitable RNA polymerase promoters such as T7 or SP6. Alternatively, these cDNA constructs that synthesize antisense RNA constitutively or inducibly can be introduced into cell lines, cells, or tissues. RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

The activity of Mnk proteins can be assayed for example by in vitro kinase assays, as described by Tschopp et al., 2000, supra or any other suitable assay principle as described below. As inhibitor of Mnk in this assay, a staurosporine derivative such as CGP57380 or CGP052088 can be used, as described by Tschopp et al., 2000, supra or Knauf et al., 2001, supra. As negative control, the compound CGP52428 which is inactive against Mnk, but displays a similar cytotoxicity as CGP052088, or any other chemical entities with kinase inhibitory activity with exception of activity against Mnk may be used. Moreover, derivatives of CGP57380 can be assayed for activity against Mnk and are substances for the treatment, prophylaxis, and diagnosis of metabolic diseases as mentioned above. Derivatives of CGP57380 could for example be generated by modification through conventional chemical, physical and biochemical means, and may be used to produce combinatorial libraries. They may be subjected to directed or random chemical modifications, such as acylation, alkylation, esterification, amidification, etc. to produce structural analogs.

Further, the invention relates to the use of Mnk kinase inhibitors or activators for the treatment, prophylaxis or diagnosis of metabolic diseases as mentioned above. Preferably, but not exclusively, the Mnk kinase inhibitors are staurosporine or pyrazole derivatives. Examples of pyrazole derivatives are described in EP-A-0 819 129 which is herein incorporated by reference. Since CGP57380 is not cytotoxic up to 30 μM, this substance may be preferably used to inhibit kinase activity, preferably Mnk2, and used as substance for the treatment, prophylaxis, and diagnosis of metabolic diseases as mentioned above.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods, which are well known in the art. Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of Mnk, antibodies to Mnk, mimetics, agonists, antagonists, or inhibitors of Mnk. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones. The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries, which facilitate processing of the active compounds into preparations which, can be used pharmaceutically. Further details on techniques for formulation and administration may be found in the latest edition of Remington's Pharmaceutical Sciences (Maack Publishing Co., Easton, Pa.). Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilising processes. The pharmaceutical composition may be provided as a salt and can be formed with many acids, including but not limited to, hydrochloric, sulphuric, acetic, lactic, tartaric, malic, succinic, etc. After pharmaceutical compositions have been prepared, they can be placed in an appropriate container and labelled for treatment of an indicated condition. For administration of Mnk, such labelling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art. For any compounds, the therapeutically effective does can be estimated initially either in cell culture assays, e.g., of preadipocyte cell lines, or in animal models, usually mice, rabbits, dogs, or pigs. The animal model may also be used to determine the appropriate concentration range and route of administration. Such information can then be used to determine useful doses and routes for administration in humans. A therapeutically effective dose refers to that amount of active ingredient, for example Mnk fragments thereof, antibodies of Mnk, to treat a specific condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage from employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art employ different formulations for nucleotides than for proteins or their inhibitors. Similarly, delivery of polynucleotides or polypeptides will be specific to particular cells, conditions, locations, etc.

In another embodiment, antibodies which specifically bind Mnk may be used for the diagnosis of conditions or diseases characterized by or associated with over- or underexpression of Mnk, or in assays to monitor patients being treated with Mnk, agonists, antagonists or inhibitors. The antibodies useful for diagnostic purposes may be prepared in the same manner as those described above for therapeutics. Diagnostic assays for Mnk include methods, which utilize the antibody and a label to detect Mnk in human body fluids or extracts of cells or tissues. The antibodies may be used with or without modification, and may be labelled by joining them, either covalently or non-covalently, with a reporter molecule. A wide variety of reporter molecules, which are known in the art may be used several of which are described above.

A variety of protocols including ELISA, RIA, and FACS for measuring Mnk are known in the art and provide a basis for diagnosing altered or abnormal levels of Mnk expression. Normal or standard values for Mnk expression are established by combining body fluids or cell extracts taken from normal mammalian subjects, preferably human, with antibody to Mnk under conditions suitable for complex formation. The amount of standard complex formation may be quantified by various methods, but preferably by photometric, means. Quantities of Mnk expressed in control and disease samples e.g. from biopsied tissues are compared with the standard values. Deviation between standard and subject values establishes the parameters for diagnosing disease. Analysis of Mnk expression can also be performed by determination of Mnk activity in assay formats well known in the art and described in more detail below.

In another embodiment of the invention, the polynucleotides specific for Mnk may be used for diagnostic purposes. The polynucleotides, which may be used, include oligonucleotide sequences, antisense RNA and DNA molecules, and PNAs. The polynucleotides may be used to detect and quantitate gene expression in biopsied tissues in which expression of Mnk may be correlated with disease. The diagnostic assay may be used to distinguish between absence, presence, and excess expression of Mnk, and to monitor regulation of Mnk levels during therapeutic intervention.

In one aspect, hybridization with PCR probes which are capable of detecting polynucleotide sequences, including genomic sequences, encoding Mnk and/or closely related molecules, may be used to identify nucleic acid sequences which encode Mnk. The specificity of the probe, whether it is made from a highly specific region, e.g., unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding Mnk, alleles, or related sequences. Probes may also be used for the detection of related sequences, and should preferably contain at least 50% of the nucleotides from any of the Mnk encoding sequences. The hybridization probes of the subject invention may be DNA or RNA and derived from the nucleotide sequence of AF237775 (SEQ ID NO.: 1), NM_017572.2 (SEQ ID NO.: 55), NM_003684.2 (SEQ ID NO.: 5), or AB000409.1 (SEQ ID NO.: 56) or from a genomic sequence including promoter, enhancer elements, and introns of the naturally occurring Mnk. Means for producing specific hybridization probes for DNAs encoding Mnk include the cloning of nucleic acid sequences encoding Mnk derivatives into vectors for the production of mRNA probes. Such vectors are known in the art, commercially available, and may be used to synthesize RNA probes in vitro by means of the addition of the appropriate RNA polymerases and the appropriate labelled nucleotides. Hybridization probes may be labelled by a variety of reporter groups, for example, radionuclides such as $^{32}P$ or $^{35}S$, or enzymatic labels, such as alkaline phosphatase coupled to the probe via avidin/biotin coupling systems, and the like. Polynucleotide sequences encoding Mnk may be used for the diagnosis of conditions or diseases, which are associated with expression of Mnk. Examples of such conditions or diseases include, but are not limited to, pancreatic diseases and disorders, including diabetes.

Polynucleotide sequences encoding Mnk may also be used to monitor the progress of patients receiving treatment for pancreatic diseases and disorders, including diabetes. The polynucleotide sequences encoding Mnk may be used in Southern or Northern analysis, dot blot, or other membrane-based technologies; in PCR technologies; or in dip stick, pin, ELISA or chip assays utilizing fluids or tissues from patient biopsies to detect altered Mnk expression. Such qualitative or quantitative methods are well known in the art.

In a particular aspect, the nucleotide sequences encoding Mnk may be useful in assays that detect activation or induction of various metabolic diseases and disorders, including obesity, diabetes, eating disorders, wasting syndromes (cachexia), pancreatic dysfunctions, arteriosclerosis, coronary artery disease (CAD), disorders related to ROS production, and neurodegenerative diseases. The nucleotide sequences encoding Mnk may be labelled by standard methods, and added to a fluid or tissue sample from a patient under conditions suitable for the formation of hybridization complexes. After a suitable incubation period, the sample is washed and the signal is quantitated and compared with a standard value. The presence of altered levels of nucleotide sequences encoding Mnk in the sample compared to a control sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of Mnk, a normal or standard profile for expression is established. This may be accomplished by combining body fluids or cell extracts taken from normal subjects, either animal or human, with a sequence, or a fragment thereof, which encodes Mnk, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease. Once disease is established and a treatment protocol is initiated, hybridization assays may be repeated on a regular basis to evaluate whether the level of expression in the patient begins to approximate that, which is observed in the normal patient. The results obtained from successive assays may be used to show the efficacy of treatment over a period ranging from several days to months.

With respect to metabolic diseases and disorders, including obesity, diabetes, eating disorders, wasting syndromes (cachexia), pancreatic dysfunctions, arteriosclerosis, coronary artery disease (CAD), disorders related to ROS production, and neurodegenerative diseases presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the pancreatic diseases and disorders. Additional diagnostic uses for oligonucleotides designed from the sequences encoding Mnk may involve the use of PCR. Such oligomers may be chemically synthesized, generated enzymatically, or produced from a recombinant source. Oligomers will preferably consist of two nucleotide sequences, one with sense orientation (5'.fwdarw.3') and another with antisense (3'.rarw.5'), employed under optimized conditions for identification of a specific gene or condition. The same two oligomers, nested sets of oligomers, or even a degenerate pool of oligomers may be employed under less stringent conditions for detection and/or quantification of closely related DNA or RNA sequences.

Methods which may also be used to quantitate the expression of Mnk include radiolabelling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 212:229-236). The speed of quantification of multiple samples may be accelerated by running the assay in an ELISA format where the oligomer of interest is presented in various dilutions and a spectrophotometric or colorimetric response gives rapid quantification.

In another embodiment of the invention, the nucleic acid Mnk sequences may also be used to generate hybridization probes, which are useful for mapping the naturally occurring genomic sequence. The sequences may be mapped to a particular chromosome or to a specific region of the chromosome using well known techniques. Such techniques include FISH, FAGS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127-134, and Trask, B. J. (1991) Trends Genet. 7:149-154. FISH (as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding Mnk on a physical chromosomal map and a specific disease, or predisposition to a specific disease, may help to delimit the region of DNA associated with that genetic disease.

The nucleotide sequences of the subject invention may be used to detect differences in gene sequences between normal, carrier or affected individuals. In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577-580), any sequences mapping to that area may represent associated or regulatory genes for further investigation. The nucleotide sequences of the subject invention may also be used to detect differences in the chromosomal location due to translocation, inversion, etc. among normal, carrier or affected individuals.

In another embodiment of the invention, the proteins of the invention, its catalytic or immunogenic fragments or oligopeptides thereof, an in vitro model, a genetically altered cell or animal, can be used for screening libraries of compounds in any of a variety of drug screening techniques. One can identify effectors, e.g. receptors, enzymes, proteins, peptides, ligands or substrates that bind to, modulate or mimic the action of one or more of the proteins of the invention. The protein or fragment thereof employed in such screening may be free in solution, affixed to a solid support, borne on a cell surface, or located intracellularly. The formation of binding complexes, between the proteins of the invention and the agent tested, may be measured. Agents could also, either directly or indirectly, influence the activity of the proteins of the invention. Target mechanisms can for example include a kinase activity, particularly the phosphorylation of proteins or peptides, most preferably, but not limited to serine and threonine residues. Another target mechanism could include the regulation of Mnk function by posttranslational modifications such as phosphorylation, dephosphorylation, acetylation, alkylation, ubiquitination, proteolytic processing subcellular localization or degradation. Yet another target mechanism could include the interaction of Mnk with protein binding partners such as, but not limited to, phospholipase A, estrogen receptors, kinases or translation factors. Of particular interest are screening assays for agents that have a low toxicity for mammalian cells. The term "agent" as used herein describes any molecule, e.g. protein or pharmaceutical, with the capability of altering or mimicking the physiological function of one or more of the proteins of the invention. Candidate agents encompass numerous chemical classes, though typically they are organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise carbocyclic or heterocyclic structures and/or aromatic or polyaromatic structures substituted with one or more of the above functional groups.

Candidate agents are also found among biomolecules including peptides, saccharides, fatty acids, steroids, purines, pyrimidines, nucleic acids and derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Where the screening assay is a binding assay, one or more of the molecules may be joined to a label, where the label can directly or indirectly provide a detectable signal.

Another technique for drug screening, which may be used, provides for high throughput screening of compounds having suitable binding affinity to the protein of interest as described in published PCT application WO84/03564. In this method, as applied to the proteins of the invention large numbers of different small test compounds, e.g. aptamers, peptides, low-molecular weight compounds etc., are provided or synthesized on a solid substrate, such as plastic pins or some other surface. The test compounds are reacted with the proteins or fragments thereof, and washed. Bound proteins are then detected by methods well known in the art. Purified proteins can also be coated directly onto plates for use in the aforementioned drug screening techniques. Alternatively, non-neutralizing antibodies can be used to capture the peptide and immobilize it on a solid support. In another embodiment, one may use competitive drug screening assays in which neutralizing antibodies capable of binding the protein specifically compete with a test compound for binding the protein. In this manner, the antibodies can be used to detect the presence of any peptide, which shares one or more antigenic determinants with the protein.

Candidate agents may also be found in kinase assays where a kinase substrate such as a protein or a peptide, which may or may not include modifications as further described below, or others are phosphorylated by the proteins or protein fragments of the invention. A therapeutic candidate agent may be identified by its ability to increase or decrease the enzymatic activity of the proteins of the invention. The kinase activity may be detected by change of the chemical, physical or immunological properties of the substrate due to phosphorylation.

One example could be the transfer of radioisotopically labelled phosphate groups from an appropriate donor molecule to the kinase substrate catalyzed by the polypeptides of the invention. The phosphorylation of the substrate may be followed by detection of the substrates autoradiography with techniques well known in the art.

Yet in another example, the change of mass of the substrate due to its phosphorylation may be detected by mass spectrometry techniques.

One could also detect the phosphorylation status of a substrate with a reagent discriminating between the phosphorylated and unphosphorylated status of the substrate. Such a reagent may act by having different affinities for the phosphorylated and unphosphorylated forms of the substrate or by having specific affinity for phosphate groups. Such a reagent could be, but is not limited to, an antibody or antibody derivative, a recombinant antibody-like structure, a protein, a nucleic acid, a molecule containing a complexed metal ion, an anion exchange chromatography matrix, an affinity chromatography matrix or any other molecule with phosphorylation dependent selectivity towards the substrate.

Such a reagent could be employed to detect the kinase substrate, which is immobilized on a solid support during or after an enzymatic reaction. If the reagent is an antibody, its binding to the substrate could be detected by a variety of techniques as they are described in Harlow and Lane, 1998, Antibodies, CSH Lab Press, NY. If the reagent molecule is not an antibody, it may be detected by virtue of its chemical, physical or immunological properties, being endogenously associated with it or engineered to it.

Yet in another example the kinase substrate may have features, designed or endogenous, to facilitate its binding or detection in order to generate a signal that is suitable for the analysis of the substrates phosphorylation status. These features may be, but are not limited to, a biotin molecule or derivative thereof, a glutathione-S-transferase moiety, a moiety of six or more consecutive histidine residues, an amino acid sequence or hapten to function as an epitope tag, a fluorochrome, an enzyme or enzyme fragment. The kinase substrate may be linked to these or other features with a molecular spacer arm to avoid steric hindrance.

In one example the kinase substrate may be labelled with a fluorophore. The binding of the reagent to the labelled substrate in solution may be followed by the technique of fluorescence polarization as it is described in the literature (see, for example, Deshpande, S. et al. (1999) Prog. Biomed. Optics (SPIE) 3603:261; Parker, G. J. et al. (2000) J. Biomol. Screen. 5:77-88; Wu, P. et al. (1997) Anal. Biochem. 249:29-36). In a variation of this example, a fluorescent tracer molecule may compete with the substrate for the analyte to detect kinase activity by a technique which is known to those skilled in the art as indirect fluorescence polarization.

The nucleic acids encoding the proteins of the invention can be used to generate transgenic cell lines and animals. These transgenic animals are useful in the study of the function and regulation of the proteins of the invention in vivo. Transgenic animals, particularly mammalian transgenic animals, can serve as a model system for the investigation of many developmental and cellular processes common to humans. Transgenic animals may be made through homologous recombination in embryonic stem cells, where the normal locus of the gene encoding the protein of the invention is mutated. Alternatively, a nucleic acid construct encoding the protein is injected into oocytes and is randomly integrated into the genome. One may also express the genes of the invention or variants thereof in tissues where they are not normally expressed or at abnormal times of development. Furthermore, variants of the genes of the invention like specific constructs expressing anti-sense molecules or expression of dominant negative mutations, which will block or alter the expression of the proteins of the invention may be randomly integrated into the genome. A detectable marker, such as lac Z or luciferase may be introduced into the locus of the genes of the invention, where upregulation of expression of the genes of the invention will result in an easily detectable change in phenotype. Vectors for stable integration include plasmids, retroviruses and other animal viruses, yeast artificial chromosomes (YACs), and the like. DNA constructs for homologous recombination will contain at least portions of the genes of the invention with the desired genetic modification, and will include regions of homology to the target locus. Conveniently, markers for positive and negative selection are included. DNA constructs for random integration do not need to contain regions of homology to mediate recombination. DNA constructs for random integration will consist of the nucleic acids encoding the proteins of the invention, a regulatory element (promoter), an intron and a poly-adenylation signal. Methods for generating cells having targeted gene modifications through homologous recombination are known in the field. For embryonic stem (ES) cells, an ES cell line may be employed, or embryonic cells may be obtained freshly from a host, e.g. mouse, rat, guinea pig, etc. Such cells are grown on an appropriate fibroblast-feeder layer and are grown in the presence of leukemia inhibiting factor (LIF). ES or embryonic cells may be transfected and can then be used to produce transgenic animals. After transfection, the ES cells are plated onto a feeder layer in an appropriate medium. Cells containing the construct may be selected by employing a selection medium. After sufficient time for colonies to grow, they are picked and analyzed for the occurrence of homologous recombination. Colonies that are positive may then be used for embryo manipulation and morula aggregation. Briefly, morulae are obtained from 4 to 6 week old superovulated females, the Zona Pellucida is removed and the morulae are put into small depressions of a tissue culture dish. The ES cells are trypsinized, and the modified cells are placed into the depression closely to the morulae. On the following day the aggregates are transferred into the uterine horns of pseudopregnant females. Females are then allowed to go to term. Chimeric offsprings can be readily detected by a change in coat color and are subsequently screened for the transmission of the mutation into the next generation (F1-generation). Offspring of the F1-generation are screened for the presence of the modified gene and males and females having the modification are mated to produce homozygous progeny. If the gene alterations cause lethality at some point in development, tissues or organs can be maintained as allogenic or congenic grafts or transplants, or in vitro culture. The transgenic 3o animals may be any non-human mammal, such as laboratory animal, domestic animals, etc., for example, mouse, rat, guinea pig, sheep, cow, pig, and others. The transgenic animals may be used in functional studies, drug screening, and other applications and are useful in the study of the function and regulation of the proteins of the invention in vivo.

Finally, the invention also relates to a kit comprising at least one of (a) a Mnk2 (Mnk2a or Mnk2b) or Mnk1 nucleic acid molecule or a fragment thereof;
(b) a vector comprising the nucleic acid of (a);
(c) a host cell comprising the nucleic acid of (a) or the vector of (b);
(d) a polypeptide encoded by the nucleic acid of (a);
(e) a fusion polypeptide encoded by the nucleic acid of (a);
(f) an antibody, an aptamer or another receptor against the nucleic acid of (a) or the polypeptide of (d) or (e) and
(g) an anti-sense oligonucleotide of the nucleic acid of (a).

The kit may be used for diagnostic or therapeutic purposes or for screening applications as described above. The kit may further contain user instructions.

The Examples illustrate the invention:

EXAMPLE 1

Measurement of Triglyceride Content of Homozygous Flies (FIG. 1)

The change of triglyceride content of Drosophila melanogaster containing a special expression system (EP-element, Rorth P, Proc Natl Acad Sci USA 1996, 93(22): 12418-22) was measured. Mutant flies are obtained from a fly mutation stock collection. The flies are grown under standard conditions known to those skilled in the art, and in the course of the experiment, additional feedings with bakers yeast (Saccharomyces cerevisiae) are provided. Specifically, homozygous male EP(3)3333 and EP(3)3576 flies were investigated in comparison to control flies (FIG. 1). For determination of triglyceride content, flies were incubated for 5 min at gooc in an aqueous buffer using a waterbath, followed by hot extraction. After another 5 min incubation at 90° C. and mild centrifugation, the triglyceride content of the flies extract was determined using Sigma Triglyceride (I NT 336-10 or -20) assay by measuring changes in the optical density according to the manufacturer's protocol. As a reference protein content of the same extract was measured using BIO-RAD DC Protein Assay according to the manufacturer's protocol. The assay was repeated several times. The average triglyceride level of EP collection is shown as 100% in FIG. 1. EP(3)3333 and EP(3)3576 homozygous flies show constantly a higher triglyceride content than the controls (approx. 140%). Therefore, the change of gene activity in the locus 86F7 (estimated), where the EP-vector of EP(3)3333 and EP(3)3576 flies is homozygous viably integrated into the Lk6 gene locus, is responsible for changes in the metabolism of the energy storage triglycerides, therefore representing in both cases an obese fly model.

EXAMPLE 2

Identification of the Drosophila Gene Responsible for the Change in the Metabolism of the Energy Storage Triglycerides (FIG. 2)

Genomic DNA sequences were isolated that are localized directly adjacent to the integration of the EP vectors (herein EP(3)3333 and EP(3)3576). Using those isolated genomic sequences, public databases like Berkeley Drosophila Genome Project (GadFly) were screened thereby confirming the homozygous viable integration site of the EP(3)3333 and EP(3)3576 vectors. FIG. 2 shows the molecular organization of this gene locus. In FIG. 2, genomic DNA sequence is represented by the assembly as a dotted black line (from position 7544500 to 7559500 on chromosome 3R) that includes the integration sites of EP(3)3333 and EP(3)3576. Transcribed DNA sequences (expressed sequence tags, ESTs) and predicted exons are shown as bars in the lower two lines. Predicted exons of gene CG17342 (GadFly, Lk6, homologous to Mnk) are shown as dark grey bars and introns are shown as slim grey lines in the middle of the figure. Using plasmid rescue method genomic DNA sequences that are directly localised 3' of the EP(3)3333 and EP(3)3576 integration site were isolated. Using the plasmid rescue DNA public DNA sequence databases were screened thereby identifying the integration site of EP(3)3333 and EP(3)3576 causing an increase of triglyceride content. EP(3)3333 is integrated in the 5' region of a 5 prime exon of the gene CG17342 and EP(3)3576 in the 5' region of an alternative 5' exon. Mnk encodes for a gene that is predicted by GadFly sequence analysis programs as CG17342. Therefore, expression of the CG17342 could be affected by homozygous viable integration of the EP(3)3333 and EP(3)3576 leading to increase of the energy storage triglycerides and a change of uncoupling protein activity.

EXAMPLE 3

Cloning of a Drosophila melanogaster Gene with Homology to Human Uncoupling Proteins (UCPs) (FIG. 7)

Sequences homologous to human UCP2 and UCP3 genes were identified using the publicly available program BLAST of the data base of the National Center for Biotechnology Information (NCBI)(see, Altschul et al., 1997, Nucleic Acids Res. 25:3389-3402). The homology search yielded sequence fragments of a family of Drosophila genes with UCP homology. They are clearly different to the next related mitochondrial proteins (oxoglutarate carrier). Using the sequence fragment of one of this genes (herein referred to as dUCPy'), a PCR primer pair was generated (Upper 5'-CTAAACAAA-CAATTCCAAACATAG (SEQ ID NO.: 9), Lower 5 prime-AAAAGACATAGAAAATACGATAGT (SEQ ID NO.: 10)) and a PCR reaction performed on Drosophila cDNA using standard PCR conditions. The amplification product was radioactively labelled and used to screen a cDNA library prepared from adult Drosophila flies (Stratagene). A full-length cDNA clone was isolated, sequenced (FIG. 7), and used for further experiments. The nucleotide sequence of dUCPy is shown in FIG. 7A (SEQ ID NO.: 7), the deduced open reading is shown in FIG. 7B (SEQ ID NO.: 8).

EXAMPLE 4

Cloning of the dUCPy cDNA into an Drosophila Expression Vector

In order to test the effects of dUCPy expression in Drosophila cells, the dUCPy cDNA was cloned into the expression vector pUAST (Brand A & Perrimon N, Development 1993, 118:401-415) using the restriction sites Not I and Kpn I. The resulting expression construct was injected into the germline of *Drosophila embryos* and *Drosophila* strains with a stable integration of the construct were generated. Since the expression vector pUAST is activated by the yeast transcription factor Gal4 which is normally absent from *Drosophila* cells dUCPy is not yet expressed in these transgenic animals. If pUAST-dUCPy flies are crossed with a second *Drosophila* strain that expresses Gal4 in a tissue specific manner the offspring flies of this mating will express dUCPy in the Gal4 expressing tissue. The cross of pUAST-dUCPy flies with a strain that expresses Gal4 in all cells of the body (under control of the actin promoter) showed no viable offspring. This means that dUCPy overexpression in all body cells is lethal. This finding is consistent with the assumption that dUCPy overexpression could lead to a collapse of the cellular energy production. Expression of dUCPy in a non-vital organ like the eye (Gal4 under control of the eye-specific promoter of the "eyeless" gene) results in flies with visibly damaged eyes. This easily visible eye phenotype is the basis of a genetic screen for gene products that can modify UCP activity.

Figure 4:
FIG. 4 shows the eye phenotype induced by over-expression of the *Drosophila* UCP uncoupling protein homologue (dUCPy) that was used to discover factors modulating uncoupling protein activity. In the fly shown in the left part of the picture, dUCPy is expressed at normal levels. In the fly shown in the right part of the photograph, dUCPy is over-expressed, and the eye is reduced.

EXAMPLE 5 dUCPy Modifier Screen (FIG. 4)

Parts of the genomes of the strain with Gal4 expression in the eye and the strain carrying the pUAST-dUCPy construct were combined on one chromosome using genomic recombination. The resulting fly strain has eyes that are permanently damaged by dUCPy expression. Flies of this strain were crossed with flies of a large collection of mutagenized fly strains. In this mutant collection a special expression system (EP-element, see Rorth, 1996, supra) is integrated randomly in different genomic loci. The yeast transcription factor Gal4 can bind to the EP-element and activate the transcription of endogenous genes close the integration site of the EP-element. The activation of the genes therefore occurs in the same cells (eye) that overexpress dUCPy. Since the mutant collection contains several thousand strains with different integration sites of the EP-element it is possible to test a large number of genes whether their expression interacts with dUCPy activity. In case a gene acts as an enhancer of UCP activity the eye defect will be worsened; a suppressor will ameliorate the defect (see FIG. 4). Using this screen a gene with enhancing activity was discovered that was found to be the LK6 kinase in *Drosophila*.

EXAMPLE 6

Cloning of Lk6 from *Drosophila* (FIG. 3A)

Genomic DNA neighbouring to the eye-defect rescuing EP-element was cloned by inverse PCR and sequenced. This sequence was used for a BLAST search in a public *Drosophila* gene database. The amino acid sequence (SEQ ID NO.: 40) of the *Drosophila* protein is shown in FIG. 3A (referred to as dmAB18789).

EXAMPLE 7

Identification of Mammalian LK6 Homologous Proteins (FIG. 3)

Sequences homologous to *Drosophila* Lk6 were identified using the publicly available program BLASTP 2.2.3 of the non-redundant protein data base of the National Center for Biotechnology Information (NCBI)(see, Altschul et al., 1997, Nucleic Acids Res. 25:3389-3402). Mnk homologous proteins and nucleic acid molecules coding therefore are obtainable from insect or vertebrate species, e.g. mammals or birds. Particularly preferred are human Mnk homologous polypeptides and nucleic acids, particularly polypeptides and nucleic acids encoding a human Mnk2 protein (Genbank Accession No. AF237775 (SEQ ID NO.: 2) and NM_017572.1 (SEQ ID NO.: 4); Genbank Accession No. AF237775 (SEQ ID NO.: 2) is identical to formerly Genbank Accession No. XM_030637 which was removed at the submitters request; see a Clustal W multiple sequence alignment in FIG. 3B) or nucleic acids encoding a human Mnk1 protein (Genbank Accession No. AB000409.1 (SEQ ID NO.: 56) and NM_003684.2 (SEQ ID NO.: 59); Genbank Accession No. AB000409.1 (SEQ ID NO.: 56) is identical to formerly Genbank Accession No. XM_001600 which was removed at the submitters request; see a Clustal W multiple sequence alignment in FIG. 3C). FIG. 3A shows the alignment of the Mnk proteins from different species, hXP_030637 refers to human Mnk2 (identical to Genbank Accession No. AF237775 (SEQ ID NO.: 2)), hXP_001600 refers to human Mnk1 (identical to Genbank Accession No. AB000409.1 (SEQ ID NO.: 56)), and dmAB18789 refers to the protein having amino acid sequence SEQ ID NO.: 40 encoded by *Drosophila* gene with GadFly Accession No. CG17342. The mouse homologous polypeptides of the invention were identified as GenBank Accession Numbers NP_067437.1 (SEQ ID NO.: 85) (for the mouse homolog MAP kinase-interacting serine/threonine kinase 2; Mnk2; encoded by the cDNA having GenBank Accession Number BC010256 (SEQ ID NO.: 57)) and GenBank Accession Number NP_067436.1 (SEQ ID NO.: 86) (for the mouse homolog MAP kinase-interacting serine/threonine kinase 1; Mnk1).

EXAMPLE 8

Expression of the Polypeptides in Mammalian (Mouse) Tissues (FIG. 5 and FIG. 6)

For analyzing the expression of the polypeptides disclosed in this invention in mammalian tissues, several mouse strains (preferably mice strains C57Bl/6J, C57Bl/6 ob/ob and C57Bl/KS db/db which are standard model systems in obesity and diabetes research) were purchased from Harlan Winkelmann (33178 Borchen, Germany) and maintained under constant temperature (preferably 22° C.), 40 percent humidity and a light/dark cycle of preferably 14/10 hours. The mice were fed a standard chow (for example, from ssniff Spezialitaten GmbH, order number ssniff M-Z V1126-000). For the fasting experiment ("fasted wild type mice"), wild type mice were starved for 48 h without food, but only water supplied ad libitum. (see, for example, Schnetzler et al. J Clin Invest 1993 July; 92(1):272-80, Mizuno et al. Proc Natl Acad Sci USA 1996 Apr. 16; 93(8):3434-8). Animals were sacrificed at an age of 6 to 8 weeks. The animal tissues were isolated according to standard procedures known to those skilled in the art, snap frozen in liquid nitrogen and stored at −80° C. until needed. For analyzing the role of the proteins disclosed in this invention in the in vitro differentiation of different mammalian cell culture cells for the conversion of pre-adipocytes to adipocytes, mammalian fibroblast (3T3-L1) cells (e.g., Green & Kehinde, Cell 1: 113-116, 1974) were obtained from the American Tissue Culture Collection (ATCC, Hanassas, Va., USA; ATCC-CL 173). 3T3-L1 cells were maintained as fibroblasts and differentiated into adipocytes as described in the prior art (e.g., Qiu. et al., J. Biol. Chem. 276:11988-95, 2001; Slieker et al., BBRC 251: 225-9, 1998). In brief, cells were plated in DMEM/10% FCS (Invitrogen, Karlsruhe, Germany) at 50,000 cells/well in duplicates in 6-well plastic dishes and cultured in a humidified atmosphere of 5% $CO_2$ at 37° C. At confluence (defined as day 0: d0) cells were transferred to serum-free (SF) medium, containing DMEM/HamF12 (3:1; Invitrogen), Fetuin (300 µg/ml; Sigma, Munich, Germany), Transferrin (2 µg/ml; Sigma), Pantothenate (17 mM; Sigma), Biotin (1 $_m$M; Sigma), and EGF (0.8 nM; Hoffmann-La Roche, Basel, Switzerland). Differentiation was induced by adding Dexamethasone (DEX; 1 µM; Sigma), 3-Methyl-Isobutyi-1-Methylxanthine (MIX; 0.5 mM; Sigma), and bovine Insulin (5 µg/ml; Invitrogen). Four days after confluence (d4), cells were kept in SF medium, containing bovine Insulin (5 µg/ml) until differentiation was completed. At various time points of the differentiation procedure, beginning with day 0 (day of confluence) and day 2 (hormone addition; for example, dexamethason and 3-isobutyl-1-methylxanthin), up to 10 days of differentiation, suitable aliquots of cells were taken every two days. Alternatively, mammalian fibroblast 3T3-F442A cells (e.g., Green & Kehinde, Cell 7: 105-113, 1976) were obtained from the Harvard Medical School, Department of Cell Biology (Boston, Mass., USA). 3T3-F442A cells were maintained as fibroblasts and differentiated into adipocytes as described previously (Djian, P. et al., J. Cell. Physiol., 124: 554-556, 1985). At various time points of the differentiation procedure, beginning with day 0 (day of confluence and hormone addition, for example, Insulin), up to 10 days of differentiation, suitable aliquots of cells were taken every two days. 3T3-F442A cells are differentiating in vitro already in the confluent stage after hormone (insulin) addition. TaqMan Analysis of the proteins of the invention was carried out (FIG. 5 and FIG. 6). RNA was isolated from mouse tissues or cell culture cells using Trizol Reagent (for example, from Invitrogen, Karlsruhe, Germany) and further purified with the RNeasy Kit (for example, from Qiagen, Germany) in combination with an DNase-treatment according to the instructions of the manufacturers and as known to those skilled in the art. Total RNA was reverse transcribed (preferably using Superscript II RNaseH—Reverse Transcriptase, from Invitrogen, Karlsruhe, Germany) and subjected to Taqman analysis preferably using the Taqman 2×PCR Master Mix (from Applied Biosystems, Weiterstadt, Germany; the Mix contains according to the Manufacturer for example AmpliTaq Gold DNA Polymerase, AmpErase UNG, dNTPs with dUTP, passive reference Rox and optimized buffer components) on a GeneAmp 5700 Sequence Detection System (from Applied Biosystems, Weiterstadt, Germany).

For the analysis of the expression of Mnk2 or Mnk1, taqman analysis was performed using the following primer/probe pairs:

```
Mouse Mnk1 forward primer (SEQ ID NO.: 11)
5'-GCT GAG GGC CTC TGC TCC-3';

Mouse Mnk1 reverse primer (SEQ ID NO.: 12)
5'-TCG CCT TCG AGC GAG G-3';

Mouse Mnk1 Taqman probe (SEQ ID NO.: 13)
(5/6-FAM) TGAAGCTGTCCCCTCCATCCAAATCTC (5/6-TAMRA)

Taqman-1856F Mnk2 forward primer (SEQ ID NO.: 14):
5'-TGCACTTGATTGACCCCGA-3'

Taqman-1923R Mnk2 reverse primer (SEQ ID NO.: 15):
5'-TTTCTGATTGTCAACCCTCCAA-3'

Taqman-1877T Mnk2 Taqman probe (SEQ ID NO.: 16):
(5/6-FAM)-CCCCATCATCCACCTGCAGTGTCC-(5/6-TAMRA)
```

Figure 5A:
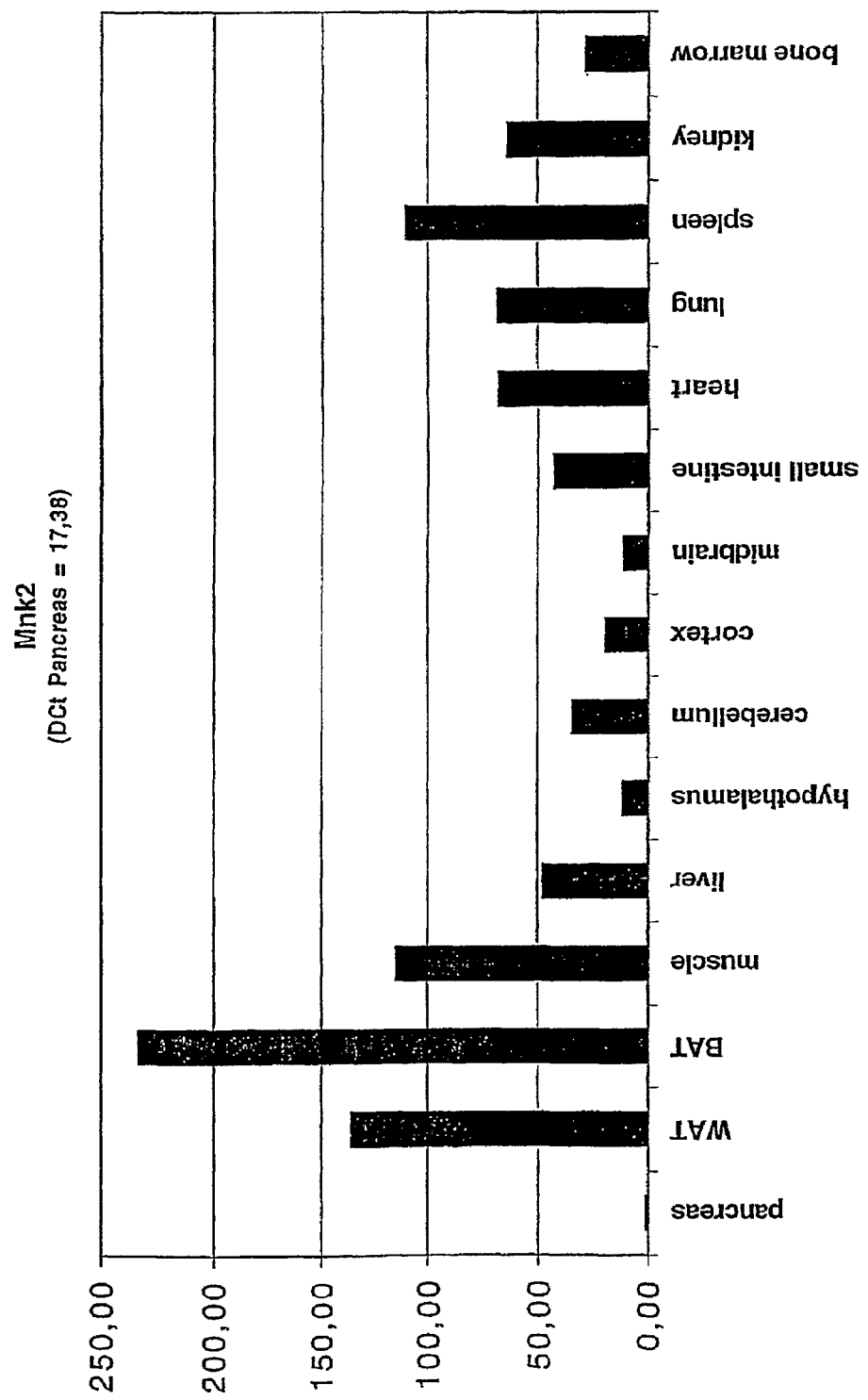
FIGS. 5A and 5B show the expression of the Mnk2 gene.
Figure 5B:
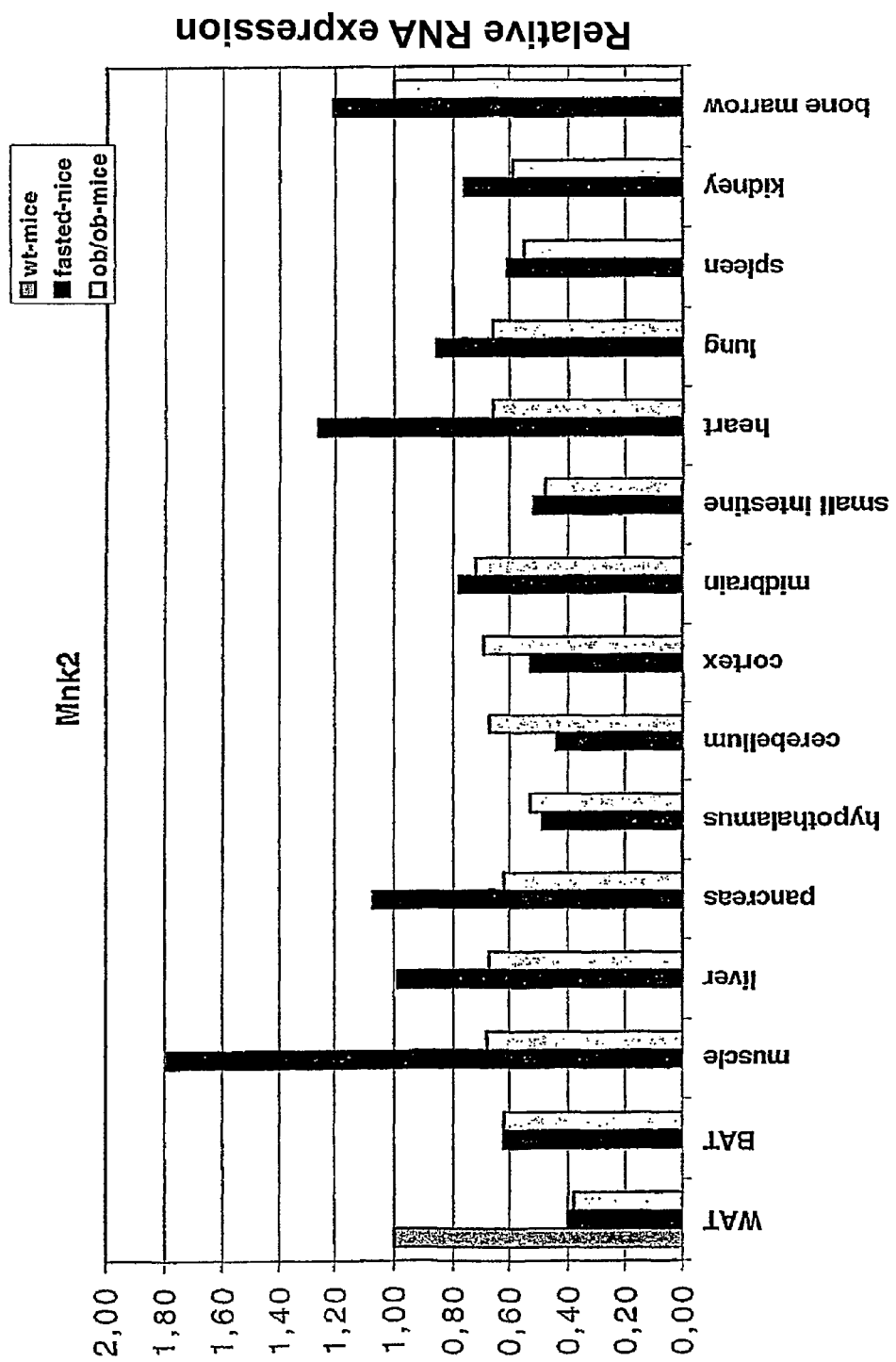
Figure 5C:
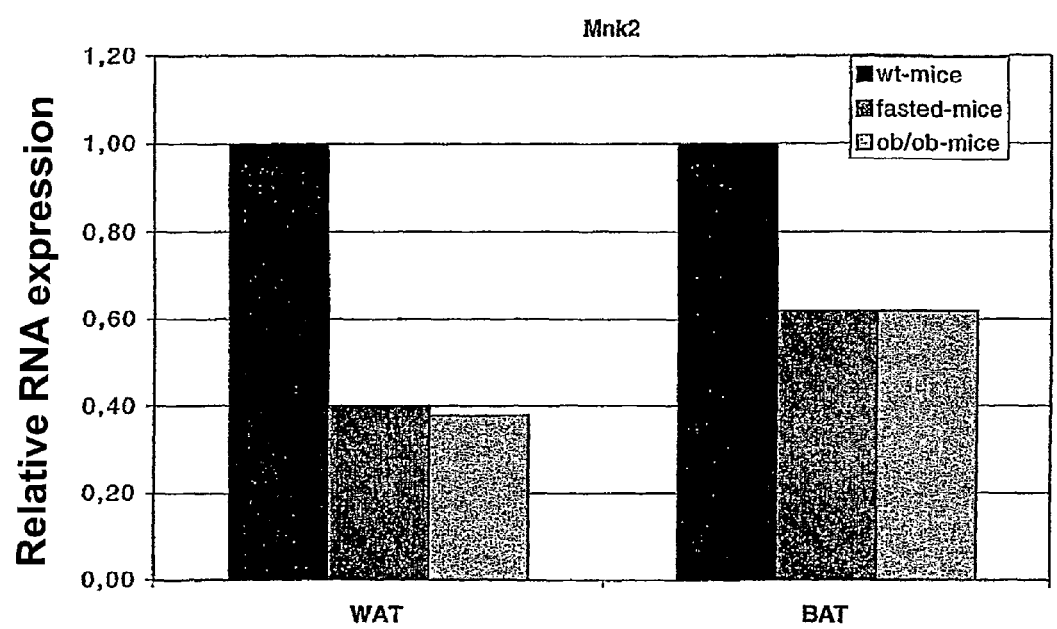
FIG. 5C shows the expression of mouse Mnk2 gene in adipose tissue of fasted and obese mice strains.
Figure 5D:
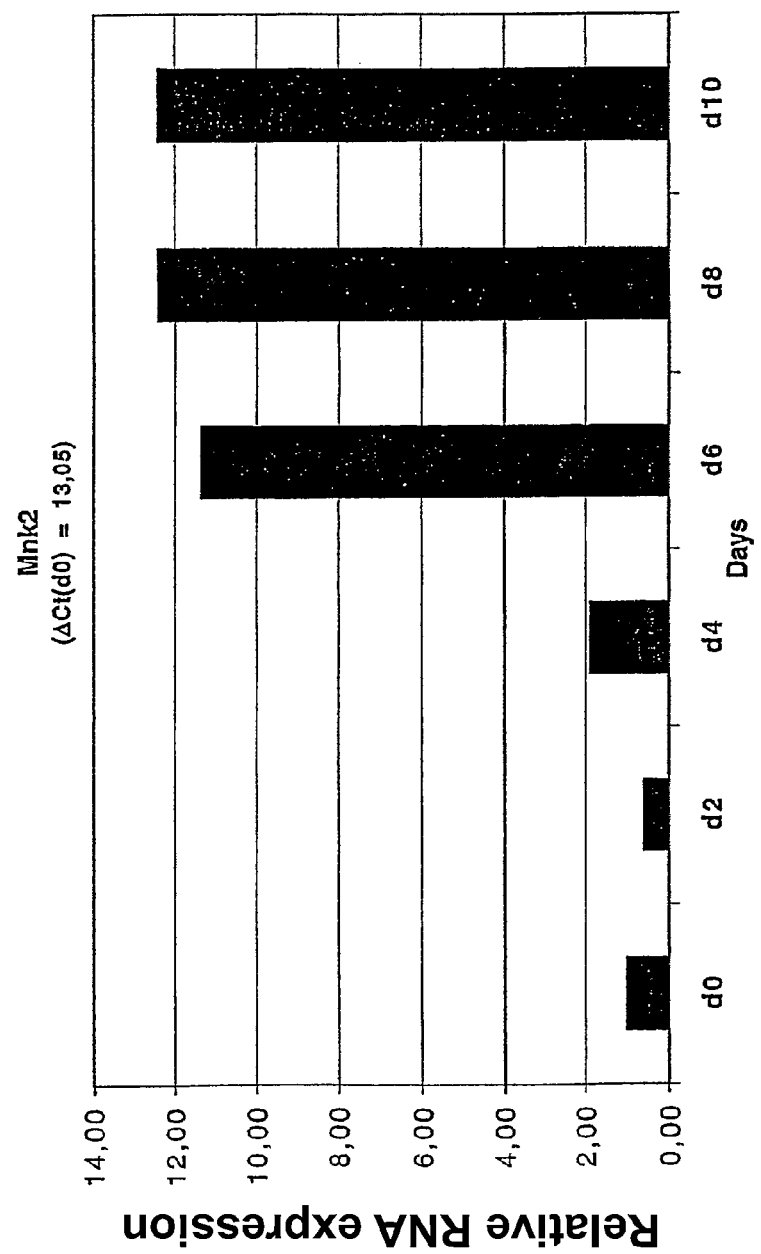
FIG. 5D shows the real-time PCR mediated comparison of Mnk2 expression during differentiation of mammalian fibroblast (3T3-L1) cells from pre-adipocytes to mature adipocytes.
Figure 5E:
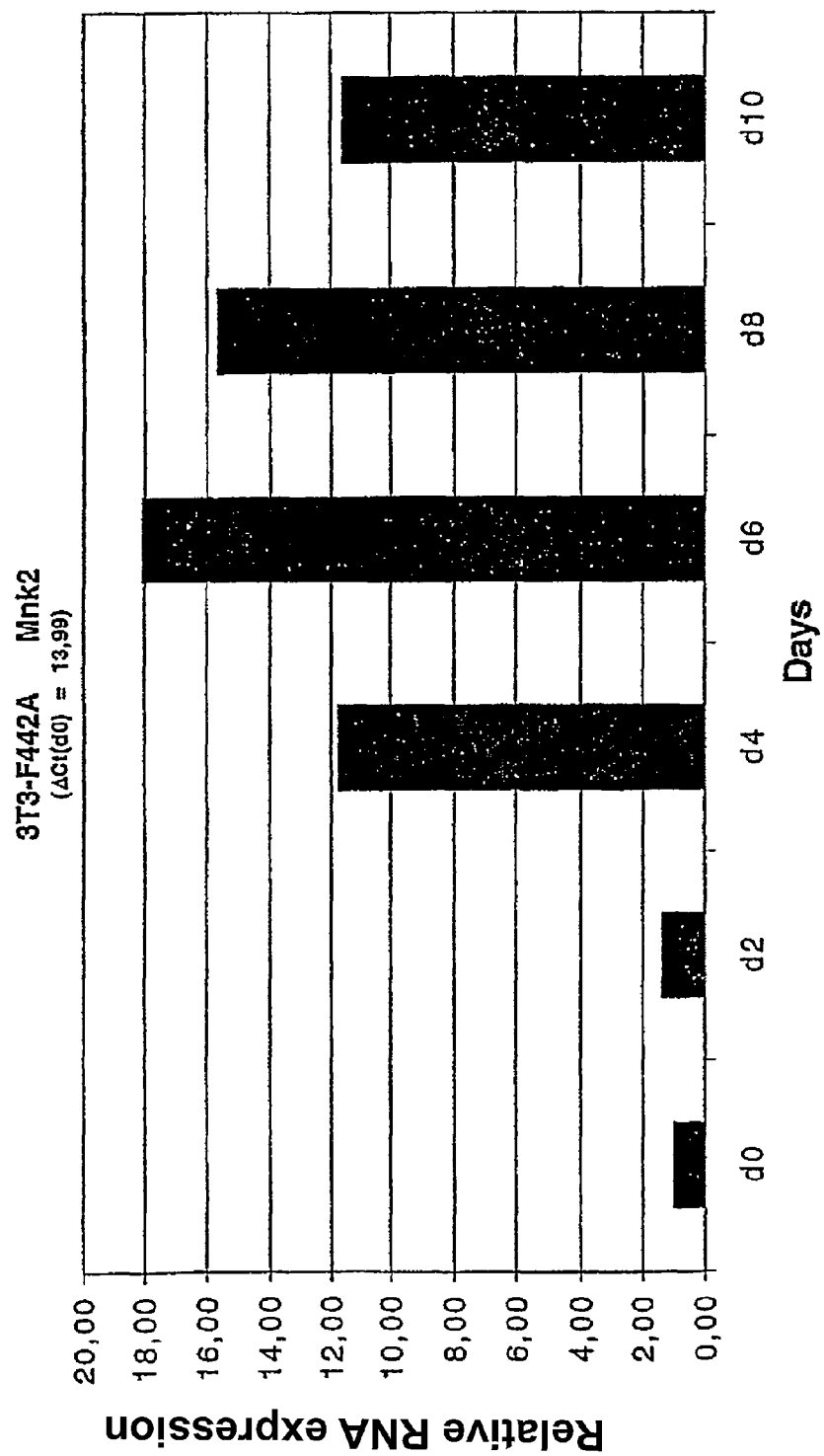
FIG. 5E shows real-time PCR mediated comparison of Mnk2 expression during the differentiation of mammalian fibroblast 3T3-F442A cells from preadipocytes to mature adipocytes.
Figure 5F:
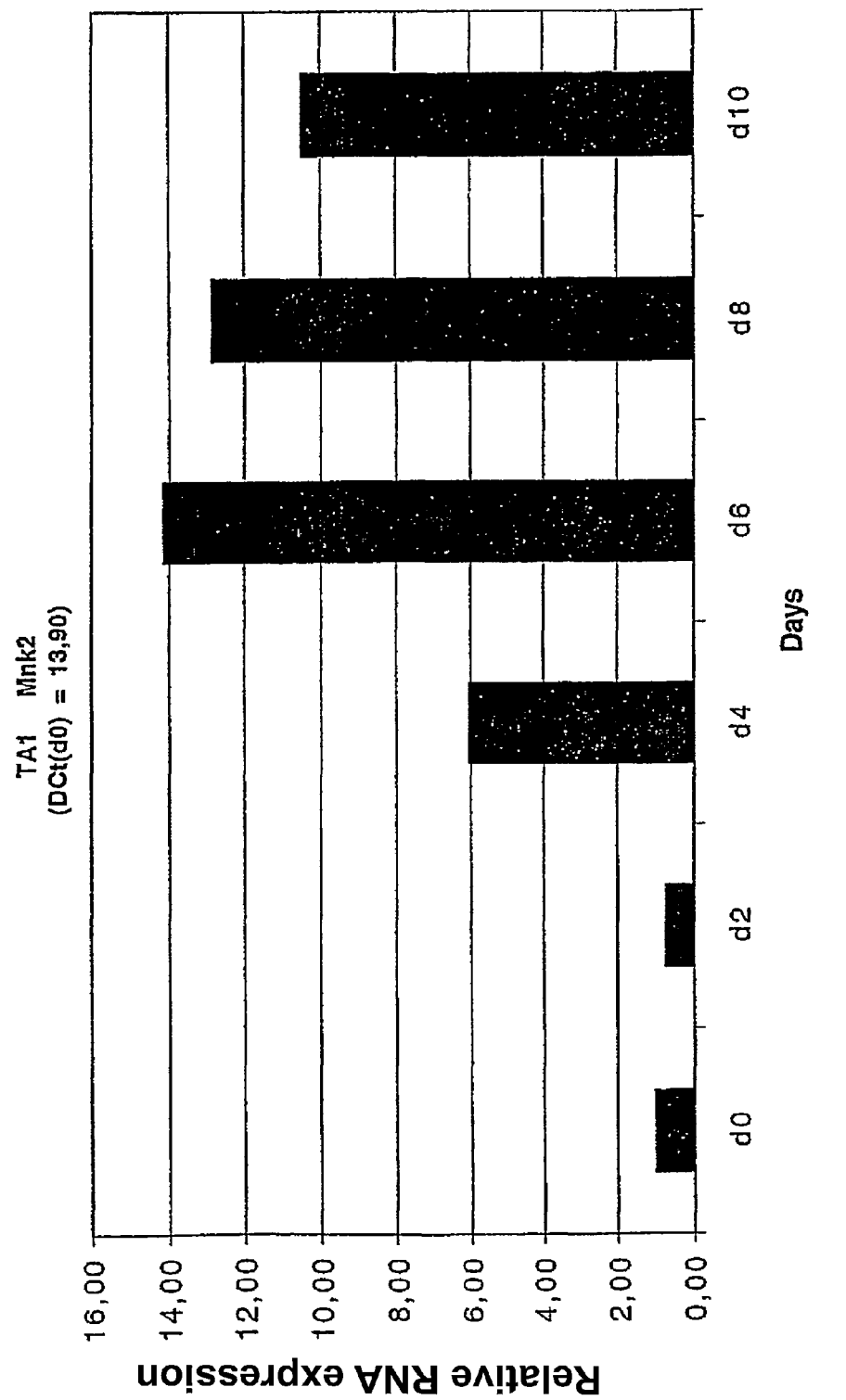
FIG. 5F shows real-time PCR mediated comparison of Mnk2 expression during the differentiation of mammalian fibroblast TA1 cells from preadipocytes to mature adipocytes.
Figure 6A:
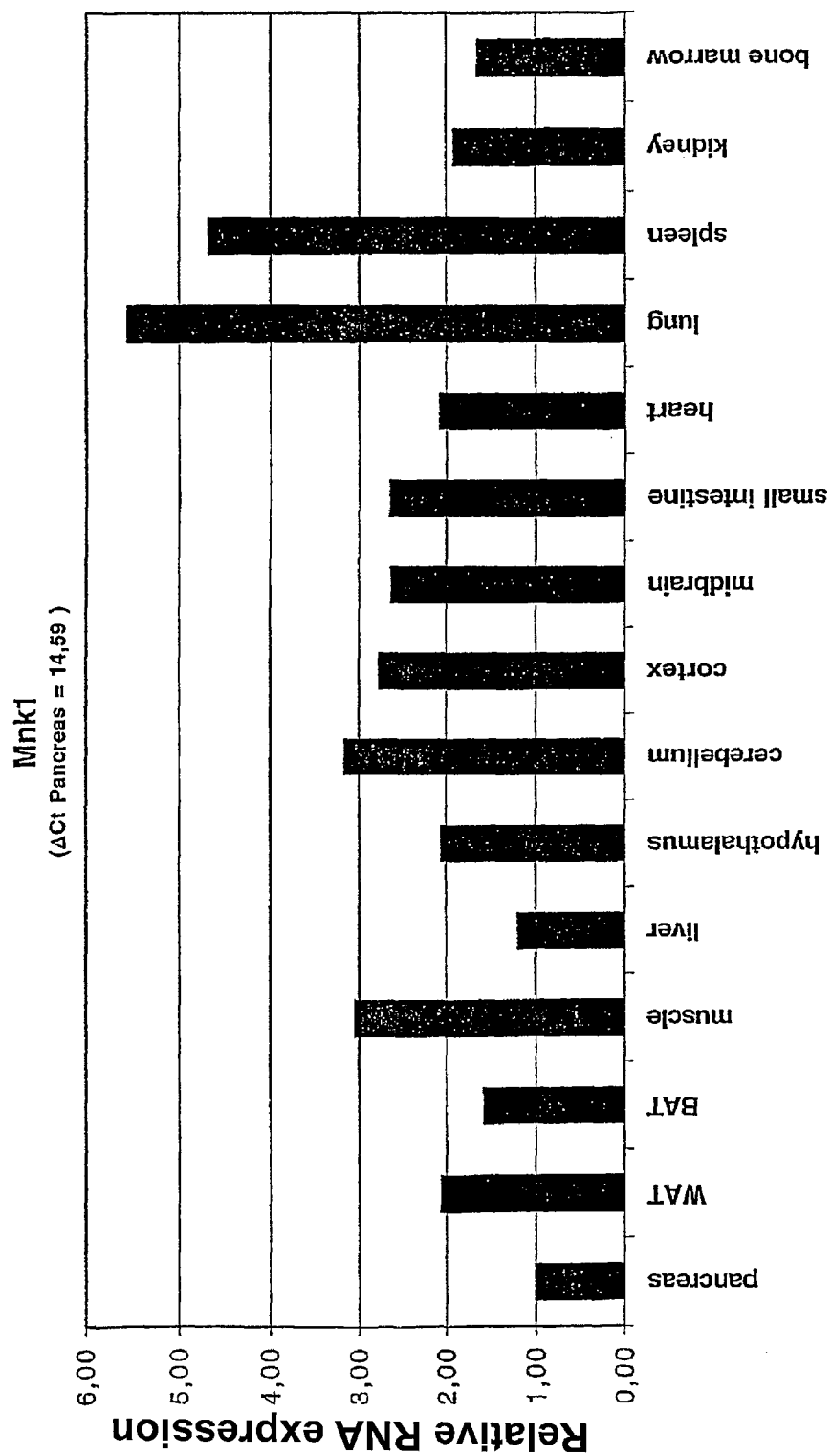
FIGS. 6A and 6B show the expression of the mouse Mnk1 gene in different wild-type mouse tissues.
Figure 6B:
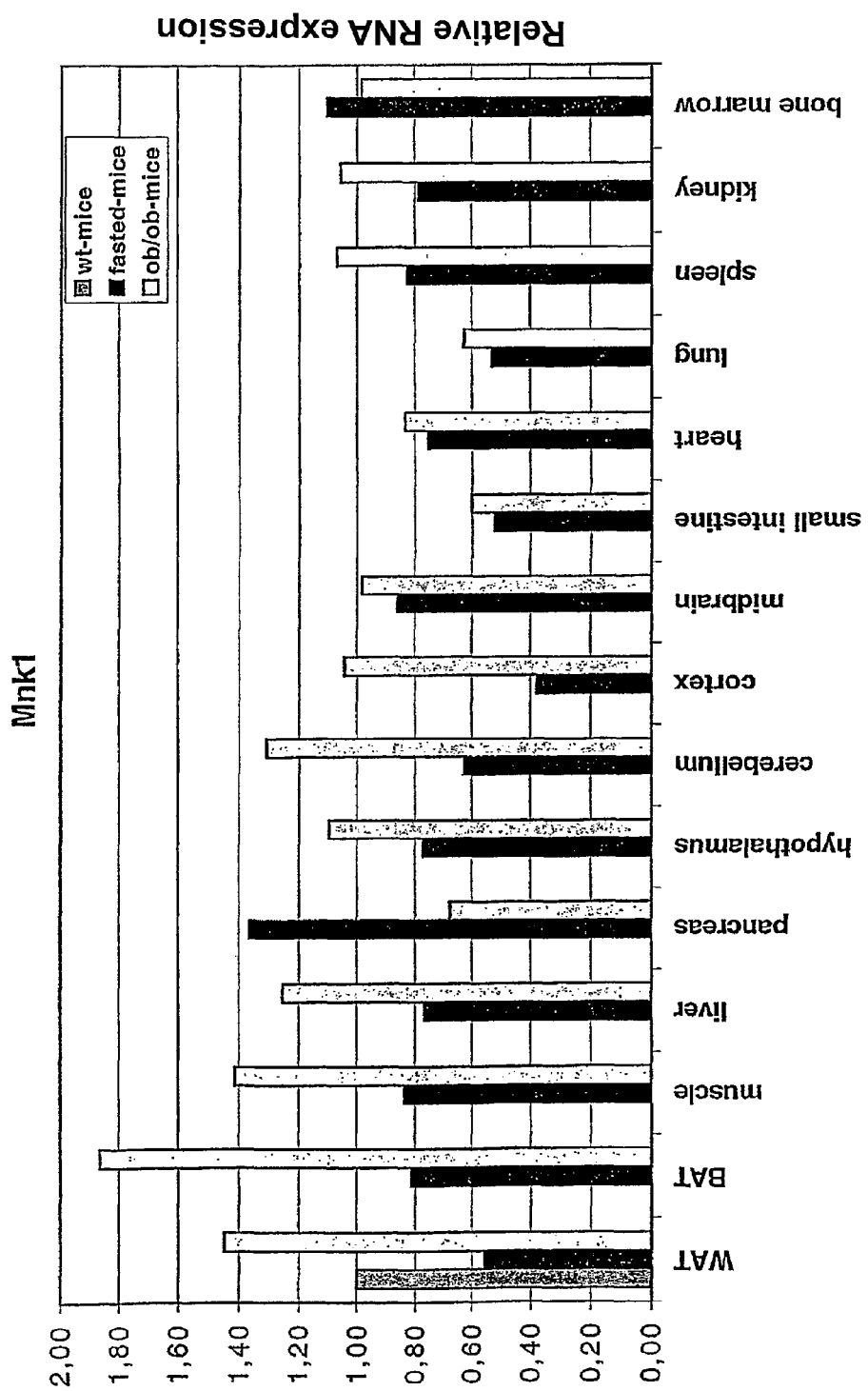
Figure 6C:
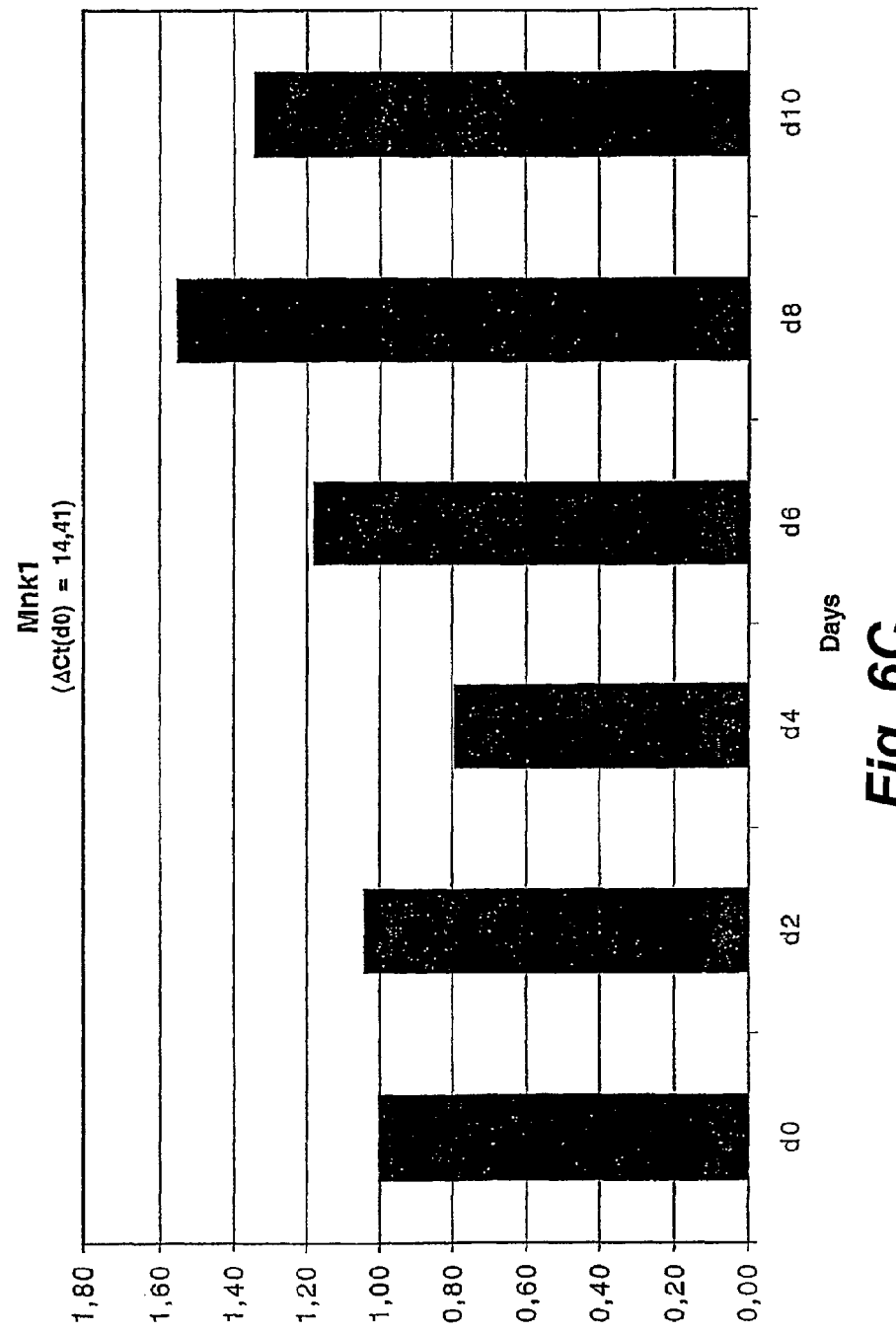
FIG. 6C shows the real-time PCR mediated comparison of Mnk1 expression during differentiation of cultured mammalian fibroblast 3T3-L1 cells from pre-adipocytes to mature adipocytes.
Figure 6D:
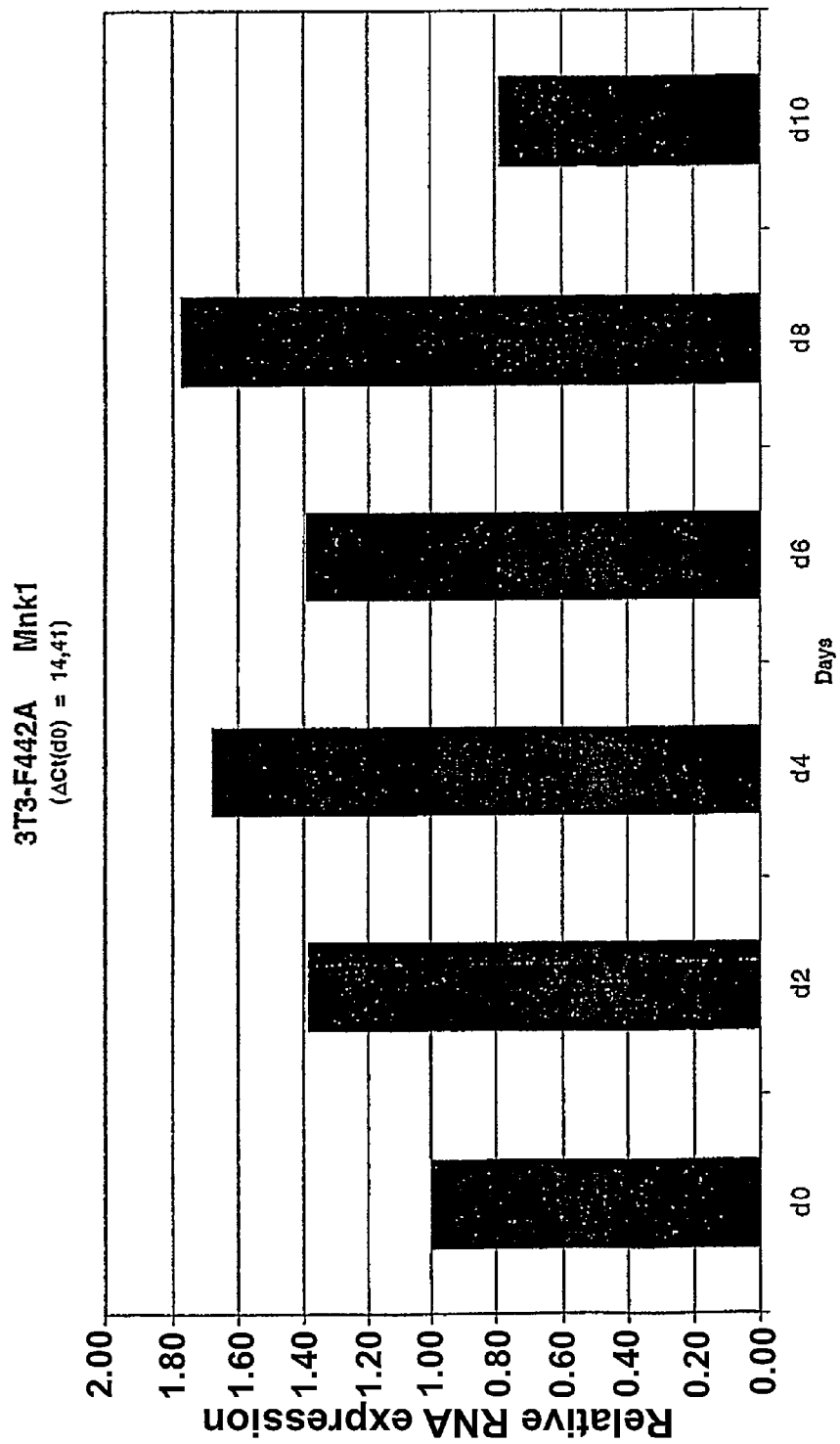
FIG. 6D shows real-time PCR mediated comparison of Mnk1 expression during the differentiation of cultured mammalian fibroblast 3T3-F442A cells from preadipocytes to mature adipocytes.
Figure 6E:
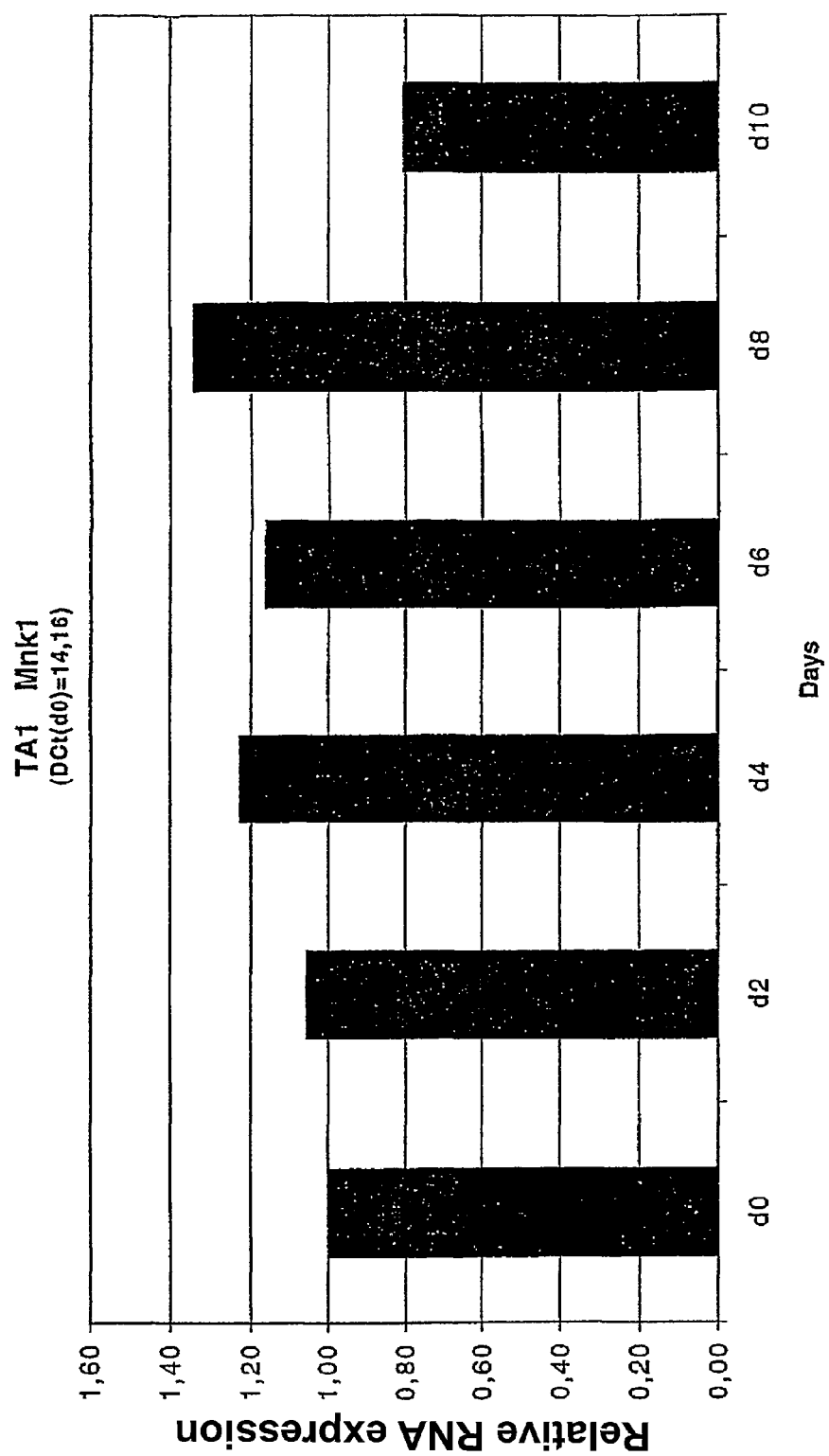
FIG. 6E shows real-time PCR mediated comparison of Mnk1 expression during the differentiation of mammalian fibroblast TA1 cells from preadipocytes to mature adipocytes.

Taqman analysis revealed that Mnk2 is the more interesting homologue of the fly Lk6 gene. The results are shown in FIG. 5 and FIG. 6. In comparison to Mnk1, which is rather ubiquitously expressed, Mnk2 shows its highest expression levels in the brown and white adipose tissues (FIGS. 5A and 6A, respectively). The expression of Mnk2 in white adipose tissue is under metabolic control: In fasted as well as obese (ob/ob) mice, expression is reduced to about 40% of wildtype levels (FIG. 5C; see also FIG. 5B). In addition, expression of Mnk2 is strongly induced during the in vitro differentiation of 3T3-L 1 (FIG. 5D) as well as of two additional model systems for the in vitro differentiation of preadipocytes to adipocytes, the 3T3-F442A and TA1 cell lines (FIG. 5E and FIG. 5F, respectively). Contrary to this, the relative expression levels of Mnk1 remain unchanged during the differentiation of these cell lines (FIGS. 6D and 6E, respectively).

EXAMPLE 9

Expression of the Polypeptides in Mammalian (Human) Tissues (FIG. 9)

Human primary adipocytes were differentiated into mature adipocytes as described by Hauner et al. 1989 (J Clin Invest 84(5): 1663-70). Briefly, cells were grown in DMEM/Nutrient Mix F12, 1% PenStrep, 17 µM Biotin, 33 µM Pantothenat, 10% none heat inactivated fetal calf serum. On day 0 of differentiation, the medium was changed to OM EM/Nutrient Mix F12, 1% Pen/Strep, 17 µM Biotin, 33 µM Pantothenat, 0.01 mg/ml Transferrin, Hydrocortisone, 20 nM humanes Insulin, 0.2 nM T3, 25 nM Dexamethasone, 2500M IBMX, 3 µM Rosiglitazone. On day 4 of differentiation, the medium was changed to DMEM/Nutrient Mix F12 1% Pen/Strep, 17 µM Biotin, 33 µM Pantothenat, 0.01 mg/ml Transferrin, 100 nM Hydrocortisone, 20 nM humanes Insulin, 0.2 nM T3. At various time points of the differentiation procedure, beginning with day 0 (day of confluence) and day 4 (hormone addition), up to 14 days of differentiation, suitable aliquots of cells were taken every two days. RNA was isolated from human cell culture cells using Trizol Reagent (for example, from Invitrogen, Karlsruhe, Germany) and further purified with the RNeasy Kit (for example, from Qiagen, Germany) in combination with an DNase-treatment according to the instructions of the manufacturers and as known to those skilled in the art. In addition to the RNA isolated from human adipocytes at different differentiation stage, RNAs isolated from different human tissues were obtained from Invitrogen Corp., Karlsruhe, Germany: (i) total RNA from human adult skeletal muscle (Invitrogen Corp. Order Number 735030); (ii) total RNA from human adult lung (Invitrogen Corp. Order Number 735020); (iii) total RNA from human adult liver (Invitrogen Corp. Order Number 735018); (iv) total RNA from human adult placenta (Invitrogen Corp. Order Number 735026); (v) total RNA from human adult testis (Invitrogen Corp. Order Number 641 01-1); (vi) total RNA from human normal adipose tissue (Invitrogen Corp. Order Number 06005-01); (vii) total RNA from human normal pancreas (Invitrogen Corp. Order Number DG61 01); (viii) total RNA from human normal brain (Invitrogen Corp. Order Number 06030-01). The RNA was treated with DNase according to the instructions of the manufacturers (for example, from Qiagen, Germany) and as known to those skilled in the art. Total RNA was reverse transcribed (preferably using Superscript II RNaseH-Reverse Transcriptase, from Invitrogen, Karlsruhe, Germany) and subjected to Taqman analysis preferably using the Taqman 2×PCR Master Mix' (page 66, line 31: Weiterstadt, Germany; see Example 8). Taqman analysis was performed preferably using the following primer/probe pairs:

For the amplification of human Mnk2a:

```
human Mnk2a forward primer (SEQ ID NO.: 17):
5'-cca tct ccc cct ctg tac ata gg-3';

human Mnk2a reverse primer (SEQ ID NO.: 18):
5'-ccg get ggc gat age tta a-3';

Taqman probe (SEQ ID NO.: 19):
(5/6-FAM) cac ccg tee ccc aat caa ate taa agg
(5/6-TAMRA)
```

For the amplification of human Mnk2b:

```
human Mnk2b forward primer (SEQ ID NO.: 20):
5'-TTA CTG TGA ATG AGT GAA GAT CCT GG-3';

human Mnk2b reverse primer (SEQ ID NO.: 21):
5'-ATG GCC GTT CAC CGT CC-3';

Taqman probe (SEQ ID NO.: 22):
(5/6-FAM) CCA GGC GAG CTC CCA TCG CTG (5/6-TAMRA).
```

Figure 9A:
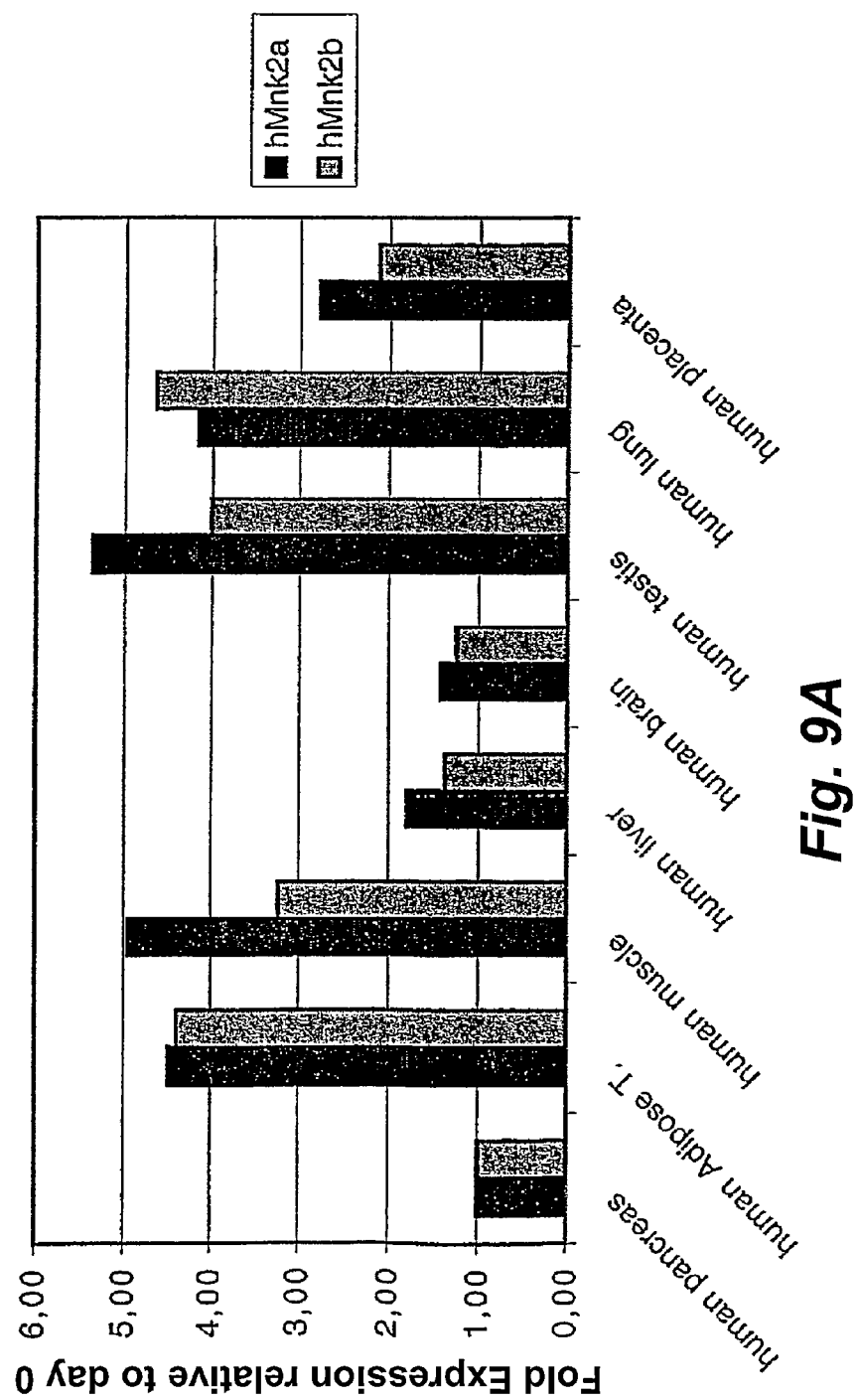
Figure 9B:
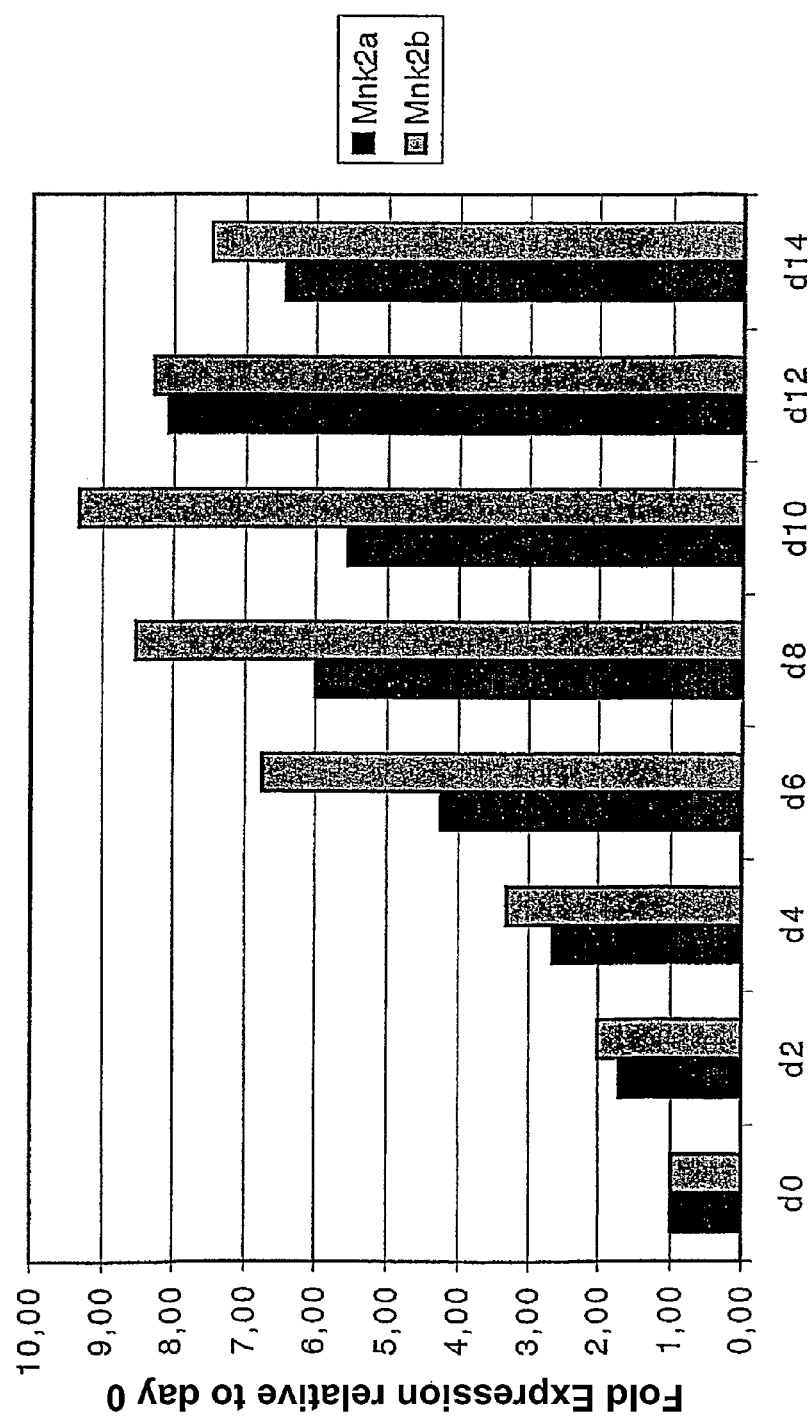

As shown in FIG. 9A, real time PCR (Taqman) analysis of the expression of Mnk2a and Mnk2b protein in human tissues revealed that both proteins are expressed in all tissues analyzed with high levels of expression in adipose tissue, muscle, lung, testis, and placenta. The relative expression levels of both human Mnk2 splice variants is the same for all tissues analyzed. Both show highest expression levels in tissues relevant for metabolic disorders namely adipose and muscle tissue. As shown in FIG. 9B, Mnk2a as well as Mnk2b are upregulated during human adipocyte differentiation. This suggests a function of both proteins in the metabolism of mature adipocytes.

EXAMPLE 10

Assays for the Determination of Triglyceride Storage, Synthesis and Transport (FIG. 8)

Retroviral Infection of Preadipocytes

Packaging cells were transfected with retroviral plasmids pLPCX carrying mouse Mnk2 transgene and a selection marker using calcium phosphate procedure. Control cells were infected with pLPCX carrying no transgene. Briefly, exponentially growing packaging cells were seeded at a density of 350,000 cells per 6-well in 2 ml DMEM+10% FCS one day before transfection. 10 min before transfection chloroquine was added directly to the overlying medium (25 µM final concentration). A 250 µl transfection mix consisting of 5 µg plasmid-DNA (candidate: helper-virus in a 1:1 ratio) and 250 mM $CaCl_2$ was prepared in a 15 ml plastic tube. The same volume of 2×HBS (280 µM NaCl, 50 µM HEPES, 1.5 mM $Na_2HPO_4$, pH 7.06) was added and air bubbles were injected into the mixture for 15 sec. The transfection mix was added drop wise to the packaging cells, distributed and the cells were incubated at 37° C., 5% $CO_2$ for 6 hours. The cells were washed with PBS and the medium was exchanged with 2 ml DMEM+10% CS per 6-well. One day after transfection the cells were washed again and incubated for 2 days of virus collection in 1 ml DMEM+10% CS per 6-well at 32° C., 5% $CO_2$. The supernatant was then filtered through a 0.45 µm cellulose acetate filter and polybrene (final concentration 8 µg/ml) was added. Mammalian fibroblast (3T3-L1) cells in a sub-confluent state were overlaid with the prepared virus containing medium. The infected cells were selected for 1 week with 21-Jg/ml puromycin. Following selection the cells were checked for transgene expression by western blot and immunofluorescence. Over expressing cells were seeded for differentiation. 3T3-L 1 cells were maintained as fibroblasts and differentiated into adipocytes as described in the prior art and in example 8. For analysing the role of the proteins disclosed in this invention in the in vitro assays for the determination of triglyceride storage, synthesis and transport were performed.

Preparation of Cell Lysates for Analysis of Metabolites

Starting at confluence (DO), cell media was changed every 48 hours. Cells and media were harvested 8 hours prior to media change as follows. Media was collected, and cells were washed twice in PBS prior to lyses in 600 µl HB-buffer (0.5% Polyoxyethylene 10 tridecylethan, 1 mM EDTA, 0.01 M $NaH_2PO_4$, pH 7.4). After inactivation at 70° C. for 5 minutes, cell lysates were prepared on Bio 101 systems lysing matrix B (0.1 mm silica beads; Q-Biogene, Carlsbad, USA) by agitation for 2×45 seconds at a speed of 4.5 (Fastprep FP120, Bio 101 Thermosavant, Hoi brock, USA). Supernatants of lysed cells were collected after centrifugation at 3000 rpm for 2 minutes, and stored in aliquots for later analysis at −80° C.

Changes in cellular triglyceride levels during adipogenesis (FIG. 8A) Cell lysates and media were simultaneously analyzed in 96-well plates for total protein and triglyceride content using the Bio-Rad DC Protein assay reagent (Bio-Rad, Munich, Germany) according to the manufacturer's instructions and a modified enzymatic triglyceride kit (GPO-Trinder; Sigma) briefly final volumes of reagents were adjusted to the 96-well format as follows: 10 µl sample was incubated with 200 µl reagent A for 5 minutes at 37° C. After determination of glycerol (initial absorbance at 540 nm), 50 µl reagent B was added followed by another incubation for 5 minutes at 37° C. (final absorbance at 540 nm). Glycerol and triglyceride concentrations were calculated using a glycerol standard set (Sigma) for the standard curve included in each assay.

Figure 8A:
FIGS. 8A and 9B: In vitro assays for the determination of triglyceride storage, synthesis and transport.

As shown in FIG. 8A, we found that in Mnk2 overexpressing cells cellular triglyceride levels were significantly lower from day 4 to day 12 of adipogenesis compared to that in the control cells (FIG. 8A). These results indicate that Mnk2 targets regulatory pathways or enzymes involved in lipid metabolism, which we analyzed in more detail in the lipid synthesis and FFA transport assays described below.

Figure 8B:
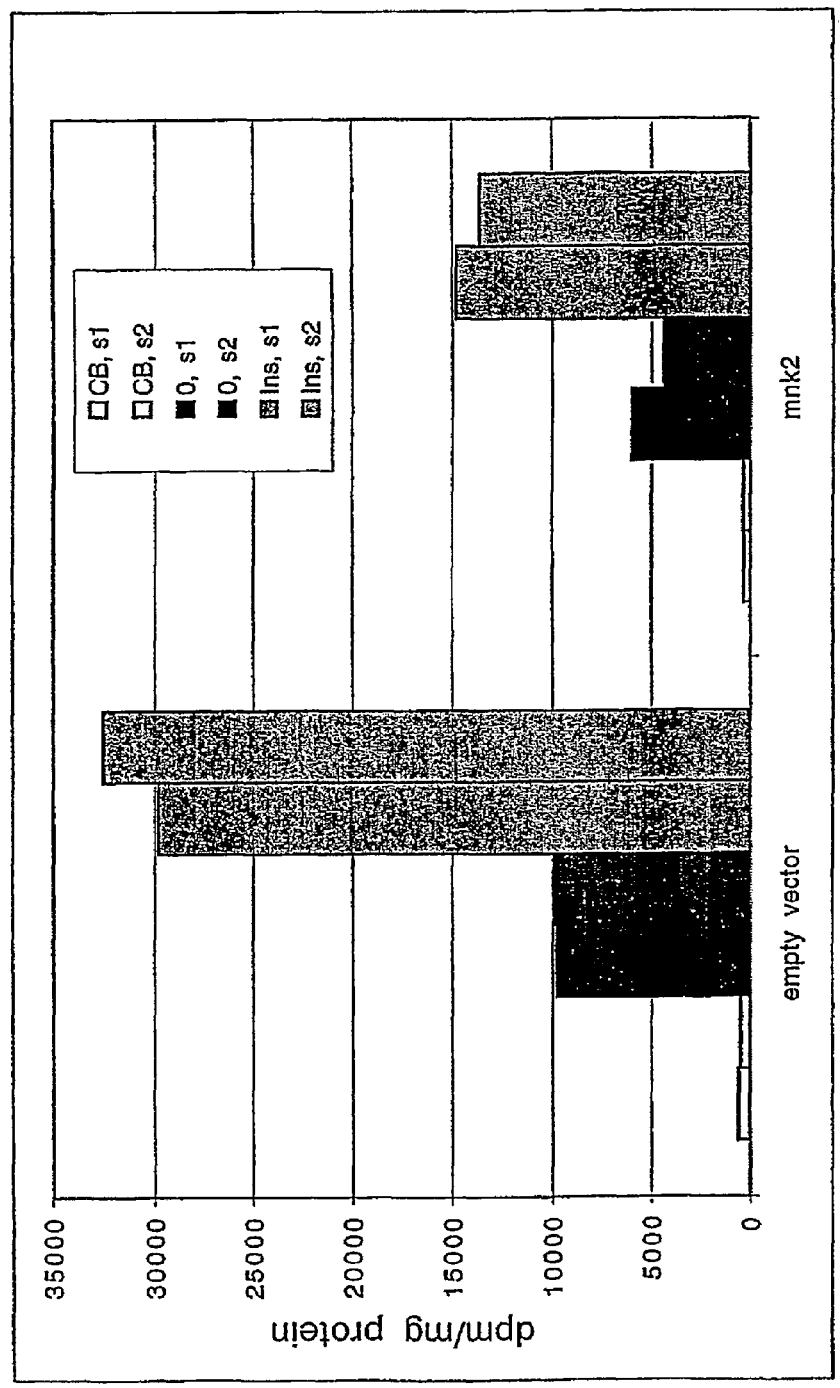
FIG. 8B shows reduction in insulin-stimulated lipid synthesis (dpm/mg protein) in cells over-expressing Mnk2 compared to control cells. All samples were analyzed in duplicates (s1; sample 1, s2; sample 2). CB; cytochalasin B, illustrates the background synthesis in 3T3L1, 0; represents the baseline or un-stimulated glucose transport and hence basal lipid synthesis in the cells, while Ins; insulin shows the stimulated glucose transport and the consequent synthesis of glucose to lipid in 3T3L1 cells. The Y-axis displays disintegrations per minutes/mg protein (dpm/mg protein) and the X-axis denotes the aforementioned proteins.

Synthesis of Lipids During Adipogenesis (FIG. 8B)

During the terminal stage of adipogenesis (day 12) cells were analyzed for their ability to metabolize lipids. A modified protocol to the method of Jensen et al (2000), JBC 275, 40148, for lipid synthesis was established. Cells were washed 3 times with PBS prior to serum starvation in Krebs-Ringer-Bicarbonate-Hepes buffer (KRBH; 134 nM NaCl, 3.5 mM KCl, 1.2 mM $KH_2PO_4$, 0.5 mM 04, 1.5 mM $CaCl_2$, 5 mM $NaHCO_3$, 10 mM Hepes, pH 7.4), supplemented with 0.1% FCS for 2.5 h at 37° C. For insulin-stimulated lipid synthesis, cells were incubated with 1 µM bovine insulin (Sigma; carrier: 0.005 N HCl) for 45 min at 37° C. Basal lipid synthesis was determined with carrier only. $^{14}C(U)$-D-Glucose (NEN Life Sciences) in a final activity of 1 µCi/Well/ml in the presence of 5 mM glucose was added for 30 min at 37° C. For the calculation of background radioactivity, 25 µM Cytochalasin B (Sigma) was used. All assays were performed in duplicate wells. To terminate the reaction, cells were washed 3 times with ice cold PBS, and lysed in 1 ml 0.1 N NaOH.

Protein concentration of each well was assessed using the standard Biuret method (Protein assay reagent; Bio-Rad). Total lipids were separated from aqueous phase after overnight extraction in Insta-Fiuor scintillation cocktail (Packard Bioscience) followed by scintillation counting.

Our results clearly show that Mnk2 overexpressing cells were less effective at synthesizing lipids from exogenous glucose. Consequently, the levels of insulin stimulated lipid synthesis are significantly lower at day 12 of adipogenesis when compared to control cells (FIG. 8B). The lower lipid levels observed in the experiments above therefore result most likely from a lower lipid synthesis rate and are not the result of an increased turnover of lipid stores.

Figure 8C:
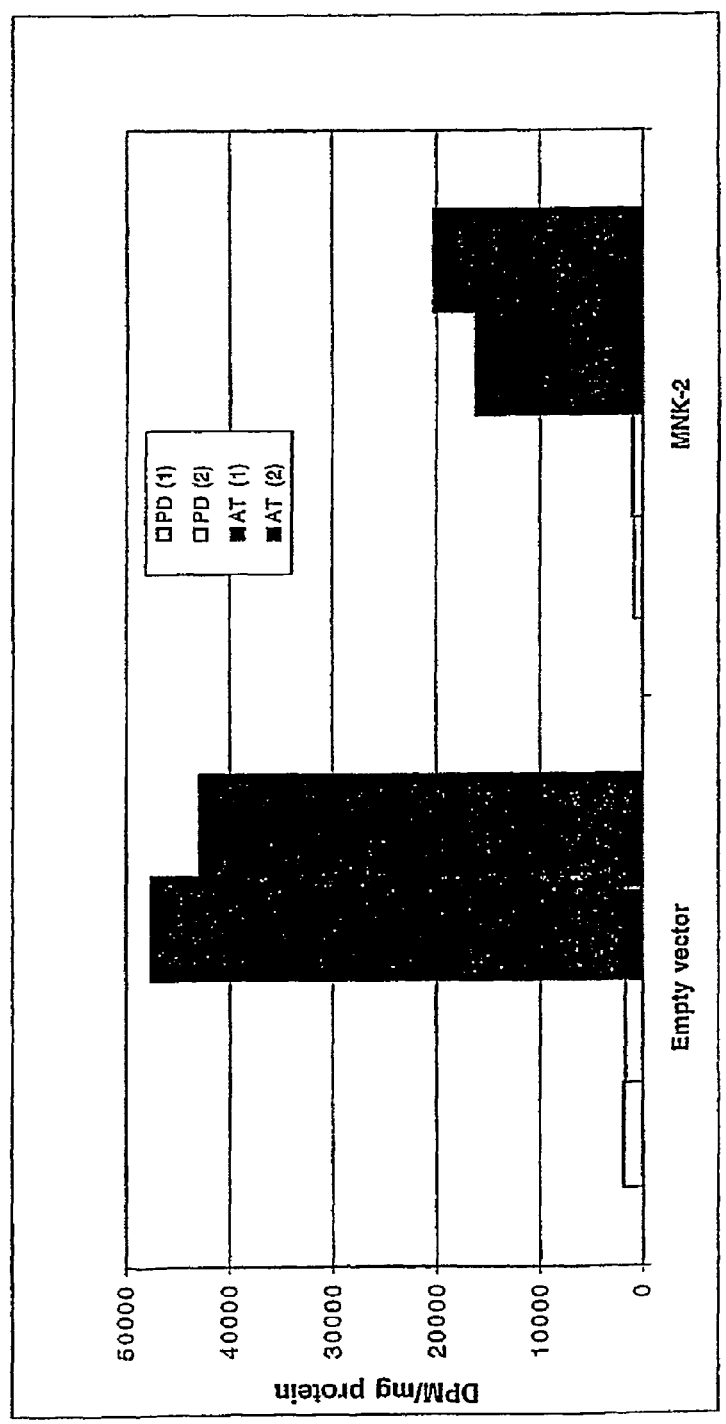
FIG. 8C shows reduction in active transport (AT) of free fatty acids across the plasma membrane of cells over expressing Mnk2 compared to control cells. All samples were analyzed in duplicates (as illustrated by twin bar of identical shadings). PD; passive diffusion illustrated the baseline or non-energy dependent transportation of exogenous fatty acids across the membrane. AT; active transport represents energy dependent transportation of fatty acids across the membrane. The Y-axis shows disintegrations per minutes/mg protein (dpm/mg protein) and the X-axis displays the aforementioned proteins.

Transport and Metabolism of Free Fatty Acids Across During Adipogenesis (FIG. 8C)

During the terminal stage of adipogenesis (D12) cells were analyzed for their ability to transport long chain fatty acid across the plasma membrane. A modified protocol to the method of Abumrad et al (1991) (Proc. Natl. Acad. Sci. USA, 1991: 88; 6008-12) for cellular transportation of fatty acid was established. In summary, cells were washed 3 times with PBS prior to serum starvation. This was followed by incubation in KRBH buffer, supplemented with 0.1% FCS for 2.5 h at 37° C. Uptake of exogenous free fatty acids was initiated by the addition of isotopic media containing non radioactive oleate and ($^3$H)oleate (NEN Life Sciences) complexed to serum albumin in a final activity of 1 µCi/Well/ml in the presence of 5 mM glucose for 30 min at room temperature (RT). For the calculation of passive diffusion (PD) in the absence of active transport (AT) across the plasma membrane 20 mM of phloretin in glucose free media (Sigma) was added for 30 min at room temperature (RT). All assays were performed in duplicate wells. To terminate the active transport 20 mM of phloretin in glucose free media was added to the cells. Cells were lysed in 1 ml 0.1 N NaOH and the protein concentration of each well were assessed using the standard Biuret method (Protein assay reagent; Bio-Rad). Esterified fatty acids were separated from free fatty acids using overnight extraction in Insta-Fiuor scintillation cocktail (Packard Bioscience) followed by scintillation counting.

We found that transport of exogenous fatty acids across the plasma membrane of Mnk2 overexpressing cells and hence esterification of these metabolites were considerably lower at day 12 of adipogenesis when compared to control cells (FIG. 8C). Taken together the overexpression of Mnk2 showed an effect on triglyceride metabolism in all three assays we performed in 3T3-L1 cells, making it a potential interesting drug target to treat metabolic disorders.

EXAMPLE 11

Generation and Analysis of Mnk2 Transgenic Animals (I3-Actin-mMnk2DN)

Generation of the Transgenic Animals

Mouse Mnk2 cDNA was isolated from mouse brown adipose tissue (BAT) using standard protocols as known to those skilled in the art. The cDNA was amplified by RT-PCR using the following primer pair:

```
Mnk2 forward primer (SEQ ID NO.: 23):
5' AAG TTG GCC TTC GCG TTA GAG 3'

Mnk2 reverse primer (SEQ ID NO.: 24):
5' CGA TAT GTA CAA GGA GCT AG 3'.
```

The resulting Mnk2 cDNA was cloned into pBluescript KS+ (Stratagene) according to standard protocols, resulting in a plasmid referred to as pKS+-mMnk2'. The cDNA of pKS+-mMnk2 c was mutated using site directed mutagenesis (Stratagene), according to the manufacturer's instructions. Using the Mnk2 top oligo (SEQ ID NO.: 25): 5' CTC CCC CAT CTC CGC ACC AGA GCT GCT CGC CCC GTG TGG GTC AG 3' and the Mnk2 bottom oligo (SEQ ID NO.: 26): 5' CTG ACC CAC ACG GGG CGA GCT CTG GTG CGG AGA TGG GGG AG 3', two point mutations were introduced into the cDNA resulting in amino acid exchanges at position T197 and T202 to A197 and A202 of the Mnk2 cDNA.

The resulting mutated cDNA (referred to as mMnk2DN) was cloned into the EcoRV cloning site of the transgenic expression vector pTG-β-actin-X-hgh-bgh-polyA. The β-actin-Mnk2DN transgene was microinjected into the male pronucleus of fertilized mouse embryos (preferably strain C57/BL6/CBA F1 (Harlan Winkelmann). Injected embryos were transferred into pseudo-pregnant foster mice. Transgenic founders were detected by PCR analysis using the forward primer (SEQ ID NO.: 27): 5' GCT GCT GGT CCG AGA TGC C 3' and reverse primer (SEQ ID NO.: 28): 5' GGG TCA TGC GCG ATC CCC 3'. Two independent transgenic mouse lines containing the β-actin-Mnk2DN construct were established and kept on a C57/BL6 background. Briefly, founder animals were backcrossed with C57/BL6 mice to generate F1 mice for analysis. Transgenic mice were continuously bred onto the C57/BL6 background.

Figure 10:
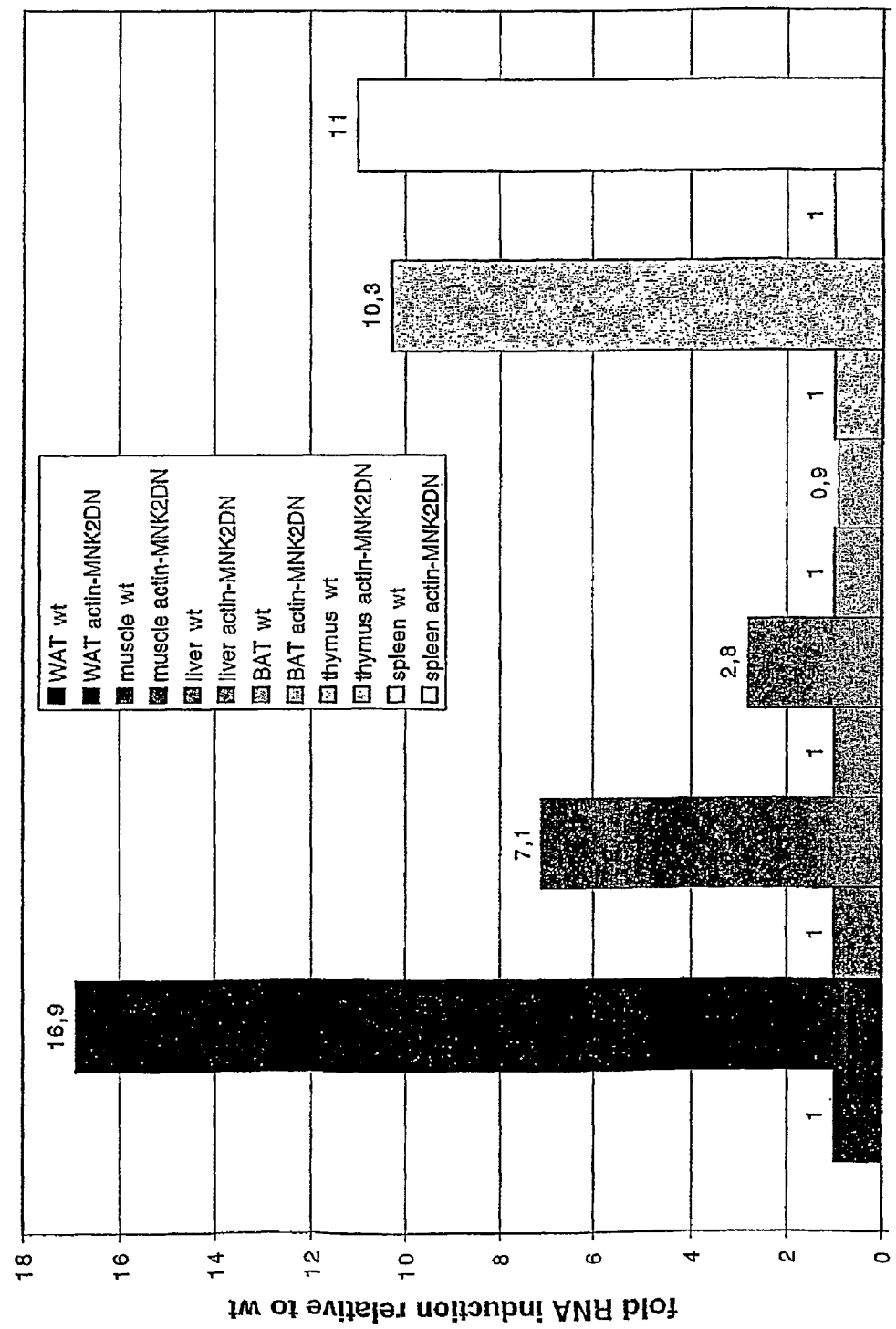
FIG. 10 shows the expression of the ectopic mouse Mnk2 (mMnk2DN) transgene in actin-mMnk2DN transgenic mice. Shown is a Taqman analysis on different tissues isolated from male actin-mMnk2DN transgenic mice and male wild-type littermates. Data are expressed as fold RNA induction relative to the corresponding wild-type (wt) tissue. The number on top of each bar indicates the fold induction relative to the corresponding wt tissue. Shown is a representative experiment.

Expression of the construct in different mouse tissues (FIG. 10) using standard techniques, β-actin-Mnk2DN transgene expression was verified by Taqman analysis using forward primer (SEQ ID NO.: 29): 5' CAG CGT GGT AGT ACA GGA CGT G 3', reverse primer (SEQ ID NO.: 30): 5' TCC CTG TGG GCG ATG C 3' and primer (SEQ ID NO.: 31): 5' CAG TGC CCT GGA CTT CCT GCA TAA CAA 3'. Taqman analysis was performed using a representative panel of mouse tissues.

The expression of the bactin-Mnk2DN transgene was observed in the following tissues: WAT, muscle, liver, kidney, thymus, heart, lung, and spleen. Expression levels of the transgene were 2.8-16.9 fold increased relative to Mnk2 expression in wild-type mice, depending on the tissue analyzed. No Mnk2 transgene expression was detected in BAT tissue (see FIG. 10).

Figure 11:
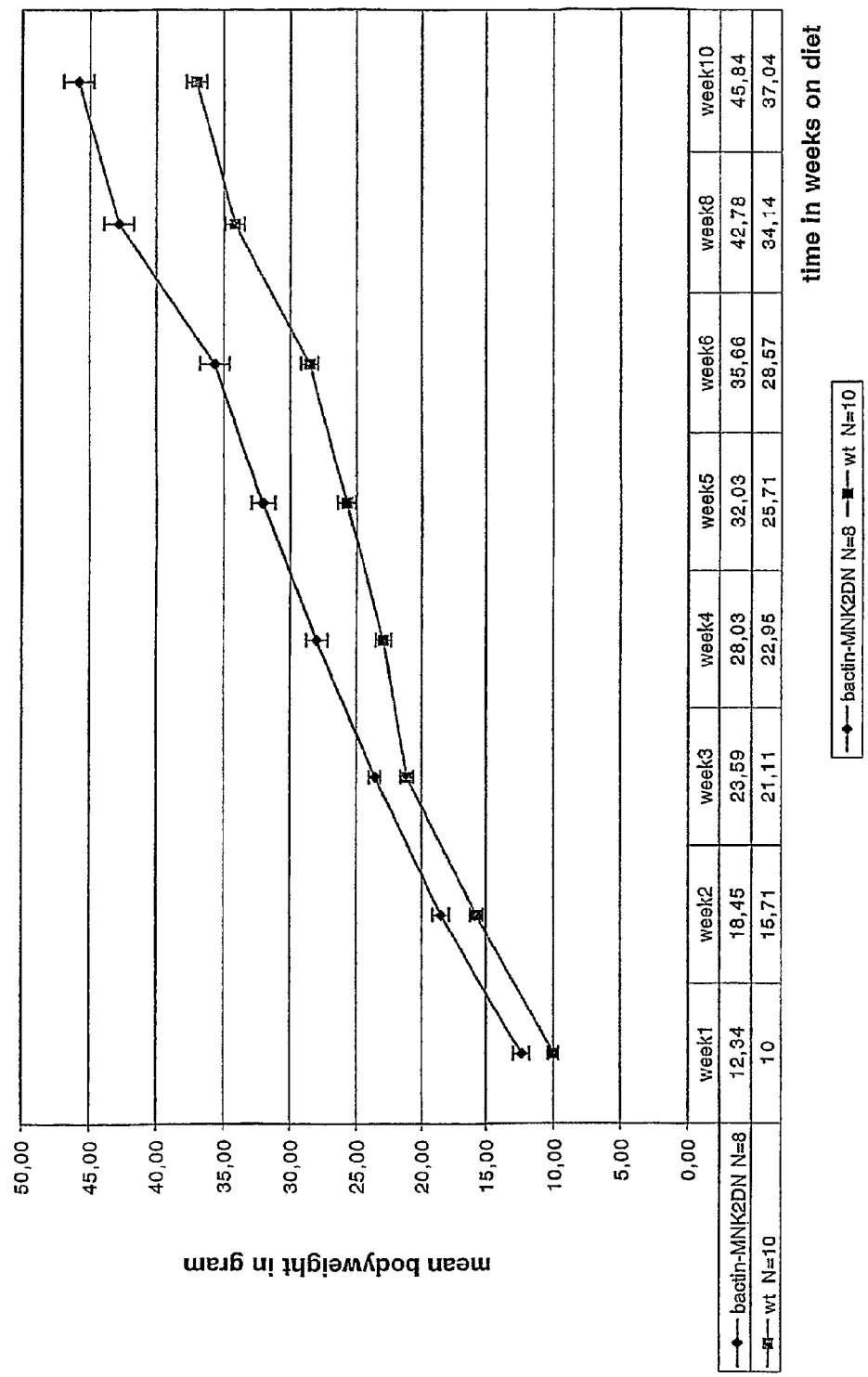
FIG. 11 shows that the ectopic mouse Mnk2 (mMnk2DN) expression in actin-mMnk2DN transgenic mice leads to increased body weight. Shown are growth curves from male bactin-mMnk2DN transgenic mice (♦, upper trace) and male wt littermates (■, lower trace) on high fat diet over a time of 10 weeks. Data are expressed as mean body weight overtime+/−SE. Shown is a representative experiment with N=8 respectively N=10 mice per group.

Analysis of the Bodyweight of the Transgenic Mice (FIG. 11)

After weaning, male β-actin-mMnk2DN transgenic mice and their wild-type (wt) littermates controls were placed in groups of 4 to 5 animals (N=4 up to N=5) on control diet (preferably Altromin C1057 mod control, 4.5% crude fat or high fat diet (preferably Altromin C1057mod. high fat, 23.5% crude fat). Total body weight of the animals was measured weekly over a period of 12-16 weeks. On each diet, mean bodyweight of β-actin-mMnk2DN transgenic mice was clearly increased compared to wildtype littermates on the respective diet. Significant differences in mean bodyweight were first observed around the end of postnatal week 4 on both diets. After 10 weeks on high fat diet, the mean bodyweight of β-actin-mMnk2DN transgenic mice compared to wt littermates was increased by 8.8 g (=23% increase in mean bodyweight relative to wt littermates) (FIG. 11). Similar differences in mean body weight were observed in wt and β-actin-mMnk2DN transgenic mice on control diet (data not shown). Thus, our results clearly show that the ectopic expression of mMnk2DN transgene leads to an increase in bodyweight. The effect appears independently of the diet give, as it can be seen on control diet as well as on high fat diet.

EXAMPLE 12

Figure 13:
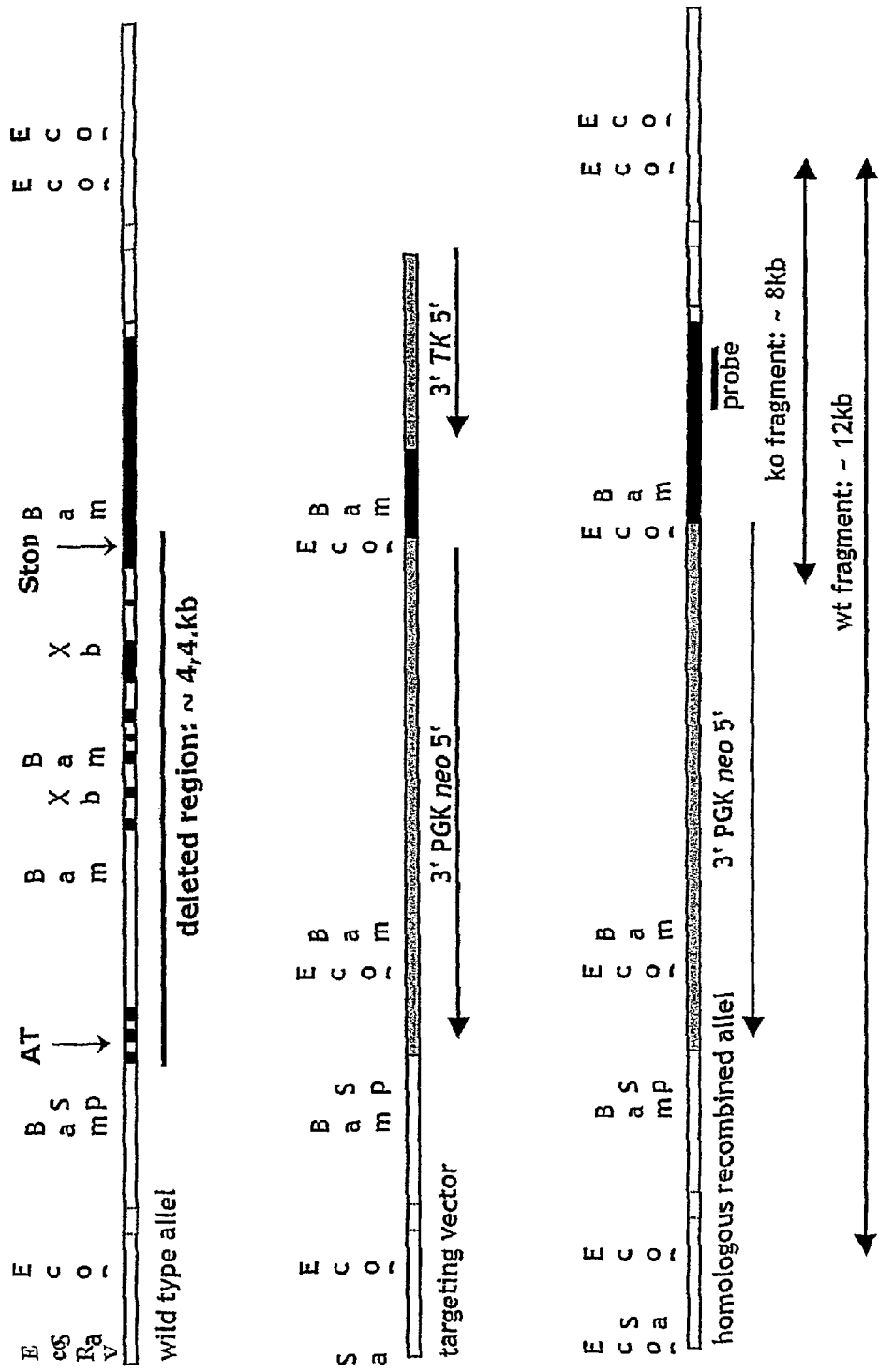
FIG. 13 illustrates the targeted deletion of the mouse Mnk2 gene by homologous recombination. The top line shows the wild type locus of mouse Mnk2, the graphic in the middle shows the targeting vector, and the graphic at the bottom part of the figure illustrates the targeted locus. The exons are shown as black boxes. Restriction sites, translation start site, and stop codon are indicated. The PGK-NEO cassette and the TK cassette are shown as grey boxes. 4.4 kb of genomic region of the mouse Mnk2 gene is replaced by a PGK NEO cassette. The deleted region is indicated. The outside flanking probe used for Southern blot analysis is shown by a black bar. The genomic fragments detected with this probe on EcoR1 digested DNA are shown as arrows. See examples for more detail.

Generation and Analysis of mMnk2−/− Mice (FIG. 12 and FIG. 13)

A 605 base pair probe of the mMnk2 cDNA (GenBank accession number BC010256; position 61-665) was amplified from mouse white adipose tissue (WAT) cDNA by PCR using forward primer (SEQ ID NO.: 32): 5' ACA TCA GCC CAC AGT GTG A 3' and reverse primer (SEQ ID NO.: 33): 5' TCT CCA TTG AGT TTG AT A CCA 3'. This probe was used to screen a 129SV J genomic phage library (obtained from Stratagene). Three independent clones were isolated and subcloned into the NotI cloning site of pBluescript KS+ (Stratagene). These genomic clones were used for restriction mapping and sequencing to characterize the genomic locus of mouse Mnk2 (FIG. 12). A PGK-neomycin cassette was inserted into the locus of mouse Mnk2 replacing 4.4 kb of genomic DNA thereby deleting the complete coding region of mMnk2. Briefly, an 8 kb SpeI-NotI fragment was cloned into the XbaI site of pBluescript KS+ upstream of the PGK-Neomycin cassette, which was inserted into the SmaI site of pBluescript. A 1 kb genomic fragment was amplified by PCR using the following primer pair (non priming nucleotides/attached restriction sites are lower case letters): Mnk2-SA forward primer (SEQ ID NO.: 34): EcoRI 5' cgg aat CCA CTA GCT CCT TGT ACA TAT 3'; Mnk2-SA reverse primer (SEQ ID NO.: 35): ClaI 5' cca tcg atG GAA CTC GTA TTG CAT AGT AG 3'. The resulting fragment was inserted into the EcoRI/ClaI site of pBluescript KS+. As a negative selection marker a thymidine kinase cassette was cloned into ClaI/XhoI site of the targeting construct. (FIG. 13). The construct was linearized by NotI digestion and electroporated into mouse embryonic stem (ES) cells. ES cell clones were selected by G418 and Gancyclovir treatment (preferably 350 µg G4181 ml and 2 µM Gancyclovir). Out of 600 neomycin resistant colonies, two independent homologous recombined ES cell clones were identified by PCR. The results were confirmed by southern blot analysis with EcoRI digested genomic DNA using a 3' flanking probe (position 2495-3065 mMnk2 cDNA). A single integration event was confirmed by Southern blot analysis of BamHI digested DNA with a Neomycin probe. ES cell clones were aggregated with 8-cell-stage embryos from NMRI mice and developing blastocysts were transferred into pseudo-pregnant mice to generate chimeras. Chimeras were bred with C57/BL6 mice and offsprings were genotyped by PCR using the following primers: Mnk2-ES primer (SEQ ID NO.: 36): 5' AGA CTA GGG AGG AGG GTG GAG GA 3'; Mnk2-KO primer (SEQ ID NO.: 37): 5' GGT GGA TGT GGA ATG TGT GCG A 3'; Mnk2-WT 5' GGG GTG TAG GGG TCT GTT AGG 3'. Heterozygous mice were used for further intercrosses and analyzed.

EXAMPLE 13

Small Molecule Screening

Compounds which are suitable for the prophylaxis, treatment or diagnosis of Mnk-related metabolic disorders may be identified via a kinase assay, a binding assay or any other suitable assay to measure a function associated with the Mnk polypeptide, a Mnk polypeptide fragment or derivative thereof. This kinase assay may be based on recombinant human Mnk2 (Mnk2a or Mnk2b) or Mnk1 protein and a labelled peptide comprising the eIF4E target sequence, a labelled recombinant eIF4E target sequence or a labelled recombinant eiF4E protein as a substrate. The assay may be a radioactive kinase assay or an assay based on using an anti-phosphoserine antibody which is capable of recognizing eIF4E phosphorylation at Ser209.

For example, the kinases Mnk2a (GenBank Accession Number AF237775 (SEQ ID NO.: 2); see also FIGS. 3D and 3E), Erk2 (GenBank Accession Number M84489, SEQ ID NO.: 84) and a double point mutant of Mek1 (GenBank Accession Number 002750) containing the amino acid substitutions Ser218Asp and Ser222Glu (S218D S222E) were expressed in E. coli and subsequently purified using methods known to those skilled in the art. Preferably, in a kinase reaction of 50 µl, 2.0 µM Mnk2a was incubated with 200 nM Erk2 plus 20 nM Mek1 S218D S222E (labelled lanes 1 to 4 in FIG. 14) or with 50 nM Erk2 plus 2.5 nM Mek1 S218D S222E (labelled lanes 5 to 8 in FIG. 14) in the presence of 1.0 mM ATP, 50 mM Hepes/KOH, mM magnesium chloride and 0.5 mM OTT at 30° C. At the indicated time points (0, 10, 20 and 40 minutes, see FIG. 14), samples were taken from the reaction, diluted in SDS sample buffer containing 50 mM EDTA and separated by SDS polyacrylamide gel electrophoresis (SDS-PAGE). SDS-PAGE separated reaction samples were blotted onto nitrocellulose and probed with an antibody against a phospho-epitope, essential for the activation of Mnk (anti-Phospho-Mnk Thr197/202; Cell Signaling Technology, Inc., Beverly, Mass.). The anti-Phospho-Mnk antibody was detected with a peroxidase-coupled anti rabbit antibody (Sigma-Aldrich, St. Louis, Mo.) as described elsewhere (Harlow and Lane, 1998, Antibodies, Cold Spring Harbor Laboratory Press, NY).

Figure 14:
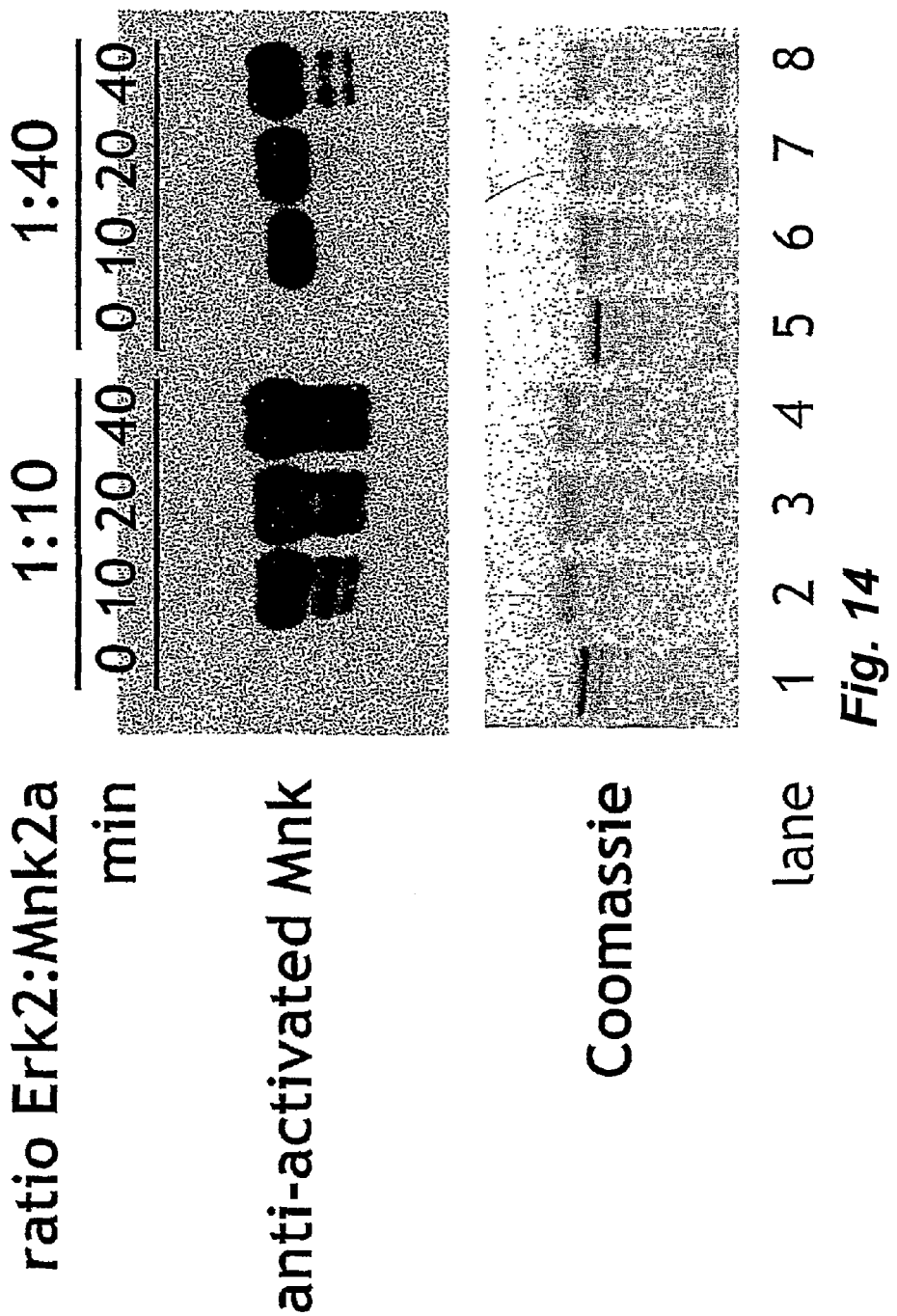
FIG. 14 shows that purified Mnk2a can be activated in vitro with a preparation of the kinases Erk2 and the double point mutant Mek1 S218D S222E.

As the reaction progresses, the activation of Mnk2a can be visualized by Mnks immuno-reactivity with the anti Phospho-Mnk antibody (see upper panel in FIG. 14). In addition, Mnk2a was visualized by Coomassie staining of the gel. Arrows indicate the Coomassie stained Mnk2a as its mobility is retarded with increasing phosphorylation (see lower panel in FIG. 14).

The generation of the phospho-epitope, essential for the activation of Mnk2a, and the high degree of efficiency of this process (as shown by the nearly complete electrophoretic mobility shift) demonstrate the suitability of this approach to produce enzymatically active Mnk2a.

For the validation of the assay, known Mnk inhibitors such as CGP57380 or CGP025088 may be used (see, Knauf et al., 2001, Mol. Cell. Biol. 21:5500, Tschopp et al., 2000, Mol Cell Biol Res Comm 3:205 and Slentz-Kesler et al., 2000, Genomics 69:63). As a negative control, CGP052088 may be used.

Alternatively, the screening may comprise the use of cellular based screening systems, e.g. prokaryotic or eukaryotic cells which overexpress Mnk proteins. Furthermore, transgenic animals capable of overexpressing or underexpressing Mnk2 and/or Mnk1 may be used.

All publications and patents mentioned in the above specification are herein incorporated by reference.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A method of screening for a candidate inhibitor of obesity that decreases the kinase activity of the Mitogen Activating Protein Kinase Interacting Kinase (Mnk) polypeptide selected from Mnk2a and Mnk2b, wherein said kinase activity is associated with obesity, said method comprising the steps of:

(a) identifying an inhibitor of the kinase activity of Mnk2a or Mnk2b by steps:
  (i) determining a first level of kinase activity of Mnk2a or Mnk2b in the absence of a candidate Mnk2 inhibitor;
  (ii) determining a second level of kinase activity of Mnk2a or Mnk2b in the presence of a candidate Mnk2 inhibitor;
  (iii) comparing the first and the second levels of the kinase activity of the Mnk2a or Mnk2b, wherein if the second level of the kinase activity is less than the first level then the candidate inhibitor is identified as an Mnk2 inhibitor; and (b) determining if the Mnk2 inhibitor identified from step (iii) increases synthesis of lipids during adipogenesis in a preadipocyte cell thereby identifying the Mnk2 inhibitor as a candidate for screening the inhibitor of obesity.

2. The method of claim 1, wherein the candidate inhibitor is selected from the group consisting of: a peptide and a small organic compound having a molecular weight of more than 50 Da and less than about 2500 Da.

3. The method of claim 1, wherein a known Mnk inhibitor is used as a control for the candidate inhibitor decreasing the kinase activity of the Mnk2a or Mnk2b polypeptide.

* * * * *

SEQUENCE LISTING

<160> NUMBER OF SEQ ID NOS: 87

<210> SEQ ID NO 1
<211> LENGTH: 1444
<212> TYPE: DNA
<213> ORGANISM: Homo sapiens

<400> SEQUENCE: 1

```
cggtcccctc ccccgctggc ggggcccgga cagaagatgg tgcagaagaa accagccgaa      60
cttcagggtt ccaccgttc gttcaagggg cagaacccct tcgagctggc ctttctccta     120
gaccagcccg accacggaga ctctgacttt ggcctgcagt gctcagcccg ccctgacatg     180
cccgccagcc agcccattga catccccgac gccaagaaga ggggcaagaa gaagaagcgc     240
ggccgggcca ccgacagctt ctcgggcagg tttgaagacg tctaccagct gcaggaagat     300
gtgctggggg agggcgctca tgcccgagtg cagacctgca tcaacctgat caccagccag     360
gagtacgccg tcaagatcat tgagaagcag ccaggccaca ttcggagcag ggttttcagg     420
gaggtggaga tgctgtacca gtgccaggga cacaggaacg tcctagagct gattgagttc     480
ttcgaggagg aggaccgctt ctacctggtg tttgagaaga tgcggggagg ctccatcctg     540
agccacatcc acaagcgccg gcacttcaac gagctggagg ccagcgtggt ggtgcaggac     600
gtggccagcg ccttggactt ctgcataac aaaggcatcg cccacaggga cctaaagccg     660
gaaaacatcc tctgtgagca ccccaaccag gtctccccg tgaagatctg tgacttcgac     720
ctgggcagcg gcatcaaact caacggggac tgctccccta tctccacccc ggagctgctc     780
actccgtgcg gctcggcgga gtacatggcc ccggaggtag tggaggcctt cagcgaggag     840
gctagcatct acgacaagcg ctgcgacctg tggagcctgg gcgtcatctt gtatatccta     900
ctcagcggct acccgcccct cgtgggccgc tgtggcagcg actgcggctg ggaccgcggc     960
gaggcctgcc ctgcctgcca gaacatgctg tttgagagca tccaggaggg caagtacgag    1020
ttccccgaca aggactgggc ccacatctcc tgcgctgcca agacctcat ctccaagctg    1080
ctggtccgtg acgccaagca gaggctgagt gccgccaag tcctgcagca ccctgggtt    1140
cagggtgcg ccccggagaa caccttgccc actcccatgg tcctgcagag aacagctgt    1200
gccaaagacc tcacgtcctt cgcggctgag gccattgcca tgaaccggca gctgccag    1260
cacgacgagg acctggctga ggaggaggcc gcggggcagg ccagcccgt cctggtccga    1320
gctacctcac gctgcctgca gctgtctcca ccctcccagt ccaagctggc gcagcggcgg    1380
caaagggcca gtctgtcctc ggccccagtg gtcctggtgg agaccacgc ctgaccctcc    1440
catc                                                                1444
```

<210> SEQ ID NO 2
<211> LENGTH: 464
<212> TYPE: PRT
<213> ORGANISM: Homo sapiens

<400> SEQUENCE: 2

```
Met Val Gln Lys Lys Pro Ala Glu Leu Gln Gly Phe His Arg Ser Phe
1               5                   10                  15

Lys Gly Gln Asn Pro Phe Glu Leu Ala Phe Ser Leu Asp Gln Pro Asp
            20                  25                  30

His Gly Asp Ser Asp Phe Gly Leu Gln Cys Ser Ala Arg Pro Asp Met
        35                  40                  45

Pro Ala Ser Gln Pro Ile Asp Ile Pro Asp Ala Lys Lys Arg Gly Lys
    50                  55                  60
```

```
Lys Lys Lys Arg Gly Arg Ala Thr Asp Ser Phe Ser Gly Arg Phe Glu
 65                  70                  75                  80

Asp Val Tyr Gln Leu Gln Glu Asp Val Leu Gly Glu Gly Ala His Ala
                 85                  90                  95

Arg Val Gln Thr Cys Ile Asn Leu Ile Thr Ser Gln Gly Tyr Ala Val
            100                 105                 110

Lys Ile Ile Glu Lys Gln Pro Gly His Ile Arg Ser Arg Val Phe Arg
        115                 120                 125

Glu Val Glu Met Leu Tyr Gln Cys Gln Gly His Arg Asn Val Leu Glu
130                 135                 140

Leu Ile Glu Phe Phe Glu Glu Asp Arg Phe Tyr Leu Val Phe Glu
145                 150                 155                 160

Lys Met Arg Gly Gly Ser Ile Leu Ser His Ile His Lys Arg Arg His
                165                 170                 175

Phe Asn Glu Leu Glu Ala Ser Val Val Val Gln Asp Val Ala Ser Ala
                180                 185                 190

Leu Asp Phe Leu His Asn Lys Gly Ile Ala His Arg Asp Leu Lys Pro
            195                 200                 205

Glu Asn Ile Leu Cys Glu His Pro Asn Gln Val Ser Pro Val Lys Ile
        210                 215                 220

Cys Asp Phe Asp Leu Gly Ser Gly Ile Lys Leu Asn Gly Asp Cys Ser
225                 230                 235                 240

Pro Ile Ser Thr Pro Glu Leu Leu Thr Pro Cys Gly Ser Ala Glu Tyr
                245                 250                 255

Met Ala Pro Glu Val Val Glu Ala Phe Ser Glu Ala Ser Ile Tyr
                260                 265                 270

Asp Lys Arg Cys Asp Leu Trp Ser Leu Gly Val Ile Leu Tyr Ile Leu
            275                 280                 285

Leu Ser Gly Tyr Pro Pro Phe Val Gly Arg Cys Gly Ser Asp Cys Gly
        290                 295                 300

Trp Asp Arg Gly Glu Ala Cys Pro Ala Cys Gln Asn Met Leu Phe Glu
305                 310                 315                 320

Ser Ile Gln Glu Gly Lys Tyr Glu Phe Pro Asp Lys Asp Trp Ala His
                325                 330                 335

Ile Ser Cys Ala Ala Lys Asp Leu Ile Ser Lys Leu Leu Val Arg Asp
            340                 345                 350

Ala Lys Gln Arg Leu Ser Ala Ala Gln Val Leu Gln His Pro Trp Val
        355                 360                 365

Gln Gly Cys Ala Pro Glu Asn Thr Leu Pro Thr Pro Met Val Leu Gln
        370                 375                 380

Arg Asn Ser Cys Ala Lys Asp Leu Thr Ser Phe Ala Ala Glu Ala Ile
385                 390                 395                 400

Ala Met Asn Arg Gln Leu Ala Gln His Asp Glu Asp Leu Ala Glu Glu
                405                 410                 415

Glu Ala Ala Gly Gln Gly Gln Pro Val Leu Val Arg Ala Thr Ser Arg
            420                 425                 430

Cys Leu Gln Leu Ser Pro Pro Ser Gln Ser Lys Leu Ala Gln Arg Arg
        435                 440                 445

Gln Arg Ala Ser Leu Ser Ser Ala Pro Val Val Leu Val Gly Asp His
        450                 455                 460

<210> SEQ ID NO 3
<211> LENGTH: 1549
```

<212> TYPE: DNA
<213> ORGANISM: Homo sapiens

<400> SEQUENCE: 3

```
gctggcgggg cccggacaga agatggtgca gaagaaacca gccgaacttc agggtttcca      60
ccgttcgttc aaggggcaga accccttcga gctggccttc tccctagacc agcccgacca     120
cggagactct gactttggcc tgcagtgctc agcccgccct gacatgcccg ccagccagcc     180
cattgacatc ccggacgcca agaagagggg caagaagaag aagcgcggcc gggccaccga     240
cagcttctcg ggcaggtttg aagacgtcta ccagctgcag aagatgtgc tggggagggg     300
cgctcatgcc cgagtgcaga cctgcatcaa cctgatcacc agccaggagt acgccgtcaa     360
gatcattgag aagcagccag gccacattcg gagcagggtt ttcagggagg tggagatgct     420
gtaccagtgc cagggacaca ggaacgtcct agagctgatt gagttcttcg aggaggagga     480
ccgcttctac ctggtgtttg agaagatgcg gggaggctcc atcctgagcc acatccacaa     540
gcgccggcac ttcaacgagc tggaggccag cgtggtggtg caggacgtgg ccagcgcctt     600
ggactttctg cataacaaag gcatcgccca cagggaccta agccggaaa acatcctctg      660
tgagcacccc aaccaggtct cccccgtgaa gatctgtgac ttcgacctgg gcagcggcat     720
caaactcaac ggggactgct cccctatctc caccccggag ctgctcactc cgtgcggctc     780
ggcggagtac atggccccgg agttagtgga ggccttcagc gaggaggcta gcatctacga     840
caagcgctgc gacctgtgga gcctgggcgt catcttgtat atcctactca gcggctaccc     900
gcccttcgtg ggccgctgtg gcagcgactg cggctgggac cgcggcgagg cctgccctgc     960
ctgccagaac atgctgtttg agagcatcca ggagggcaag tacgagttcc ccgacaagga    1020
ctgggcccac atctcctgcg ctgccaaaga cctcatctcc aagctgctgg tccgtgacgc    1080
caagcagagg ctgagtgccg cccaagtcct gcaacacccc tgggttcagg ggtgcgcccc    1140
ggagaacacc ttgcccactc ccatggtcct gcagaggtgg acagtcact tcctcctccc    1200
tccccacccc tgtcgcatcc acgtgcgacc tggaggactg gtcagaaccg ttactgtgaa    1260
tgagtgaaga tcctggagga ccctggcccc aggccagctc ccatcgctgg gggacggtga    1320
acggccatgt gttaatgtta cgatgttttt aaaagacaaa aaaaaaaaa aaaccctcaaa    1380
agttttttta aagtggggga aaacatcca agcactttaa ttccaatgta ccaggtgaac     1440
tgacggagct cagaagtttt cctttacacc aactgtcaat gccggaattt tgtattctgt    1500
tttgtaaaga tttaataaaa gtcaaaaaac ttgcaaaaaa aaaaaaaa                  1549
```

<210> SEQ ID NO 4
<211> LENGTH: 414
<212> TYPE: PRT
<213> ORGANISM: Homo sapiens

<400> SEQUENCE: 4

```
Met Val Gln Lys Lys Pro Ala Glu Leu Gln Gly Phe His Arg Ser Phe
  1               5                  10                  15

Lys Gly Gln Asn Pro Phe Glu Leu Ala Phe Ser Leu Asp Gln Pro Asp
             20                  25                  30

His Gly Asp Ser Asp Phe Gly Leu Gln Cys Ser Ala Arg Pro Asp Met
         35                  40                  45

Pro Ala Ser Gln Pro Ile Asp Ile Pro Asp Ala Lys Lys Arg Gly Lys
     50                  55                  60

Lys Lys Lys Arg Gly Arg Ala Thr Asp Ser Phe Ser Gly Arg Phe Glu
 65                  70                  75                  80
```

Asp Val Tyr Gln Leu Gln Glu Asp Val Leu Gly Gly Ala His Ala
                85                  90                  95

Arg Val Gln Thr Cys Ile Asn Leu Ile Thr Ser Gln Glu Tyr Ala Val
            100                 105                 110

Lys Ile Ile Glu Lys Gln Pro Gly His Ile Arg Ser Arg Val Phe Arg
        115                 120                 125

Glu Val Glu Met Leu Tyr Gln Cys Gln Gly His Arg Asn Val Leu Glu
    130                 135                 140

Leu Ile Glu Phe Phe Glu Glu Asp Arg Phe Tyr Leu Val Phe Glu
145                 150                 155                 160

Lys Met Arg Gly Gly Ser Ile Leu Ser His Ile His Lys Arg Arg His
                165                 170                 175

Phe Asn Glu Leu Glu Ala Ser Val Val Val Gln Asp Val Ala Ser Ala
            180                 185                 190

Leu Asp Phe Leu His Asn Lys Gly Ile Ala His Arg Asp Leu Lys Pro
        195                 200                 205

Glu Asn Ile Leu Cys Glu His Pro Asn Gln Val Ser Pro Val Lys Ile
    210                 215                 220

Cys Asp Phe Asp Leu Gly Ser Gly Ile Lys Leu Asn Gly Asp Cys Ser
225                 230                 235                 240

Pro Ile Ser Thr Pro Glu Leu Leu Thr Pro Cys Gly Ser Ala Glu Tyr
                245                 250                 255

Met Ala Pro Glu Val Val Glu Ala Phe Ser Glu Glu Ala Ser Ile Tyr
            260                 265                 270

Asp Lys Arg Cys Asp Leu Trp Ser Leu Gly Val Ile Leu Tyr Ile Leu
        275                 280                 285

Leu Ser Gly Tyr Pro Pro Phe Val Gly Arg Cys Gly Ser Asp Cys Gly
    290                 295                 300

Trp Asp Arg Gly Glu Ala Cys Pro Ala Cys Gln Asn Met Leu Phe Glu
305                 310                 315                 320

Ser Ile Gln Glu Gly Lys Tyr Glu Phe Pro Asp Lys Asp Trp Ala His
                325                 330                 335

Ile Ser Cys Ala Ala Lys Asp Leu Ile Ser Lys Leu Leu Val Arg Asp
            340                 345                 350

Ala Lys Gln Arg Leu Ser Ala Ala Gln Val Leu Gln His Pro Trp Val
        355                 360                 365

Gln Gly Cys Ala Pro Glu Asn Thr Leu Pro Thr Pro Met Val Leu Gln
    370                 375                 380

Arg Trp Asp Ser His Phe Leu Leu Pro Pro His Pro Cys Arg Ile His
385                 390                 395                 400

Val Arg Pro Gly Gly Leu Val Arg Thr Val Thr Val Asn Glu
                405                 410

<210> SEQ ID NO 5
<211> LENGTH: 2745
<212> TYPE: DNA
<213> ORGANISM: Homo sapiens

<400> SEQUENCE: 5
ggcacgaggg cgaccgctcc ccggcgggag ccagcgaagg tttccatgtc agaggccgat     60
ggagaactga agattgccac ctacgcacaa aggccattga cacttcgt gtagctggaa     120 gacaccaact tcctgacagg agctttattt catttgggat ttcaagttta cagatggtat    180
cttctcaaaa gttggaaaaa cctatagaga tgggcagtag cgaacccctt cccatcgcag    240

```
atggtgacag gaggaggaag aagaagcgga ggggccgggc cactgactcc ttgccaggaa    300
agtttgaaga tatgtacaag ctgacctctg aattgcttgg agaggagcc tatgccaaag    360 ttcaaggtgc cgtgagccta cagaatggca aagagtatgc cgtcaaaatc atcgagaaac    420
aagcagggca cagtcggagt agggtgtttc gagaggtgga cagctgtat cagtgtcagg     480 gaaacaagaa cattttggag ctgattgagt tctttgaaga tgacacaagg ttttacttgg    540
tctttgagaa attgcaagga ggttccatct tagcccacat ccagaagcaa aagcacttca    600
atgagcgaga agccagccga gtggtgcggg acgttgctgc tgcccttgac ttcctgcata    660
ccaaagacaa agtctctctc tgtcacctag gctggagtgc tatggcgcca tcagggctca    720
ctgcagcccc aacctccctg gctccagtg atcctcccac ctcagcctcc caagtagctg      780
ggactacagg cattgctcat cgtgatctga accagaaaa tatattgtgt gaatctccag     840
aaaaggtgtc tccagtgaaa atctgtgact ttgacttggg cagtgggatg aaactgaaca    900
actcctgtac ccccataacc acaccagagc tgaccacccc atgtggctct gcagaataca    960
tggcccctga ggtagtggag gtcttcacgg accaggccac attctacgac aagcgctgtg   1020
acctgtggag cctgggcgtg gtcctctaca tcatgctgag tggctacca ccctttcgtgg    1080 gtcactgcgg ggccgactgt ggctgggacc ggggcgaggt ctgcagggtg tgccagaaca   1140
agctgtttga agcatccag gaaggcaagt atgagtttcc tgacaaggac tgggcacaca    1200
tctccagtga agccaaagac ctcatctcca agctcctggt gcgagatgca aagcagagac   1260
ttagcgccgc ccaagttctg cagcacccat gggtgcaggg gcaagctcca gaaaagggac    1320
tccccacgcc gcaagtcctc cagaggaaca gcagcacaat ggacctgacg ctcttcgcag   1380
ctgaggccat cgcccttaac cgccagctat ctcagcacga agagaacgaa ctagcagagg   1440
agccagaggc actagctgat ggcctctgct ccatgaagct ttcccctccc tgcaagtcac    1500
gcctggcccg gagacgggcc ctggcccagg caggccgtgg tgaagacagg agcccgccca   1560
cagcactctg aaatgctcca gtcacacctt ataggcccta ggcctggcca ggcattgtcc   1620
cctggaaacc tgtgtggcta aagtctgctg agcaggcagc agcctctgct ctgtggctcc   1680
attcaggctt tttcatctac gaaggccctg aggttcccat caaccccca ttccctaggg    1740 tcctggagga aaaagctttt tccaaagggg ttgtctttga aaggaaagc aatcacttct    1800 cactttgcat aattgcctgc agcaggaaca tctcttcact gggctccacc tgctcacccg   1860
cctgcagatc tgggatccag cctgctctca ccgctgtagc tgtggcggct ggggctgcag   1920
cctgcaggga gaaggaagaa gcatcagttg acagaggctg ccgacacgtg cctcttcct    1980 ctcttctctg tcaccctcct ctggcggtcc ttccaccttc ctctgtcctc cggatgtcct   2040
ctttgcccgt cttctcccctt ggctgagcaa agccatcccc tcaattcagg gaagggcaag   2100
gagccttcct cattcaggaa atcaaatcag tcttccggtc tgcagcacgg aaaagcacat   2160
aatctttctt tgctgtgact gaaatgtatc cctcgtttat catccccttt gtttgtgatt    2220
gctgctaaag tcagtagtat cgttttttta aaaaaaaagt ttggtgtttt taaccatgct   2280
gttccagcaa agatgatacc ttaaactccc actgcaagcc catgaacttc ccagagagtg   2340
gaacggcttg ctcttctttc tagaatgtcc atgcacttgg gttttaatca gcagttccct   2400
attattctga ttttaagctg ttcctgtgat gaacttagag acagcatcgg tgtctgctgc   2460
tgtgtcccca ggtcttgtgt gggtggcaca gatctgggca gttagatagt gctctgtgcc   2520
taaggtgaag ccacactagg gtgaagcctc acttccctgt ttgagcaatg cagtgcctgc   2580
```

```
tgcccgtgtg catgaaggta cagccattca gataagtgga actattgagt tacataaaga    2640
aaatagattt gcatttgtca ggcagacgtt tatacaacac cacggtgctt ttatacattg    2700
tgcttatttt aataaaactg aaattctaaa aaaaaaaaaa aaaaa                    2745
```

<210> SEQ ID NO 6
<211> LENGTH: 465
<212> TYPE: PRT
<213> ORGANISM: Homo sapiens

<400> SEQUENCE: 6

```
Met Val Ser Ser Gln Lys Leu Glu Lys Pro Ile Glu Met Gly Ser Ser
1               5                   10                  15

Glu Pro Leu Pro Ile Ala Asp Gly Asp Arg Arg Lys Lys Lys Arg
            20                  25                  30

Arg Gly Arg Ala Thr Asp Ser Leu Pro Gly Lys Phe Glu Asp Met Tyr
        35                  40                  45

Lys Leu Thr Ser Glu Leu Leu Gly Glu Gly Ala Tyr Ala Lys Val Gln
50                  55                  60

Gly Ala Val Ser Leu Gln Asn Gly Lys Glu Tyr Ala Val Lys Ile Ile
65                  70                  75                  80

Glu Lys Gln Ala Gly His Ser Arg Ser Arg Val Phe Arg Glu Val Glu
                85                  90                  95

Thr Leu Tyr Gln Cys Gln Gly Asn Lys Asn Ile Leu Glu Leu Ile Glu
            100                 105                 110

Phe Phe Glu Asp Asp Thr Arg Phe Tyr Leu Val Phe Glu Lys Leu Gln
        115                 120                 125

Gly Gly Ser Ile Leu Ala His Ile Gln Lys Gln Lys His Phe Asn Glu
130                 135                 140

Arg Glu Ala Ser Arg Val Val Arg Asp Val Ala Ala Ala Leu Asp Phe
145                 150                 155                 160

Leu His Thr Lys Asp Lys Val Ser Leu Cys His Leu Gly Trp Ser Ala
                165                 170                 175

Met Ala Pro Ser Gly Leu Thr Ala Ala Pro Thr Ser Leu Gly Ser Ser
            180                 185                 190

Asp Pro Pro Thr Ser Ala Ser Gln Val Ala Gly Thr Thr Gly Ile Ala
        195                 200                 205

His Arg Asp Leu Lys Pro Glu Asn Ile Leu Cys Glu Ser Pro Glu Lys
210                 215                 220

Val Ser Pro Val Lys Ile Cys Asp Phe Asp Leu Gly Ser Gly Met Lys
225                 230                 235                 240

Leu Asn Asn Ser Cys Thr Pro Ile Thr Thr Pro Glu Leu Thr Thr Pro
                245                 250                 255

Cys Gly Ser Ala Glu Tyr Met Ala Pro Glu Val Val Glu Val Phe Thr
            260                 265                 270

Asp Gln Ala Thr Phe Tyr Asp Lys Arg Cys Asp Leu Trp Ser Leu Gly
        275                 280                 285

Val Val Leu Tyr Ile Met Leu Ser Gly Tyr Pro Pro Phe Val Gly His
290                 295                 300

Cys Gly Ala Asp Cys Gly Trp Asp Arg Gly Glu Val Cys Arg Val Cys
305                 310                 315                 320

Gln Asn Lys Leu Phe Glu Ser Ile Gln Glu Gly Lys Tyr Glu Phe Pro
                325                 330                 335

Asp Lys Asp Trp Ala His Ile Ser Ser Glu Ala Lys Asp Leu Ile Ser
            340                 345                 350
```

```
Lys Leu Leu Val Arg Asp Ala Lys Gln Arg Leu Ser Ala Ala Gln Val
            355                 360                 365

Leu Gln His Pro Trp Val Gly Gln Ala Pro Glu Lys Gly Leu Pro
    370                 375                 380

Thr Pro Gln Val Leu Gln Arg Asn Ser Ser Thr Met Asp Leu Thr Leu
385                 390                 395                 400

Phe Ala Ala Glu Ala Ile Ala Leu Asn Arg Gln Leu Ser Gln His Glu
                405                 410                 415

Glu Asn Glu Leu Ala Glu Glu Pro Glu Ala Leu Ala Asp Gly Leu Cys
            420                 425                 430

Ser Met Lys Leu Ser Pro Pro Cys Lys Ser Arg Leu Ala Arg Arg
            435                 440                 445

Ala Leu Ala Gln Ala Gly Arg Gly Glu Asp Arg Ser Pro Pro Thr Ala
    450                 455                 460

Leu
465

<210> SEQ ID NO 7
<211> LENGTH: 1253
<212> TYPE: DNA
<213> ORGANISM: Drosophila melanogaster
<220> FEATURE:
<221> NAME/KEY: misc_feature
<222> LOCATION: (5)..(5)
<223> OTHER INFORMATION: n is a, c, g, or t

<400> SEQUENCE: 7
cgagnaagtg ttactatcta aacacatttc aaacaattct taacaaacaa ttccaaacat      60
acaattccac ttaccactta ccgaccaaat tacgagttta caatggacaa agctgaacgc     120
gactactggc atcttcgatc cttggaaatc gaagaggagc cgcgatttcc gccaacaaac     180
gtcgctgatc cactaaccgc acgcaatctg ttccagctct acgtcaacac cttcattgga     240
gccaatctgg ccgagtcgtg tgttttccca ttggacgtgg ccaagacccg gatgcaggta     300
gatggcgagc aggccaagaa gacgggtaaa gcgatgccaa ctttccgtgc aactcttacc     360
aacatgatcc gagtggaggg attcaagtcg ctctacgccg gcttctcggc aatggtgacc     420
cgaaacttta tcttcaactc gttacgtgtt gttctctacg acgttttccg gcgccctttt     480
ctctaccaga acgaacggaa cgaggaagtg ctcaagatct acatggcgct gggatgcagc     540
ttcaccgcag gctgcattgc ccaggcactg gccaatccct tgacatcgt caaggtgcga     600 atgcagacgg aaggacgccg ccgccagctg ggctatgatg tgcgggtgaa cagcatggtg     660
caggccttcg tggacatcta ccgccgtggc ggactgccca gtatgtggaa gggtgtaggg     720
cccagctgca tgcgtgcctg cctgatgacg accggcgatg tgggcagtta cgatatcagt     780
aagcgcacct tcaagcgcct gctggacttg gaggaaggcc tgccactgcg tttcgtgtct     840
tccatgtgcg ccggactaac ggcatccgtg ctcagcacgc cggcgaacgt gatcaagtcg     900
cggatgatga accagccggt gaacgagagc ggcaagaatc tgtactacaa gaactccctc     960
gactgcatta ggaagctggt cagggaggag ggtgtcctca cgttgtataa gggcctcatg    1020
cccacttggt ttcgcctggg accgttctca gtgctctttt ggctgtccgt cgagcagctg    1080
cgtcagtgga aaggccagag tggattttag gagcaaacta tcaatcttac tatcgtattt    1140
tgtatgtctt ttaacacgca ataaaaaggg tgcaagtcaa accatctatt atacatatta    1200
taaatataac tttaatccca aaaaaaaaaa aaaaaactcg tgccgaattc gat           1253
```

<210> SEQ ID NO 8
<211> LENGTH: 335
<212> TYPE: PRT
<213> ORGANISM: Drosophila melanogaster

<400> SEQUENCE: 8

Met Asp Lys Ala Glu Arg Asp Tyr Trp His Leu Arg Ser Leu Glu Ile
1               5                   10                  15

Glu Glu Glu Pro Arg Phe Pro Pro Thr Asn Val Ala Asp Pro Leu Thr
            20                  25                  30

Ala Arg Asn Leu Phe Gln Leu Tyr Val Asn Thr Phe Ile Gly Ala Asn
        35                  40                  45

Leu Ala Glu Ser Cys Val Phe Pro Leu Asp Val Ala Lys Thr Arg Met
    50                  55                  60

Gln Val Asp Gly Glu Gln Ala Lys Lys Thr Gly Lys Ala Met Pro Thr
65                  70                  75                  80

Phe Arg Ala Thr Leu Thr Asn Met Ile Arg Val Glu Gly Phe Lys Ser
                85                  90                  95

Leu Tyr Ala Gly Phe Ser Ala Met Val Thr Arg Asn Phe Ile Phe Asn
            100                 105                 110

Ser Leu Arg Val Val Leu Tyr Asp Val Phe Arg Arg Pro Phe Leu Tyr
        115                 120                 125

Gln Asn Glu Arg Asn Glu Glu Val Leu Lys Ile Tyr Met Ala Leu Gly
    130                 135                 140

Cys Ser Phe Thr Ala Gly Cys Ile Ala Gln Ala Leu Ala Asn Pro Phe
145                 150                 155                 160

Asp Ile Val Lys Val Arg Met Gln Thr Glu Gly Arg Arg Gln Leu
                165                 170                 175

Gly Tyr Asp Val Arg Val Asn Ser Met Val Gln Ala Phe Val Asp Ile
            180                 185                 190

Tyr Arg Arg Gly Gly Leu Pro Ser Met Trp Lys Gly Val Gly Pro Ser
        195                 200                 205

Cys Met Arg Ala Cys Leu Met Thr Thr Gly Asp Val Gly Ser Tyr Asp
210                 215                 220

Ile Ser Lys Arg Thr Phe Lys Arg Leu Leu Asp Leu Glu Glu Gly Leu
225                 230                 235                 240

Pro Leu Arg Phe Val Ser Ser Met Cys Ala Gly Leu Thr Ala Ser Val
                245                 250                 255

Leu Ser Thr Pro Ala Asn Val Ile Lys Ser Arg Met Met Asn Gln Pro
            260                 265                 270

Val Asn Glu Ser Gly Lys Asn Leu Tyr Tyr Lys Asn Ser Leu Asp Cys
        275                 280                 285

Ile Arg Lys Leu Val Arg Glu Glu Gly Val Leu Thr Leu Tyr Lys Gly
    290                 295                 300

Leu Met Pro Thr Trp Phe Arg Leu Gly Pro Phe Ser Val Leu Phe Trp
305                 310                 315                 320

Leu Ser Val Glu Gln Leu Arg Gln Trp Lys Gly Gln Ser Gly Phe
                325                 330                 335

<210> SEQ ID NO 9
<211> LENGTH: 24
<212> TYPE: DNA
<213> ORGANISM: Drosophila melanogaster

<400> SEQUENCE: 9

```
ctaaacaaac aattccaaac atag                                          24

<210> SEQ ID NO 10
<211> LENGTH: 24
<212> TYPE: DNA
<213> ORGANISM: Drosophila melanogaster

<400> SEQUENCE: 10
aaaagacata gaaaatacga tagt                                          24

<210> SEQ ID NO 11
<211> LENGTH: 18
<212> TYPE: DNA
<213> ORGANISM: Mus musculus

<400> SEQUENCE: 11
gctgagggcc tctgctcc                                                 18

<210> SEQ ID NO 12
<211> LENGTH: 16
<212> TYPE: DNA
<213> ORGANISM: Mus musculus

<400> SEQUENCE: 12
tcgccttcga gccagg                                                   16

<210> SEQ ID NO 13
<211> LENGTH: 27
<212> TYPE: DNA
<213> ORGANISM: Mus musculus
<220> FEATURE:
<221> NAME/KEY: misc_feature
<222> LOCATION: (1)..(1)
<223> OTHER INFORMATION: FAM reporter dye
<220> FEATURE:
<221> NAME/KEY: misc_feature
<222> LOCATION: (27)..(27)
<223> OTHER INFORMATION: TAMRA quencher dye

<400> SEQUENCE: 13
tgaagctgtc ccctccatcc aaatctc                                       27

<210> SEQ ID NO 14
<211> LENGTH: 19
<212> TYPE: DNA
<213> ORGANISM: Mus musculus

<400> SEQUENCE: 14
tgcacttgat tgaccccga                                                19

<210> SEQ ID NO 15
<211> LENGTH: 22
<212> TYPE: DNA
<213> ORGANISM: Mus musculus

<400> SEQUENCE: 15
tttctgattg tcaaccctcc aa                                            22

<210> SEQ ID NO 16
<211> LENGTH: 24
<212> TYPE: DNA
<213> ORGANISM: Mus musculus
<220> FEATURE:
<221> NAME/KEY: misc_feature
<222> LOCATION: (1)..(1)
<223> OTHER INFORMATION: FAM reporter dye
```

```
<220> FEATURE:
<221> NAME/KEY: misc_feature
<222> LOCATION: (24)..(24)
<223> OTHER INFORMATION: TAMRA quencher dye

<400> SEQUENCE: 16
ccccatcatc cacctgcagt gtcc                                          24

<210> SEQ ID NO 17
<211> LENGTH: 23
<212> TYPE: DNA
<213> ORGANISM: Homo sapiens

<400> SEQUENCE: 17
ccatctcccc ctctgtacat agg                                           23

<210> SEQ ID NO 18
<211> LENGTH: 19
<212> TYPE: DNA
<213> ORGANISM: Homo sapiens

<400> SEQUENCE: 18
ccggctggcg atagcttaa                                                19

<210> SEQ ID NO 19
<211> LENGTH: 27
<212> TYPE: DNA
<213> ORGANISM: Homo sapiens
<220> FEATURE:
<221> NAME/KEY: misc_feature
<222> LOCATION: (1)..(1)
<223> OTHER INFORMATION: FAM reporter dye
<220> FEATURE:
<221> NAME/KEY: misc_feature
<222> LOCATION: (27)..(27)
<223> OTHER INFORMATION: TAMRA quencher dye

<400> SEQUENCE: 19
cacccgtccc ccaatcaaat ctaaagg                                       27

<210> SEQ ID NO 20
<211> LENGTH: 26
<212> TYPE: DNA
<213> ORGANISM: Homo sapiens

<400> SEQUENCE: 20
ttactgtgaa tgagtgaaga tcctgg                                        26

<210> SEQ ID NO 21
<211> LENGTH: 17
<212> TYPE: DNA
<213> ORGANISM: Homo sapiens

<400> SEQUENCE: 21
atggccgttc accgtcc                                                  17

<210> SEQ ID NO 22
<211> LENGTH: 21
<212> TYPE: DNA
<213> ORGANISM: Homo sapiens
<220> FEATURE:
<221> NAME/KEY: misc_feature
<222> LOCATION: (1)..(1)
<223> OTHER INFORMATION: FAM reporter dye
<220> FEATURE:
<221> NAME/KEY: misc_feature
<222> LOCATION: (21)..(21)
```

<223> OTHER INFORMATION: TAMRA quencher dye

<400> SEQUENCE: 22
ccaggccagc tcccatcgct g                                    21

<210> SEQ ID NO 23
<211> LENGTH: 21
<212> TYPE: DNA
<213> ORGANISM: Mus musculus

<400> SEQUENCE: 23
aagttggcct tcgcgttaga c                                    21

<210> SEQ ID NO 24
<211> LENGTH: 20
<212> TYPE: DNA
<213> ORGANISM: Mus musculus

<400> SEQUENCE: 24
cgatatgtac aaggagctag                                      20

<210> SEQ ID NO 25
<211> LENGTH: 44
<212> TYPE: DNA
<213> ORGANISM: Mus musculus

<400> SEQUENCE: 25
ctcccccatc tccgcaccag agctgctcgc cccgtgtggg tcag            44

<210> SEQ ID NO 26
<211> LENGTH: 41
<212> TYPE: DNA
<213> ORGANISM: Mus musculus

<400> SEQUENCE: 26
ctgacccaca cggggcgagc tctggtgcgg agatgggggga g              41

<210> SEQ ID NO 27
<211> LENGTH: 19
<212> TYPE: DNA
<213> ORGANISM: Mus musculus

<400> SEQUENCE: 27
gctgctggtc cgagatgcc                                       19

<210> SEQ ID NO 28
<211> LENGTH: 18
<212> TYPE: DNA
<213> ORGANISM: Mus musculus

<400> SEQUENCE: 28
gggtcatgcg cgatcccc                                        18

<210> SEQ ID NO 29
<211> LENGTH: 22
<212> TYPE: DNA
<213> ORGANISM: Mus musculus

<400> SEQUENCE: 29
cagcgtggta gtacaggacg tg                                   22

<210> SEQ ID NO 30
<211> LENGTH: 16

```
<212> TYPE: DNA
<213> ORGANISM: Mus musculus

<400> SEQUENCE: 30
tccctgtggg cgatgc                                                     16

<210> SEQ ID NO 31
<211> LENGTH: 27
<212> TYPE: DNA
<213> ORGANISM: Mus musculus

<400> SEQUENCE: 31
cagtgccctg gacttcctgc ataacaa                                         27

<210> SEQ ID NO 32
<211> LENGTH: 19
<212> TYPE: DNA
<213> ORGANISM: Mus musculus

<400> SEQUENCE: 32
acatcagccc acagtgtga                                                  19

<210> SEQ ID NO 33
<211> LENGTH: 21
<212> TYPE: DNA
<213> ORGANISM: Mus musculus

<400> SEQUENCE: 33
tctccattga gtttgatacc a                                               21

<210> SEQ ID NO 34
<211> LENGTH: 27
<212> TYPE: DNA
<213> ORGANISM: Mus musculus
<220> FEATURE:
<221> NAME/KEY: misc_feature
<222> LOCATION: (1)..(6)
<223> OTHER INFORMATION: non priming nucleotides/ attached EcoR1

<400> SEQUENCE: 34
cggaatccac tagctccttg tacatat                                         27

<210> SEQ ID NO 35
<211> LENGTH: 29
<212> TYPE: DNA
<213> ORGANISM: Mus musculus
<220> FEATURE:
<221> NAME/KEY: misc_feature
<222> LOCATION: (1)..(8)
<223> OTHER INFORMATION: non priming nucleotides/ attached Cla1

<400> SEQUENCE: 35
ccatcgatgg aactcgtatt gcatagtag                                       29

<210> SEQ ID NO 36
<211> LENGTH: 23
<212> TYPE: DNA
<213> ORGANISM: Mus musculus

<400> SEQUENCE: 36
agactaggga ggagggtgga gga                                             23

<210> SEQ ID NO 37
<211> LENGTH: 22
<212> TYPE: DNA
```

<210> SEQ ID NO 38
<211> LENGTH: 21
<212> TYPE: DNA
<213> ORGANISM: Mus musculus

<400> SEQUENCE: 38
ggtggatgtg aatgtgtgc ga                                             22

<210> SEQ ID NO 38
<211> LENGTH: 21
<212> TYPE: DNA
<213> ORGANISM: Mus musculus

<400> SEQUENCE: 38
ggggtgtagg ggtctgttag g                                             21

<210> SEQ ID NO 39
<211> LENGTH: 424
<212> TYPE: PRT
<213> ORGANISM: Homo sapiens

<400> SEQUENCE: 39

```
Met Val Ser Ser Gln Lys Leu Glu Lys Pro Ile Glu Met Gly Ser Ser
  1               5                  10                  15
Glu Pro Leu Pro Ile Ala Asp Gly Asp Arg Arg Lys Lys Lys Arg
             20                  25                  30
Arg Gly Arg Ala Thr Asp Ser Leu Pro Gly Lys Phe Glu Asp Met Tyr
         35                  40                  45
Lys Leu Thr Ser Glu Leu Leu Gly Glu Gly Ala Tyr Ala Lys Val Gln
     50                  55                  60
Gly Ala Val Ser Leu Gln Asn Gly Lys Glu Tyr Ala Val Lys Ile Ile
 65                  70                  75                  80
Glu Lys Gln Ala Gly His Ser Arg Ser Arg Val Phe Arg Glu Val Glu
                 85                  90                  95
Thr Leu Tyr Gln Cys Gln Gly Asn Lys Asn Ile Leu Glu Leu Ile Glu
            100                 105                 110
Phe Phe Glu Asp Asp Thr Arg Phe Tyr Leu Val Phe Glu Lys Leu Gln
        115                 120                 125
Gly Gly Ser Ile Leu Ala His Ile Gln Lys Gln Lys His Phe Asn Glu
    130                 135                 140
Arg Glu Ala Ser Arg Val Val Arg Asp Val Ala Ala Ala Leu Asp Phe
145                 150                 155                 160
Leu His Thr Lys Gly Ile Ala His Arg Asp Leu Lys Pro Glu Asn Ile
                165                 170                 175
Leu Cys Glu Ser Pro Glu Lys Val Ser Pro Val Lys Ile Cys Asp Phe
            180                 185                 190
Asp Leu Gly Ser Gly Met Lys Leu Asn Asn Ser Cys Thr Pro Ile Thr
        195                 200                 205
Thr Pro Glu Leu Thr Thr Pro Cys Gly Ser Ala Glu Tyr Met Ala Pro
    210                 215                 220
Glu Val Val Glu Val Phe Thr Asp Gln Ala Thr Phe Tyr Asp Lys Arg
225                 230                 235                 240
Cys Asp Leu Trp Ser Leu Gly Val Val Leu Tyr Ile Met Leu Ser Gly
                245                 250                 255
Tyr Pro Pro Phe Val Gly His Cys Gly Ala Asp Cys Gly Trp Asp Arg
            260                 265                 270
Gly Glu Val Cys Arg Val Cys Gln Asn Lys Leu Phe Glu Ser Ile Gln
        275                 280                 285
Glu Gly Lys Tyr Glu Phe Pro Asp Lys Asp Trp Ala His Ile Ser Ser
```

```
                290                 295                 300

Glu Ala Lys Asp Leu Ile Ser Lys Leu Leu Val Arg Asp Ala Lys Gln
305                 310                 315                 320

Arg Leu Ser Ala Ala Gln Val Leu Gln His Pro Trp Val Gln Gly Gln
                325                 330                 335

Ala Pro Glu Lys Gly Leu Pro Thr Pro Gln Val Leu Gln Arg Asn Ser
                340                 345                 350

Ser Thr Met Asp Leu Thr Leu Phe Ala Ala Glu Ala Ile Ala Leu Asn
            355                 360                 365

Arg Gln Leu Ser Gln His Glu Glu Asn Glu Leu Ala Glu Glu Pro Glu
        370                 375                 380

Ala Leu Ala Asp Gly Leu Cys Ser Met Lys Leu Ser Pro Pro Cys Lys
385                 390                 395                 400

Ser Arg Leu Ala Arg Arg Arg Ala Leu Ala Gln Ala Gly Arg Gly Glu
                405                 410                 415

Asp Arg Ser Pro Pro Thr Ala Leu
                420

<210> SEQ ID NO 40
<211> LENGTH: 1131
<212> TYPE: PRT
<213> ORGANISM: Drosophila melanogaster

<400> SEQUENCE: 40

Met Val Glu Pro Lys Ser Gly Thr Ala Ala Ser Ala Ala Ala Ala Lys
1               5                   10                  15

Ala Ser Asn Asn Asn Asn Asn His Pro Arg Gly Ser Gly Asp Ser
            20                  25                  30

Gly Ile Arg Ser Gly Ser Gly Ile Ser Cys Ser Asn Thr Asp Asn Ser
        35                  40                  45

Cys Ser Gln Ser Gln Ser Asp Gly Gln Asn Glu Leu Thr Arg Tyr Ser
    50                  55                  60

Ser Glu Asp Val Ser Gly Asn Glu Ser Ser Glu Ala Pro Asn Met Thr
65                  70                  75                  80

Glu Val Glu Arg Gln Ala Glu Leu Asn Arg His Lys Glu Glu Met Gln
                85                  90                  95

Lys Lys Arg Arg Lys Lys Arg Ile Ser Ser Ser Leu His Ser Ser Thr
            100                 105                 110

Phe Gln Glu Leu Tyr Lys Leu Thr Gly Glu Ile Leu Gly Glu Gly Ala
        115                 120                 125

Tyr Ala Ser Val Gln Thr Cys Val Asn Ile Tyr Thr Asp Leu Glu Tyr
    130                 135                 140

Ala Val Lys Val Ile Asp Lys Ile Pro Gly His Ala Arg Ala Arg Val
145                 150                 155                 160

Phe Arg Glu Val Glu Thr Phe His His Cys Gln Gly His Leu Gly Ile
                165                 170                 175

Leu Gln Leu Ile Glu Phe Phe Glu Asp Asp Lys Lys Phe Tyr Leu Val
            180                 185                 190

Phe Glu Lys Ile Asn Gly Gly Pro Leu Leu Ser Arg Ile Gln Glu His
        195                 200                 205

Ile Cys Phe Ser Glu His Glu Pro Ser Gln Ile Ile Lys Glu Ile Ala
    210                 215                 220

Ser Gly Leu Asp Phe Leu His Lys Lys Gly Ile Ala His Arg Asp Leu
225                 230                 235                 240
```

-continued

Lys Pro Glu Asn Ile Leu Cys Val Lys Thr Asp Ser Leu Cys Pro Ile
                245                 250                 255

Lys Ile Cys Asp Phe Asp Leu Gly Ser Gly Ile Lys Phe Thr Thr Asp
        260                 265                 270

Ile Ser Ser Pro Ala Ala Thr Pro Gln Leu Leu Thr Pro Val Gly Ser
    275                 280                 285

Ala Glu Phe Met Ala Pro Glu Val Val Asp Leu Phe Val Gly Glu Ala
290                 295                 300

His Tyr Tyr Asp Lys Arg Cys Asp Leu Trp Ser Leu Gly Val Ile Ala
305                 310                 315                 320

Tyr Ile Leu Leu Cys Gly Tyr Pro Pro Phe Ser Gly Asn Cys Gly Glu
                325                 330                 335

Asp Cys Gly Trp Asn Arg Gly Glu Asn Cys Arg Thr Cys Gln Glu Leu
        340                 345                 350

Leu Phe Glu Ser Ile Gln Glu Gly His Phe Ser Phe Pro Glu Ala Glu
    355                 360                 365

Trp His Asp Val Ser Asp Glu Ala Lys Asp Leu Ile Ser Asn Leu Leu
370                 375                 380

Val Lys Lys Ala Ser Asn Arg Leu Ser Ala Glu Ala Val Leu Asn His
385                 390                 395                 400

Pro Trp Ile Arg Met Cys Glu Gln Glu Pro Pro Ala Ser Lys His Gly
                405                 410                 415

Arg Arg His Lys Ala Leu Gln Thr Pro Ser Asn Ile Arg Arg Asn His
        420                 425                 430

Gln Ser Ala Arg Glu Ile Ser Gln Phe Ala Glu Ser Ala Met Ala Val
    435                 440                 445

Lys Arg Val Val Leu Gln His Phe Ser Met Arg Tyr Asp Tyr Met Lys
450                 455                 460

Glu Arg Pro Asn Ile Tyr Gln Pro Ser Gln Ala Tyr Met Asp Ala Tyr
465                 470                 475                 480

Ser Asp Glu Asn Tyr Asn Pro Lys Pro Pro Gly His Tyr Thr Arg Asn
                485                 490                 495

Arg Ser Gln Arg Asn Pro Ala Ser Ser Leu Cys Gly Tyr Gly Gly Arg
        500                 505                 510

Met Ser Ser Met His Gly Gln Arg Ala Asn Ser Arg Arg Ser Ser Arg
    515                 520                 525

Asn Ala Ser Arg Asn Ala Ser Ala Ile Tyr Pro Asn Ser Gly Gly Phe
530                 535                 540

Lys Thr Leu Asn Val His Glu Glu Asp Asp Asp Glu Gly Leu Glu
545                 550                 555                 560

Ala Phe Gly His Ile Asp Asp Asp Glu Trp Ser Arg Ser Arg Arg
                565                 570                 575

Glu Tyr Gln Gln Gln Cys Glu Thr Leu Gly Glu Asp Arg Phe Arg Arg
        580                 585                 590

Gln Ser Gly Ser Glu Gly Asp Glu Val Glu Asp Glu Asp Gly Glu
    595                 600                 605

Asn Glu Asp Tyr Gln His Tyr Lys His Tyr Trp Arg Glu Leu Asp Glu
610                 615                 620

Glu Glu Gly Asp Asp Tyr Leu Tyr Glu Gln Gln Arg Val Asp Asp
625                 630                 635                 640

Lys Phe Gly Glu Glu Glu Phe Glu Asp Glu Pro Lys Glu Glu Thr Gln
                645                 650                 655

Ala Asp Asn Leu Lys Leu Ser Lys Ala Tyr Val Glu Gln Val Gly Glu

```
                660               665               670
Thr Asn Val Glu Lys Ser Lys Pro Gln Asp Asp Asn Gly Gly Tyr Ile
            675               680               685
Arg Glu Asp Leu Ile Met Asp Asn Met Asp Met Lys Lys Asn Thr Gln
        690               695               700
Gln Ser Glu Phe Ala Lys Leu Thr Ile Met Arg Asn Asp Ala Gln Thr
705               710               715               720
Glu Glu Asn Lys Ile Met Gln Gln Gln Asp Glu Glu Lys Lys Glu Asp
                725               730               735
Lys Gln Gln Asp Asp Val Asp Gly Ala Lys Lys Gln Gly Pro Ser Ser
            740               745               750
Asp Ile Ser Ala Thr Thr Ile Thr Asp Asn Asn Lys Leu Gln Thr Pro
        755               760               765
Val Met Thr Thr Thr His Ile Asn Asn Trp Thr Gly Asp Ala Ile
        770               775               780
Glu Asp Asp Asp Val Lys Leu Leu Asp Ser Ile Ser Asp Leu Asn Glu
785               790               795               800
Lys Leu Pro Glu Ile Tyr Glu Thr Ala Asn Ile Val Val Asn Ser Ala
                805               810               815
Ala Val Pro Ala Ala Ser Thr Pro Ala Ala Ser Ala Thr Arg Pro Pro
            820               825               830
Thr Asp Asn Pro Glu Glu Asp Asp Ser Asn Val Thr Lys Pro Thr Thr
        835               840               845
Thr Ala Glu Gly Thr Thr Met Gln Thr Thr Phe Gly Met Ser Ala Glu
        850               855               860
Glu Glu Lys Pro Val Ala Leu Ser His Thr Ala Gly His His Ser Lys
865               870               875               880
Thr Gly Arg Thr Val Asn Phe Ala Pro Asp Ala Tyr Gln Asn Asp Glu
                885               890               895
Asp Ala Asp Ile Asp Glu Asp Asp Tyr Asp Asp Glu Glu Asn Leu
            900               905               910
His Glu His Ser Lys Gln Gln Leu Pro Ser Asn Ala Tyr Thr Arg Lys
        915               920               925
Gln Arg Gln Gln His Gln Arg Tyr Ile Val Pro Arg Tyr Gln Leu Ala
        930               935               940
Asp Gln Val Pro Gln Arg Gln His Thr Glu Asn Trp Arg Tyr Arg Thr
945               950               955               960
His His Ser Gln Glu Gln Gln Pro Thr Ala Asp Tyr Arg Lys Tyr Arg
                965               970               975
Pro Pro Phe Ser Thr Gly Gly Gly Gly His His Gly Asn Leu Gln
            980               985               990
Arg Asn Tyr Leu Gly Ser Phe Ser  His Ser Gly Gly Ala  Ala Gly Tyr
        995               1000              1005
Lys Ile Asn Ser Pro Pro Cys  Val Gln Arg Arg Ile  Met Asp Ala
        1010              1015              1020
Pro Met  Pro Pro Ala Gly Ser  Ser Gly Ser Asp Glu  Gln Ser Tyr
        1025              1030              1035
Ala Arg  Ser Cys His Asn Arg  Ser Ser Gly Ser Gly  Arg Phe Glu
        1040              1045              1050
Leu Pro  Asp Met Pro Met Gln  Pro Pro Ser Gly Ser  Gly Ser Ala
        1055              1060              1065
Ile Arg  Asn Trp Gly Met Asn  Gln Gly Gly Gln Arg  Val Gln Ala
        1070              1075              1080
```

His Leu Gln Ala Arg Ile Gly Leu Ser Pro Arg His Gly Gly Ser
    1085                1090                1095

Arg Gln Asp Pro Glu Gln Gln Gln Pro Ala Gln Leu Pro Pro Ser
    1100                1105                1110

Glu Ser Val Leu Leu Gln Asn Asp Leu Ser Glu Val Arg Gly Ser
    1115                1120                1125

Thr Val Asp
    1130

<210> SEQ ID NO 41
<211> LENGTH: 433
<212> TYPE: PRT
<213> ORGANISM: Homo sapiens

<400> SEQUENCE: 41

Arg Arg Leu Arg Gln Gln Gln Arg Ala Leu Arg Ala Gly His Arg Gln
1               5                   10                  15

Trp Leu Arg Met Val Gln Lys Lys Pro Ala Glu Leu Gln Gly Phe His
                20                  25                  30

Arg Ser Phe Lys Gly Gln Asn Pro Phe Glu Leu Ala Phe Ser Leu Asp
            35                  40                  45

Gln Pro Asp His Gly Asp Ser Asp Phe Gly Leu Gln Cys Ser Ala Arg
        50                  55                  60

Pro Asp Met Pro Ala Ser Gln Pro Ile Asp Ile Pro Asp Ala Lys Lys
65                  70                  75                  80

Arg Gly Lys Lys Lys Arg Gly Arg Ala Thr Asp Ser Phe Ser Gly
                85                  90                  95

Arg Phe Glu Asp Val Tyr Gln Leu Gln Glu Asp Val Leu Gly Glu Gly
            100                 105                 110

Ala His Ala Arg Val Gln Thr Cys Ile Asn Leu Ile Thr Ser Gln Glu
        115                 120                 125

Tyr Ala Val Lys Ile Ile Glu Lys Gln Pro Gly His Ile Arg Ser Arg
    130                 135                 140

Val Phe Arg Glu Val Glu Met Leu Tyr Gln Cys Gln Gly His Arg Asn
145                 150                 155                 160

Val Leu Glu Leu Ile Glu Phe Phe Glu Glu Glu Asp Arg Phe Tyr Leu
                165                 170                 175

Val Phe Glu Lys Met Arg Gly Gly Ser Ile Leu Ser His Ile His Lys
            180                 185                 190

Arg Arg His Phe Asn Glu Leu Glu Ala Ser Val Val Gln Asp Val
        195                 200                 205

Ala Ser Ala Leu Asp Phe Leu His Asn Lys Gly Ile Ala His Arg Asp
    210                 215                 220

Leu Lys Pro Glu Asn Ile Leu Cys Glu His Pro Asn Gln Val Ser Pro
225                 230                 235                 240

Val Lys Ile Cys Asp Phe Asp Leu Gly Ser Gly Ile Lys Leu Asn Gly
                245                 250                 255

Asp Cys Ser Pro Ile Ser Thr Pro Glu Leu Leu Thr Pro Cys Gly Ser
            260                 265                 270

Ala Glu Tyr Met Ala Pro Glu Val Glu Ala Phe Ser Glu Glu Ala
        275                 280                 285

Ser Ile Tyr Asp Lys Arg Cys Asp Leu Trp Ser Leu Gly Val Ile Leu
    290                 295                 300

Tyr Ile Leu Leu Ser Gly Tyr Pro Pro Phe Val Gly Arg Cys Gly Ser

```
                305                 310                 315                 320
Asp Cys Gly Trp Asp Arg Gly Glu Ala Cys Pro Ala Cys Gln Asn Met
                325                 330                 335

Leu Phe Glu Ser Ile Gln Glu Gly Lys Tyr Glu Phe Pro Asp Lys Asp
                340                 345                 350

Trp Ala His Ile Ser Cys Ala Ala Lys Asp Leu Ile Ser Lys Leu Leu
                355                 360                 365

Val Arg Asp Ala Lys Gln Arg Leu Ser Ala Ala Gln Val Leu Gln His
                370                 375                 380

Pro Trp Val Gln Gly Cys Ala Pro Glu Asn Thr Leu Pro Thr Pro Met
385                 390                 395                 400

Val Leu Gln Arg Trp Asp Ser His Phe Leu Leu Pro Pro His Pro Cys
                405                 410                 415

Arg Ile His Val Arg Pro Gly Gly Leu Val Arg Thr Val Thr Val Asn
                420                 425                 430

Glu

<210> SEQ ID NO 42
<211> LENGTH: 48
<212> TYPE: DNA
<213> ORGANISM: Mus musculus

<400> SEQUENCE: 42
ccttagacct cggcccagca cagggaagcc cgacctggtg agcccccca                  48

<210> SEQ ID NO 43
<211> LENGTH: 48
<212> TYPE: DNA
<213> ORGANISM: Mus musculus

<400> SEQUENCE: 43
ctcttctcta cagacatgcc ttccgcaggt tcgaaggtga gctgcaga                   48

<210> SEQ ID NO 44
<211> LENGTH: 48
<212> TYPE: DNA
<213> ORGANISM: Mus musculus

<400> SEQUENCE: 44
ctcgcattcc agatgtctat cagctatgct gtcaagagct ggggtctg                   48

<210> SEQ ID NO 45
<211> LENGTH: 48
<212> TYPE: DNA
<213> ORGANISM: Mus musculus

<400> SEQUENCE: 45
cctacattgt agatcattga gaagcaggga cataggtaag gtggcctg                   48

<210> SEQ ID NO 46
<211> LENGTH: 49
<212> TYPE: DNA
<213> ORGANISM: Mus musculus

<400> SEQUENCE: 46
tcccaactca ggaatgttct agaagaagat gcgtggcggt aggtactgg                  49

<210> SEQ ID NO 47
<211> LENGTH: 48
<212> TYPE: DNA
```

<213> ORGANISM: Nus musculus

<400> SEQUENCE: 47
ctggcctgca caggatccat cctagcataa caaaggtgtg gcagggac        48

<210> SEQ ID NO 48
<211> LENGTH: 48
<212> TYPE: DNA
<213> ORGANISM: Mus musculus

<400> SEQUENCE: 48
cacctcacta ggcatcgccc acagccccaa ccaggtgagg ctgcctga        48

<210> SEQ ID NO 49
<211> LENGTH: 48
<212> TYPE: DNA
<213> ORGANISM: Mus musculus

<400> SEQUENCE: 49
ccattcccag gtctcgccag tgaagctgct caccccggtg agggcagt        48

<210> SEQ ID NO 50
<211> LENGTH: 48
<212> TYPE: DNA
<213> ORGANISM: Mus musculus

<400> SEQUENCE: 50
ccctgcccca cagtgtgggt cagctgggtg caggggtaa gccttggg         48

<210> SEQ ID NO 51
<211> LENGTH: 48
<212> TYPE: DNA
<213> ORGANISM: Mus musculus

<400> SEQUENCE: 51
gacttcttac agtgtgcccc agagttggtt ctgcagaggt gaggcctg        48

<210> SEQ ID NO 52
<211> LENGTH: 48
<212> TYPE: DNA
<213> ORGANISM: Mus musculus

<400> SEQUENCE: 52
catcctatcc ccaggaacag ctgtgtcatt taaaaatttc tgtgcagt        48

<210> SEQ ID NO 53
<211> LENGTH: 34
<212> TYPE: DNA
<213> ORGANISM: Mus musculus

<400> SEQUENCE: 53
aaacacaagc ctaaaaaaaa aaacaagcat gggg        34

<210> SEQ ID NO 54
<211> LENGTH: 1564
<212> TYPE: DNA
<213> ORGANISM: Homo sapiens

<400> SEQUENCE: 54
cggtcccctc ccccgctggc ggggcccgga cagaagatgg tgcagaagaa accagccgaa        60
cttcagggtt ccaccgttc gttcaagggg cagaacccct tcgagctggc cttctcccta       120
gaccagcccg accacggaga ctctgacttt ggcctgcagt gctcagcccg ccctgacatg       180

```
cccgccagcc agcccattga catcccggac gccaagaaga ggggcaagaa gaagaagcgc      240
ggccgggcca ccgacagctt ctcgggcagg tttgaagacg tctaccagct gcaggaagat      300
gtgctggggg agggcgctca tgcccgagtg cagacctgca tcaacctgat caccagccag      360
gagtacgccg tcaagatcat tgagaagcag ccaggccaca ttcggagcag ggttttcagg      420
gaggtggaga tgctgtacca gtgccaggga cacaggaacg tcctagagct gattgagttc      480
ttcgaggagg aggaccgctt ctacctggtg tttgagaaga tgcggggagg ctccatcctg      540
agccacatcc acaagcgccg gcacttcaac gagctggagg ccagcgtggt ggtgcaggac      600
gtggccagcg ccttggactt tctgcataac aaaggcatcg cccacaggga cctaaagccg      660
gaaaacatcc tctgtgagca ccccaaccag gtctcccccg tgaagatctg tgacttcgac      720
ctgggcagcg gcatcaaact caacggggac tgctccccta tctccacccc ggagctgctc      780
actccgtgcg gctcggcgga gtacatggcc ccggaggtag tggaggcctt cagcgaggag      840
gctagcatct acgacaagcg ctgcgacctg tggagcctgg gcgtcatctt gtatatccta      900
ctcagcggct acccgccctt cgtgggccgc tgtggcagcg actgcggctg ggaccgcggc      960
gaggcctgcc ctgcctgcca gaacatgctg tttgagagca tccaggaggg caagtacgag     1020
ttccccgaca aggactgggc ccacatctcc tgcgctgcca agacctcat ctccaagctg     1080 ctggtccgtg acgccaagca gaggctgagt gccgcccaag tcctgcagca cccctgggtt     1140
caggggtgcg ccccggagaa caccttgccc actcccatgg tcctgcagag gtgggacagt     1200
cacttcctcc tccctcccca ccctgtcgc atccacgtgc gacctggagg actggtcaga     1260
accgttactg tgaatgagtg aagatcctgg aggaccctgg gccccaggcc agctcccatc     1320 gctggggac ggtgaacggc catgtgttaa tgttacgatg tttttaaaag acaaaaaaaa     1380
aaaaaaaacc tcaaaagttt ttttaaagtg ggggaaaaac atccaagcac tttaattcca     1440
atgtaccagg tgaactgacg gagctcagaa gttttccttt acaccaactg tcaatgccgg     1500
aattttgtat tctgttttgt aaagatttaa taaaagtcaa aaaacttgca aaaaaaaaaa     1560
aaaa                                                                 1564
```

<210> SEQ ID NO 55
<211> LENGTH: 1778
<212> TYPE: DNA
<213> ORGANISM: Homo sapiens

<400> SEQUENCE: 55

```
cggctcctct cagcggcggt ggcccaggta gaggggtccg cgctggcggc ggcggcggcg       60
ctgttccccg cgcggtccgc ggagcggggt ccgggctgcg cgacgtgggg cggcggcggc      120
actgcggccc cggcccaagc ccgacccggg gtcccctcct cggccgcccc cgcccggcc      180 gcccgccctc gggcctcccc ccgggccctc ggtcccctcc ccgctggcg gggcccggac      240 agaagatggt gcagaagaaa ccagccgaac ttcagggttt ccaccgttcg ttcaaggggc      300
agaacccctt cgagctggcc ttctccctag accagcccga ccacggagac tctgactttg      360
gcctgcagtg ctcagcccgc cctgacatgc ccgccagcca gcccattgac atcccggacg      420
ccaagaagag gggcaagaag aagaagcgcg gccgggccac cgacagcttc tcgggcaggt      480
ttgaagacgt ctaccagctg caggaagatg tgctggggga gggcgctcat gcccgagtgc      540
agacctgcat caacctgatc accagccagg agtacgccgt caagatcatt gagaagcagc      600
caggccacat tcggagcagg gttttcaggg aggtggagat gctgtaccag tgccagggac      660
```

| | |
|---|---|
| acaggaacgt cctagagctg attgagttct tcgaggagga ggaccgcttc tacctggtgt | 720 |
| ttgagaagat gcggggaggc tccatcctga gccacatcca caagcgccgg cacttcaacg | 780 |
| agctggaggc cagcgtggtg gtgcaggacg tggccagcgc cttggacttt ctgcataaca | 840 |
| aaggcatcgc ccacagggac ctaaagccgg aaaacatcct ctgtgagcac cccaaccagg | 900 |
| tctcccccgt gaagatctgt gacttcgacc tgggcagcgg catcaaactc aacggggact | 960 |
| gctcccctat ctccacccg gagctgctca ctccgtgcgg ctcggcggag tacatggccc | 1020 |
| cggaggtagt ggaggccttc agcgaggagg ctagcatcta cgacaagcgc tgcgacctgt | 1080 |
| ggagcctggg cgtcatcttg tatatcctac tcagcggcta cccgcccttc gtgggccgct | 1140 |
| gtggcagcga ctgcggctgg gaccgcggcg aggcctgccc tgcctgccag aacatgctgt | 1200 |
| ttgagagcat ccaggagggc aagtacgagt tccccgacaa ggactgggcc cacatctcct | 1260 |
| gcgctgccaa agacctcatc tccaagctgc tggtccgtga cgccaagcag aggctgagtg | 1320 |
| ccgcccaagt cctgcagcac ccctgggttc aggggtgcgc cccggagaac accttgccca | 1380 |
| ctcccatggt cctgcagagg tgggacagtc acttcctcct ccctcccac ccctgtcgca | 1440 |
| tccacgtgcg acctggagga ctggtcagaa ccgttactgt gaatgagtga agatcctgga | 1500 |
| ggaccctggg ccccaggcca gctcccatcg ctggggacg tgaacggcc atgtgttaat | 1560 |
| gttacgatgt tttaaaaga caaaaaaaaa aaaaaaacct caaaagtttt tttaaagtgg | 1620 |
| gggaaaaaca tccaagcact ttaattccaa tgtaccaggt gaactgacgg agctcagaag | 1680 |
| ttttccttta caccaactgt caatgccgga attttgtatt ctgttttgta aagatttaat | 1740 |
| aaaagtcaaa aaacttgcaa aaaaaaaaaa aaaaaaaa | 1778 |

<210> SEQ ID NO 56
<211> LENGTH: 2617
<212> TYPE: DNA
<213> ORGANISM: Homo sapiens

<400> SEQUENCE: 56

| | |
|---|---|
| gcgatctgca ggtaggggtg cgcgcgaccg ctccccggcg ggagccagcg aaggtttcca | 60 |
| tgtcagaggc cgatggagaa ctgaagattg ccacctacgc acaaaggcca ttgagacact | 120 |
| tcgtgtagct ggaagacacc aacttcctga caggagcttt atttcatttg ggatttcaag | 180 |
| tttacagatg gtatcttctc aaaagttgga aaaacctata gagatgggca gtagcgaacc | 240 |
| ccttcccatc gcagatggtg acaggaggag gaagaagaag cggaggggcc gggccactga | 300 |
| ctccttgcca ggaaagtttg aagatatgta caagctgacc tctgaattgc ttggagaggg | 360 |
| agcctatgcc aaagttcaag gtgccgtgag cctacagaat ggcaaagagt atgccgtcaa | 420 |
| aatcatcgag aaacaagcag gcacagtcg gagtagggtg tttcgagagg tggagacgct | 480 |
| gtatcagtgt cagggaaaca gaacattttt ggagctgatt gagttctttg aagatgacac | 540 |
| aaggttttac ttggtctttg agaaattgca aggaggttcc atcttagccc acatccagaa | 600 |
| gcaaaagcac ttcaatgagc gagaagccag ccgagtggtg cgggacgttg ctgctgccct | 660 |
| tgacttcctg cataccaaag gcattgctca tcgtgatctg aaaccagaaa atatattgtg | 720 |
| tgaatctcca gaaaaggtgt ctccagtgaa atctgtgac tttgacttgg cagtgggat | 780 |
| gaaactgaac aactcctgta cccccataac cacaccagag ctgaccaccc catgtggctc | 840 |
| tgcagaatac atggcccctg aggtagtgga ggtcttcacg gaccaggcca cattctacga | 900 |
| caagcgctgt gacctgtgga gcctgggcgt ggtcctctac atcatgctga gtggctaccc | 960 |
| acccttcgtg ggtcactgcg gggccgactg tggctgggac cggggcgagg tctgcagggt | 1020 |

```
gtgccagaac aagctgtttg aaagcatcca ggaaggcaag tatgagtttc ctgacaagga   1080
ctgggcacac atctccagtg aagccaaaga cctcatctcc aagctcctgg tgcgagatgc   1140
aaagcagaga cttagcgccg cccaagttct gcagcaccca tgggtgcagg ggcaagctcc   1200
agaaaaggga ctccccacgc cgcaagtcct ccagaggaac agcagcacaa tggacctgac   1260
gctcttcgca gctgaggcca tcgcccttaa ccgccagcta tctcagcacg aagagaacga   1320
actagcagag gagccagagg cactagctga tggcctctgc tccatgaagc tttcccctcc   1380
ctgcaagtca cgcctggccc ggagacgggc cctggcccag gcaggccgtg gtgaagacag   1440
gagcccgccc acagcactct gaaatgctcc agtcacacct ataggccct aggcctggcc    1500 aggcattgtc ccctggaaac ctgtgtggct aaagtctgct gagcaggcag cagcctctgc   1560
tctgtggctc cattcaggct ttttcatcta cgaaggccct gaggttccca tcaaccccca   1620
tttccctagg gtcctggagg aaaaagcttt ttccaaaggg gttgtctttg aaaaggaaag   1680
caatcacttc tcactttgca taattgcctg cagcaggaac atctcttcac tgggctccac   1740
ctgctcaccc gcctgcagat ctgggatcca gcctgctctc accgctgtag ctgtggcggc   1800
tggggctgca gcctgcaggg agaagcaaga agcatcagtt gacagaggct gccgacacgt   1860
gcctcttccc tctcttctct gtcaccctcc tctggcggtc cttccacctt cctctgtcct   1920
ccggatgtcc tctttgcccg tcttctccct tggctgagca aagccatccc ctcaattcag   1980
ggaagggcaa ggagccttcc tcattcagga aatcaaatca gtcttccggt ctgcagcacg   2040
gaaaagcaca taatctttct tgctgtgac tgaaatgtat  ccctcgttta tcatcccctt    2100
tgtttgtgat tgctgctaaa gtcagtagta tcgtttttt aaaaaaaaag tttggtgttt     2160
ttaaccatct gttccagcaa agatgatacc ttaaactccc actgcaagcc catgaacttc   2220
ccagagagtg aacggcttg ctcttctttc tagaatgtcc atgcacttgg gttttaatca     2280
gcagttccct attattctga tttttaagctg ttcctgtgat gaacttagag acagcatcgg   2340
tgtctgctgc tgtgtcccca ggtcttgtgt gggtggcaca gatctgggca gttagatagt   2400
gctctgtgcc taaggtgaag ccacactagg gtgaagcctc acttccctgt ttgagcaatg   2460
cagtgcctgc tgcccgtgtg catgaaggta cagccattca tataagtgga actattgagt   2520
tacataaaga aaatagattt gcatttgtca ggcagacgtt tatacaacac cacggtgctt   2580
ttatacattg tgcttatttt aataaaactg aaattct                             2617
```

<210> SEQ ID NO 57
<211> LENGTH: 3080
<212> TYPE: DNA
<213> ORGANISM: Mus musculus

<400> SEQUENCE: 57

```
gcccagcaca gggactctga cttcagccca cagtgtgaag cccgacctga catgccttcc     60
agccagccca ttgacatccc agatgccaag aagagaggcc ggaaaaagaa cgctgtcgg    120 gctactgaca gcttctcagg caggttcgaa gatgtctatc agctgcagga ggatgtgctg   180
ggggaaggtg ctcacgctcg tgtgcagacc tgtgtcaatc tcatcaccaa ccaggaatat   240
gctgtcaaga tcattgagaa gcagctgggc cacatccgca gcagggtgtt ccgggaggtg   300
gagatgctgt accagtgcca gggacatagg aatgttctag aactgattga gttctttgag   360
gaggaggacc gtttctacct ggtgtttgag aagatgcgtg gcggatccat cctaagccac   420
atccatagaa ggcgccactt taacgagctg gaggccagcg tggtagtaca ggacgtggcc   480
```

```
agtgccctgg acttcctgca taacaaaggc atcgcccaca gggacctaaa gccagagaac    540
atcctatgtg agcaccccaa ccaggtctcg ccagtgaaga tctgcgactt cgaccttggc    600
agtggtatca aactcaatgg agactgctcc cccatctcca caccagagct gctcaccccg    660
tgtgggtcag ctgagtacat ggccccagag gtggtgagg  ccttcagtga agaggccagc    720
atctacgaca agcgctgcga cctgtggagc ctgggcgtca tcctctacat cctgcttagt    780
ggctacccgc ccttcgtggg ccactgtggc agcgactgtg gctgggaccg tggggaggcc    840
tgtcctgcct gccagaacat gctgtttgag agcatccagg agggcaagta tgagttccct    900
gacaaggact ggtcccacat ctcctttgct gccaaagacc tcatctccaa gctgctggtc    960
cgagatgcca agcagaggct gagtgctgcc caagtcctgc agcatccctg ggtgcagggg   1020
tgtgccccag agaacaccct accgacaccc ttggttctgc agaggaacag ctgtgccaaa   1080
gacctcacgt cctttgcggc tgaggccatc gccatgaacc ggcagctggc ccagtgtgag   1140
gaggacgctg gcaggaccca gcctgtggtc atccgagcta cctcacgctg cctgcagctg   1200
tccccaccct cccagtccaa gctggcccag cggcgccaga gggctagcct gtcggccacc   1260
cctgtggtcc ttgtggggga tcgcgcatga ccccccactag ctccttgtac atatgcccct   1320
gccccgcggg gcctgaaggc tagggacctg acacccccac cccttgccat tccaggtgcc   1380
agctcagctg ggtcctctgg gggtgtaggg gtctgttagg gggtgtctcc ttttctccct   1440
gtccttcccc tgccctgccc acttggcttt gttttgtttg tttttctttg ccgctattga   1500
aagcaagtgc ccggaggagg gcggagggct caggccgccc agcctgcacc ccacgatgct   1560
cacctgccaa ctgtgaaggt cctgccacct gcgcccccac ctccactcca gccactctgc   1620
tgtcttccag ggttggggat cccgcagggt cagcacccca cacctctccc agccctcagt   1680
gttgtcaggg acaggccctc ctggtgagca cagtggtggt tgcatctcct caccagagca   1740
cccttgggtc tggggtaggg cagggctccc tgtcttggat agagacctct ggggagcagg   1800
tggatgggga cagtgcactt gattgacccc gagtccccat catccacctg cagtgtccct   1860
tggagggttg acaatcagaa acccctccca ggctgcttag ctccttgccc tgggacagac   1920
ctactgctcc caaccccact tcccaggggc agagctggaa ggggaccctg cacccagcta   1980
gctccaccac agcaggagag gtgctggacc aggctttcat cagcaaacat ggggctccca   2040
catgtctccc cacccagggc acctgagtgc cccttctcag ggctcagcct gaccacggcc   2100
acgtcctgcc cctggggttc ctaagctctc ctagctgctt ctgttagcca gagctgaggc   2160
catacccagg gctctcacct tcctgttgcc cccagagggc agcagctcag gcgtgcctgc   2220
tttcaggaaa gggaggctgg gaagggatgt ggtggccctg cggtgcccag acctaactgc   2280
ccgaggcctg tagactgttc tagccgaact actatgcaat acaagttccc attttctcca   2340
tggccctgct ggtcggggc  ggctgccagg ggccaggcca ccctgccctg caactgctca   2400
ggtgtctaca gggcagcccc tggcctcaaa aatccttggt caggattgtt tgtcgagttt   2460
agtttaggct ttttttttt  ttttaaagaa ataatttgac ttgcttccct gttcttgaag   2520
agtacttgaa tgtcggggtc tggtgggtgg gggcctggga cacccactgc ccagcatcct   2580
ccaccctcct ccctagtctc ataggatcgt cacagtggag gtgacatgcc ttctccagtc   2640
ctgccccacc tgcctctgtg gacacatttc caaagaaccc ctgggggtgg gacctcctcc   2700
atcagtatga ctcagctgtt ggccacctga ggactcggcc ccctgcagg  ttcctgaagc   2760 aacctgactg ggcagtgagc agcattgacc cccactcacc cccaaaacag ggctgtgatt   2820
tccttagtcc ttccaagccc gacctggagg atgggtcaga ccccttaact gtgaatgaga   2880
```

```
catgatcctg ggctggcttc gccacaaacc atgcagaaat ctaaaaggcc tgttgtagag    2940 tggggacat  gcaagcactt ttaactccat cgtaccaggt gaactgacct ccggactcct    3000
ttcccaccaa ctgtcaacgc caggattttg tattctgttt tgtaaggatt taataaaagt    3060
catttaaaaa aaaaaaaaaa                                                3080
```

<210> SEQ ID NO 58
<211> LENGTH: 414
<212> TYPE: PRT
<213> ORGANISM: Homo sapiens

<400> SEQUENCE: 58

Met Val Gln Lys Lys Pro Ala Glu Leu Gln Gly Phe His Arg Ser Phe
1               5                   10                  15

Lys Gly Gln Asn Pro Phe Glu Leu Ala Phe Ser Leu Asp Gln Pro Asp
                20                  25                  30

His Gly Asp Ser Asp Phe Gly Leu Gln Cys Ser Ala Arg Pro Asp Met
            35                  40                  45

Pro Ala Ser Gln Pro Ile Asp Ile Pro Asp Ala Lys Lys Arg Gly Lys
        50                  55                  60

Lys Lys Lys Arg Gly Arg Ala Thr Asp Ser Phe Ser Gly Arg Phe Glu
65                  70                  75                  80

Asp Val Tyr Gln Leu Gln Glu Asp Val Leu Gly Glu Gly Ala His Ala
                85                  90                  95

Arg Val Gln Thr Cys Ile Asn Leu Ile Thr Ser Gln Glu Tyr Ala Val
            100                 105                 110

Lys Ile Ile Glu Lys Gln Pro Gly His Ile Arg Ser Arg Val Phe Arg
        115                 120                 125

Glu Val Glu Met Leu Tyr Gln Cys Gln Gly His Arg Asn Val Leu Glu
    130                 135                 140

Leu Ile Glu Phe Phe Glu Glu Asp Arg Phe Tyr Leu Val Phe Glu
145                 150                 155                 160

Lys Met Arg Gly Gly Ser Ile Leu Ser His Ile His Lys Arg Arg His
                165                 170                 175

Phe Asn Glu Leu Glu Ala Ser Val Val Val Gln Asp Val Ala Ser Ala
            180                 185                 190

Leu Asp Phe Leu His Asn Lys Gly Ile Ala His Arg Asp Leu Lys Pro
        195                 200                 205

Glu Asn Ile Leu Cys Glu His Pro Asn Gln Val Ser Pro Val Lys Ile
    210                 215                 220

Cys Asp Phe Asp Leu Gly Ser Gly Ile Lys Leu Asn Gly Asp Cys Ser
225                 230                 235                 240

Pro Ile Ser Thr Pro Glu Leu Leu Thr Pro Cys Gly Ser Ala Glu Tyr
                245                 250                 255

Met Ala Pro Glu Leu Val Glu Ala Phe Ser Glu Glu Ala Ser Ile Tyr
            260                 265                 270

Asp Lys Arg Cys Asp Leu Trp Ser Leu Gly Val Ile Leu Tyr Ile Leu
        275                 280                 285

Leu Ser Gly Tyr Pro Pro Phe Val Gly Arg Cys Gly Ser Asp Cys Gly
    290                 295                 300

Trp Asp Arg Gly Glu Ala Cys Pro Ala Cys Gln Asn Met Leu Phe Glu
305                 310                 315                 320

Ser Ile Gln Glu Gly Lys Tyr Glu Phe Pro Asp Lys Asp Trp Ala His
                325                 330                 335

```
Ile Ser Cys Ala Ala Lys Asp Leu Ile Ser Lys Leu Leu Val Arg Asp
                340                 345                 350

Ala Lys Gln Arg Leu Ser Ala Gln Val Leu Gln His Pro Trp Val
            355                 360                 365

Gln Gly Cys Ala Pro Glu Asn Thr Leu Pro Thr Pro Met Val Leu Gln
        370                 375                 380

Arg Trp Asp Ser His Phe Leu Leu Pro Pro His Pro Cys Arg Ile His
385                 390                 395                 400

Val Arg Pro Gly Gly Leu Val Arg Thr Val Thr Val Asn Glu
                405                 410
```

<210> SEQ ID NO 59
<211> LENGTH: 465
<212> TYPE: PRT
<213> ORGANISM: Homosapiens

<400> SEQUENCE: 59

```
Met Val Ser Ser Gln Lys Leu Glu Lys Pro Ile Glu Met Gly Ser Ser
1               5                   10                  15

Glu Pro Leu Pro Ile Ala Asp Gly Asp Arg Arg Arg Lys Lys Lys Arg
            20                  25                  30

Arg Gly Arg Ala Thr Asp Ser Leu Pro Gly Lys Phe Glu Asp Met Tyr
        35                  40                  45

Lys Leu Thr Ser Glu Leu Leu Gly Glu Gly Ala Tyr Ala Lys Val Gln
    50                  55                  60

Gly Ala Val Ser Leu Gln Asn Gly Lys Glu Tyr Ala Val Lys Ile Ile
65                  70                  75                  80

Glu Lys Gln Ala Gly His Ser Arg Ser Arg Val Phe Arg Glu Val Glu
                85                  90                  95

Thr Leu Tyr Gln Cys Gln Gly Asn Lys Asn Ile Leu Glu Leu Ile Glu
            100                 105                 110

Phe Phe Glu Asp Asp Thr Arg Phe Tyr Leu Val Phe Glu Lys Leu Gln
        115                 120                 125

Gly Gly Ser Ile Leu Ala His Ile Gln Lys Gln Lys His Phe Asn Glu
    130                 135                 140

Arg Glu Ala Ser Arg Val Val Arg Asp Val Ala Ala Ala Leu Asp Phe
145                 150                 155                 160

Leu His Thr Lys Asp Lys Val Ser Leu Cys His Leu Gly Trp Ser Ala
                165                 170                 175

Met Ala Pro Ser Gly Leu Thr Ala Ala Pro Thr Ser Leu Gly Ser Ser
            180                 185                 190

Asp Pro Pro Thr Ser Ala Ser Gln Val Ala Gly Thr Thr Gly Ile Ala
        195                 200                 205

His Arg Asp Leu Lys Pro Glu Asn Ile Leu Cys Glu Ser Pro Glu Lys
    210                 215                 220

Val Ser Pro Val Lys Ile Cys Asp Phe Asp Leu Gly Ser Gly Met Lys
225                 230                 235                 240

Leu Asn Asn Ser Cys Thr Pro Ile Thr Thr Pro Glu Leu Thr Thr Pro
                245                 250                 255

Cys Gly Ser Ala Glu Tyr Met Ala Pro Glu Val Val Glu Val Phe Thr
            260                 265                 270

Asp Gln Ala Thr Phe Tyr Asp Lys Arg Cys Asp Leu Trp Ser Leu Gly
        275                 280                 285

Val Val Leu Tyr Ile Met Leu Ser Gly Tyr Pro Pro Phe Val Gly His
```

290                 295                 300
Cys Gly Ala Asp Cys Gly Trp Asp Arg Gly Glu Val Cys Arg Val Cys
305                 310                 315                 320

Gln Asn Lys Leu Phe Glu Ser Ile Gln Glu Gly Lys Tyr Glu Phe Pro
                325                 330                 335

Asp Lys Asp Trp Ala His Ile Ser Ser Glu Ala Lys Asp Leu Ile Ser
                340                 345                 350

Lys Leu Leu Val Arg Asp Ala Lys Gln Arg Leu Ser Ala Ala Gln Val
                355                 360                 365

Leu Gln His Pro Trp Val Gln Gly Ala Pro Glu Lys Gly Leu Pro
370                 375                 380

Thr Pro Gln Val Leu Gln Arg Asn Ser Ser Thr Met Asp Leu Thr Leu
385                 390                 395                 400

Phe Ala Ala Glu Ala Ile Ala Leu Asn Arg Gln Leu Ser Gln His Glu
                405                 410                 415

Glu Asn Glu Leu Ala Glu Glu Pro Glu Ala Leu Ala Asp Gly Leu Cys
                420                 425                 430

Ser Met Lys Leu Ser Pro Pro Cys Lys Ser Arg Leu Ala Arg Arg Arg
                435                 440                 445

Ala Leu Ala Gln Ala Gly Arg Gly Glu Asp Arg Ser Pro Pro Thr Ala
                450                 455                 460

Leu
465

<210> SEQ ID NO 60
<211> LENGTH: 24
<212> TYPE: DNA
<213> ORGANISM: Artificial sequence
<220> FEATURE:
<223> OTHER INFORMATION: Intron-exon junction

<400> SEQUENCE: 60
ccttagacct cggcccagca cagg                                              24

<210> SEQ ID NO 61
<211> LENGTH: 24
<212> TYPE: DNA
<213> ORGANISM: Artificial sequence
<220> FEATURE:
<223> OTHER INFORMATION: Exon-Intron junction

<400> SEQUENCE: 61
gaagcccgac ctggtgagcc ccca                                              24

<210> SEQ ID NO 62
<211> LENGTH: 24
<212> TYPE: DNA
<213> ORGANISM: Artificial sequence
<220> FEATURE:
<223> OTHER INFORMATION: Intron-exon junction

<400> SEQUENCE: 62
ctcttctcta cagacatgcc ttcc                                              24

<210> SEQ ID NO 63
<211> LENGTH: 24
<212> TYPE: DNA
<213> ORGANISM: Artificial sequence
<220> FEATURE:
<223> OTHER INFORMATION: Exon-Intron junction

```
<400> SEQUENCE: 63
gcaggttcga aggtgagctg caga                                           24

<210> SEQ ID NO 64
<211> LENGTH: 24
<212> TYPE: DNA
<213> ORGANISM: Artificial sequence
<220> FEATURE:
<223> OTHER INFORMATION: Intron-exon junction

<400> SEQUENCE: 64
ctcgcattcc agatgtctat cagc                                           24

<210> SEQ ID NO 65
<211> LENGTH: 24
<212> TYPE: DNA
<213> ORGANISM: Artificial sequence
<220> FEATURE:
<223> OTHER INFORMATION: Exon-Intron junction

<400> SEQUENCE: 65
tatgctgtca agagctgggg tctg                                           24

<210> SEQ ID NO 66
<211> LENGTH: 24
<212> TYPE: DNA
<213> ORGANISM: Artificial sequence
<220> FEATURE:
<223> OTHER INFORMATION: Intron-exon junction

<400> SEQUENCE: 66
cctacattgt agatcattga gaag                                           24

<210> SEQ ID NO 67
<211> LENGTH: 24
<212> TYPE: DNA
<213> ORGANISM: Artificial sequence
<220> FEATURE:
<223> OTHER INFORMATION: Exon-Intron junction

<400> SEQUENCE: 67
cagggacata ggtaaggtgg cctg                                           24

<210> SEQ ID NO 68
<211> LENGTH: 24
<212> TYPE: DNA
<213> ORGANISM: Artificial sequence
<220> FEATURE:
<223> OTHER INFORMATION: Intron-exon junction

<400> SEQUENCE: 68
tcccaactca ggaatgttct agaa                                           24

<210> SEQ ID NO 69
<211> LENGTH: 29
<212> TYPE: DNA
<213> ORGANISM: Artificial sequence
<220> FEATURE:
<223> OTHER INFORMATION: Exon-Intron junction

<400> SEQUENCE: 69
gaagatgcgt ggcggtaggt aggtactgg                                      29

<210> SEQ ID NO 70
<211> LENGTH: 24
```

```
<212> TYPE: DNA
<213> ORGANISM: Artificial sequence
<220> FEATURE:
<223> OTHER INFORMATION: Intron-exon junction

<400> SEQUENCE: 70
ctggcctgca caggatccat ccta                                        24

<210> SEQ ID NO 71
<211> LENGTH: 24
<212> TYPE: DNA
<213> ORGANISM: Artificial sequence
<220> FEATURE:
<223> OTHER INFORMATION: Exon-Intron junction

<400> SEQUENCE: 71
gcataacaaa ggtgtggcag ggac                                        24

<210> SEQ ID NO 72
<211> LENGTH: 24
<212> TYPE: DNA
<213> ORGANISM: Artificial sequence
<220> FEATURE:
<223> OTHER INFORMATION: Intron-exon junction

<400> SEQUENCE: 72
cacctcacta ggcatcgccc acag                                        24

<210> SEQ ID NO 73
<211> LENGTH: 24
<212> TYPE: DNA
<213> ORGANISM: Artificial sequence
<220> FEATURE:
<223> OTHER INFORMATION: Exon-Intron junction

<400> SEQUENCE: 73
ccccaaccag gtgaggctgc ctga                                        24

<210> SEQ ID NO 74
<211> LENGTH: 24
<212> TYPE: DNA
<213> ORGANISM: Artificial sequence
<220> FEATURE:
<223> OTHER INFORMATION: Intron-exon junction

<400> SEQUENCE: 74
ccattcccag gtctcgccag tgaa                                        24

<210> SEQ ID NO 75
<211> LENGTH: 24
<212> TYPE: DNA
<213> ORGANISM: Artificial sequence
<220> FEATURE:
<223> OTHER INFORMATION: Exon-Intron junction

<400> SEQUENCE: 75
gctgctcacc ccggtgaggg cagt                                        24

<210> SEQ ID NO 76
<211> LENGTH: 24
<212> TYPE: DNA
<213> ORGANISM: Artificial sequence
<220> FEATURE:
<223> OTHER INFORMATION: Intron-exon junction

<400> SEQUENCE: 76
```
ccctgcccca cagtgtgggt cagc                                              24

<210> SEQ ID NO 77
<211> LENGTH: 24
<212> TYPE: DNA
<213> ORGANISM: Artificial sequence
<220> FEATURE:
<223> OTHER INFORMATION: Exon-Intron junction

<400> SEQUENCE: 77
tgggtgcagg gggtaagcct tggg                                              24

<210> SEQ ID NO 78
<211> LENGTH: 24
<212> TYPE: DNA
<213> ORGANISM: Artificial sequence
<220> FEATURE:
<223> OTHER INFORMATION: Intron-exon junction

<400> SEQUENCE: 78
gacttcttac agtgtgcccc agag                                              24

<210> SEQ ID NO 79
<211> LENGTH: 24
<212> TYPE: DNA
<213> ORGANISM: Artificial sequence
<220> FEATURE:
<223> OTHER INFORMATION: Exon-Intron junction

<400> SEQUENCE: 79
ttggttctgc agaggtgagg cctg                                              24

<210> SEQ ID NO 80
<211> LENGTH: 24
<212> TYPE: DNA
<213> ORGANISM: Artificial sequence
<220> FEATURE:
<223> OTHER INFORMATION: Intron-exon junction

<400> SEQUENCE: 80
catcctatcc ccaggaacag ctgt                                              24

<210> SEQ ID NO 81
<211> LENGTH: 22
<212> TYPE: DNA
<213> ORGANISM: Artificial sequence
<220> FEATURE:
<223> OTHER INFORMATION: Exon-Intron junction

<400> SEQUENCE: 81
gtcatttaaa aatttctgtgca gt                                              22

<210> SEQ ID NO 82
<211> LENGTH: 34
<212> TYPE: DNA
<213> ORGANISM: Artificial sequence
<220> FEATURE:
<223> OTHER INFORMATION: Additional sequence

<400> SEQUENCE: 82
aaacacaagc ctaaaaaaaa aaacaagcat gggg                                   34

<210> SEQ ID NO 83
<211> LENGTH: 2745
<212> TYPE: DNA
<213> ORGANISM: Homo sapiens

<400> SEQUENCE: 83

```
ggcacgaggg cgaccgctcc ccggcgggag ccagcgaagg tttccatgtc agaggccgat      60
ggagaactga agattgccac ctacgcacaa aggccattga cacttcgt gtagctggaa       120
gacaccaact tcctgacagg agctttattt catttgggat ttcaagttta cagatggtat    180
cttctcaaaa gttggaaaaa cctatagaga tgggcagtag cgaacccctt cccatcgcag    240
atggtgacag gaggaggaag aagaagcgga ggggccgggc cactgactcc ttgccaggaa    300
agtttgaaga tatgtacaag ctgacctctg aattgcttgg agagggagcc tatgccaaag    360
ttcaaggtgc cgtgagccta cagaatggca agagtatgc cgtcaaaatc atcgagaaac     420
aagcagggca cagtcggagt agggtgtttc gagaggtgga gacgctgtat cagtgtcagg    480
gaaacaagaa cattttggag ctgattgagt tctttgaaga tgacacaagg ttttacttgg    540
tctttgagaa attgcaagga ggttccatct tagcccacat ccagaagcaa aagcacttca    600
atgagcgaga agccagccga gtggtgcggg acgttgctgc tgcccttgac ttcctgcata    660
ccaaagacaa agtctctctc tgtcacctag gctggagtgc tatggcgcca tcagggctca    720
ctgcagcccc aacctcctg gctccagtg atcctccac ctcagcctcc caagtagctg       780
ggactacagg cattgctcat cgtgatctga aaccagaaaa tatattgtgt gaatctccag    840
aaaaggtgtc tccagtgaaa atctgtgact ttgacttggg cagtgggatg aaactgaaca    900
actcctgtac ccccataacc acaccagagc tgaccacccc atgtggctct gcagaataca    960
tggcccctga ggtagtggag gtcttcacgg accaggccac attctacgac aagcgctgtg   1020
acctgtggag cctgggcgtg gtcctctaca tcatgctgag tggctaccca cccttcgtgg   1080
gtcactgcgg ggccgactgt ggctgggacc ggggcgaggt ctgcagggtg tgccagaaca   1140
agctgtttga aagcatccag gaaggcaagt atgagtttcc tgacaaggac tgggcacaca   1200
tctccagtga agccaaagac ctcatctcca agctcctggt gcgagatgca aagcagagac   1260
ttagcgccgc ccaagttctg cagcacccat gggtgcaggg gcaagctcca gaaaagggac   1320
tccccacgcc gcaagtcctc cagaggaaca gcagcacaat ggacctgacg ctcttcgcag   1380
ctgaggccat cgcccttaac cgccagctat ctcagcacga agagaacgaa ctagcagagg   1440
agccagaggc actagctgat ggcctctgct ccatgaagct ttcccctccc tgcaagtcac   1500
gcctggcccg gagacgggcc ctggcccagg caggccgtgg tgaagacagg agcccgccca   1560
cagcactctg aaatgctcca gtcacacctt ataggcccta ggcctggcca ggcattgtcc   1620
cctggaaacc tgtgtggcta agtctgctg agcaggcagc agcctctgct ctgtggctcc    1680
attcaggctt tttcatctac gaaggccctg aggttcccat caaccccat ttccctaggg    1740
tcctggagga aaaagctttt tccaaagggg ttgtctttga aaaggaaagc aatcacttct   1800
cactttgcat aattgcctgc agcaggaaca tctcttcact gggctccacc tgctcacccg   1860
cctgcagatc tgggatccag cctgctctca ccgctgtagc tgtggcggct ggggctgcag   1920
cctgcaggga gaagcaagaa gcatcagttg acagaggctg ccgacacgtg cctcttccct   1980
ctcttctctg tcaccctcct ctggcggtcc ttccaccttc ctctgtcctc cggatgtcct   2040
ctttgcccgt cttctccctt ggctgagcaa agccatcccc tcaattcagg gaagggcaag   2100
gagccttcct cattcaggaa atcaaatcag tcttccggtc tgcagcacgg aaaagcacat   2160
aatctttctt tgctgtgact gaatgtatc cctcgtttat catccccttt gtttgtgatt    2220
gctgctaaag tcagtagtat cgttttttta aaaaaaagt ttggtgtttt taaccatgct    2280
```

-continued

```
gttccagcaa agatgatacc ttaaactccc actgcaagcc catgaacttc ccagagagtg   2340
gaacggcttg ctcttctttc tagaatgtcc atgcacttgg gttttaatca gcagttccct   2400
attattctga ttttaagctg ttcctgtgat gaacttagag acagcatcgg tgtctgctgc   2460
tgtgtcccca ggtcttgtgt gggtggcaca gatctgggca gttagatagt gctctgtgcc   2520
taaggtgaag ccacactagg gtgaagcctc acttccctgt ttgagcaatg cagtgcctgc   2580
tgcccgtgtg catgaaggta cagccattca gataagtgga actattgagt tacataaaga   2640
aaatagattt gcatttgtca ggcagacgtt tatacaacac cacggtgctt ttatacattg   2700
tgcttatttt aataaaactg aaattctaaa aaaaaaaaaa aaaaa            2745
```

```
<210> SEQ ID NO 84
<211> LENGTH: 360
<212> TYPE: PRT
<213> ORGANISM: Homo sapiens

<400> SEQUENCE: 84
```

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
    210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val

```
            290                 295                 300
Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
            355                 360

<210> SEQ ID NO 85
<211> LENGTH: 412
<212> TYPE: PRT
<213> ORGANISM: Mus musculus

<400> SEQUENCE: 85

Met Pro Ser Ser Gln Pro Ile Asp Ile Pro Asp Ala Lys Lys Arg Gly
1               5                   10                  15

Arg Lys Lys Lys Arg Cys Arg Ala Thr Asp Ser Phe Ser Gly Arg Phe
                20                  25                  30

Glu Asp Val Tyr Gln Leu Gln Glu Asp Val Leu Gly Glu Gly Ala His
            35                  40                  45

Ala Arg Val Gln Thr Cys Val Asn Leu Ile Thr Asn Gln Glu Tyr Ala
        50                  55                  60

Val Lys Ile Ile Glu Lys Gln Leu Gly His Ile Arg Ser Arg Val Phe
65                  70                  75                  80

Arg Glu Val Glu Met Leu Tyr Gln Cys Gln Gly His Arg Asn Val Leu
                85                  90                  95

Glu Leu Ile Glu Phe Phe Glu Glu Asp Arg Phe Tyr Leu Val Phe
            100                 105                 110

Glu Lys Met Arg Gly Gly Ser Ile Leu Ser His Ile His Arg Arg Arg
        115                 120                 125

His Phe Asn Glu Leu Glu Ala Ser Val Val Val Gln Asp Val Ala Ser
130                 135                 140

Ala Leu Asp Phe Leu His Asn Lys Gly Ile Ala His Arg Asp Leu Lys
145                 150                 155                 160

Pro Glu Asn Ile Leu Cys Glu His Pro Asn Gln Val Ser Pro Val Lys
                165                 170                 175

Ile Cys Asp Phe Asp Leu Gly Ser Gly Ile Lys Leu Asn Gly Asp Cys
            180                 185                 190

Ser Pro Ile Ser Thr Pro Glu Leu Leu Thr Pro Cys Gly Ser Ala Glu
        195                 200                 205

Tyr Met Ala Pro Glu Val Val Glu Ala Phe Ser Glu Glu Ala Ser Ile
210                 215                 220

Tyr Asp Lys Arg Cys Asp Leu Trp Ser Leu Gly Val Ile Leu Tyr Ile
225                 230                 235                 240

Leu Leu Ser Gly Tyr Pro Pro Phe Val Gly His Cys Gly Ser Asp Cys
                245                 250                 255

Gly Trp Asp Arg Gly Glu Ala Cys Pro Ala Cys Gln Asn Met Leu Phe
            260                 265                 270

Glu Ser Ile Gln Glu Gly Lys Tyr Glu Phe Pro Asp Lys Asp Trp Ser
        275                 280                 285

His Ile Ser Phe Ala Ala Lys Asp Leu Ile Ser Lys Leu Leu Val Arg
290                 295                 300
```

```
Asp Ala Lys Gln Arg Leu Ser Ala Ala Gln Val Leu Gln His Pro Trp
305                 310                 315                 320

Val Gln Gly Cys Ala Pro Glu Asn Thr Leu Pro Thr Pro Leu Val Leu
            325                 330                 335

Gln Arg Asn Ser Cys Ala Lys Asp Leu Thr Ser Phe Ala Ala Glu Ala
        340                 345                 350

Ile Ala Met Asn Arg Gln Leu Ala Gln Cys Glu Glu Asp Ala Gly Gln
            355                 360                 365

Asp Gln Pro Val Val Ile Arg Ala Thr Ser Arg Cys Leu Gln Leu Ser
370                 375                 380

Pro Pro Ser Gln Ser Lys Leu Ala Gln Arg Gln Arg Ala Ser Leu
385                 390                 395                 400

Ser Ala Thr Pro Val Val Leu Val Gly Asp Arg Ala
            405                 410

<210> SEQ ID NO 86
<211> LENGTH: 415
<212> TYPE: PRT
<213> ORGANISM: Mus musculus

<400> SEQUENCE: 86

Met Gly Ser Ser Glu Pro Leu Pro Ile Val Asp Ser Asp Lys Arg Arg
1               5                   10                  15

Lys Lys Lys Arg Lys Thr Arg Ala Thr Asp Ser Leu Pro Gly Lys Phe
            20                  25                  30

Glu Asp Val Tyr Gln Leu Thr Ser Glu Leu Leu Gly Glu Gly Ala Tyr
        35                  40                  45

Ala Lys Val Gln Gly Ala Val Asn Leu Gln Ser Gly Lys Glu Tyr Ala
    50                  55                  60

Val Lys Ile Ile Glu Lys Gln Ala Gly His Ser Arg Ser Arg Val Phe
65                  70                  75                  80

Arg Glu Val Glu Thr Leu Tyr Gln Cys Gln Gly Asn Arg Asn Ile Leu
                85                  90                  95

Glu Leu Ile Glu Phe Phe Glu Asp Asp Thr Arg Phe Tyr Leu Val Phe
            100                 105                 110

Glu Lys Leu Gln Gly Gly Ser Ile Leu Ala His Ile Gln Lys Arg Lys
        115                 120                 125

His Phe Asn Glu Arg Glu Ala Ser Arg Val Val Arg Asp Val Ala Thr
    130                 135                 140

Ala Leu Asp Phe Leu His Thr Lys Gly Ile Ala His Arg Asp Leu Lys
145                 150                 155                 160

Pro Glu Asn Ile Leu Cys Glu Ser Pro Glu Lys Val Ser Pro Val Lys
                165                 170                 175

Ile Cys Asp Phe Asp Leu Gly Ser Gly Val Lys Leu Asn Asn Ser Cys
            180                 185                 190

Thr Pro Ile Thr Thr Pro Glu Leu Thr Thr Pro Cys Gly Ser Ala Glu
        195                 200                 205

Tyr Met Ala Pro Glu Val Val Glu Val Phe Arg Asp Glu Ala Thr Phe
    210                 215                 220

Tyr Asp Lys Arg Cys Asp Leu Trp Ser Leu Gly Val Val Leu Tyr Ile
225                 230                 235                 240

Met Leu Ser Gly Tyr Pro Pro Phe Val Gly His Cys Gly Ala Asp Cys
                245                 250                 255

Gly Trp Asp Arg Gly Glu Val Cys Arg Met Cys Gln Asn Lys Leu Phe
            260                 265                 270
```

```
Glu Ser Ile Gln Glu Gly Lys Tyr Glu Phe Pro Asp Lys Asp Trp Ala
        275                 280                 285

His Ile Ser Asn Glu Ala Lys Asp Leu Ile Ser Lys Leu Leu Val Arg
        290                 295                 300

Asp Ala Lys Gln Arg Leu Ser Ala Ala Gln Val Leu Gln His Pro Trp
305                 310                 315                 320

Val Gln Gly Gln Ala Pro Glu Arg Gly Leu Pro Thr Pro Gln Val Leu
                325                 330                 335

Gln Arg Asn Ser Ser Thr Met Asp Leu Thr Leu Phe Ala Ala Glu Ala
                340                 345                 350

Ile Ala Leu Asn Arg Gln Leu Ser Gln His Glu Glu Asn Glu Leu Ala
        355                 360                 365

Glu Glu Gln Glu Ala Leu Ala Glu Gly Leu Cys Ser Met Lys Leu Ser
        370                 375                 380

Pro Pro Ser Lys Ser Arg Leu Ala Arg Arg Ala Leu Ala Gln Ala
385                 390                 395                 400

Gly Arg Ser Arg Asp Ala Asn Pro Cys Leu Thr Pro Ala Gly Leu
                405                 410                 415
```

<210> SEQ ID NO 87
<211> LENGTH: 2827
<212> TYPE: DNA
<213> ORGANISM: Homo sapiens

<400> SEQUENCE: 87

| | | | | |
|---|---|---|---|---|
| tctctgatcg ggcccacccc ctggatctag caccgcctct tccgcgttct cggaggagcg | | | | 60 |
| atctgcaggt aggggtgcgc gcgaccgctc cccggcggga gccagcgaag gtttccatgt | | | | 120 |
| cagaggccga tggagaactg aagattgcca cctacgcaca aaggccattg agacacttcg | | | | 180 |
| tgtagctgga agacaccaac ttcctgacag gagctttatt tcatttggga tttcaagttt | | | | 240 |
| acagatggta tcttctcaaa agttggaaaa acctatagag atgggcagta gcgaacccct | | | | 300 |
| tcccatcgca gatggtgaca ggaggaggaa gaagaagcgg aggggccggg ccactgactc | | | | 360 |
| cttgccagga aagtttgaag atatgtacaa gctgacctct gaattgcttg agagggagc | | | | 420 |
| ctatgccaaa gttcaaggtg ccgtgagcct acagaatggc aaagagtatg ccgtcaaaat | | | | 480 |
| catcgagaaa caagcagggc acagtcggag tagggtgttt cgagaggtgg agacgctgta | | | | 540 |
| tcagtgtcag ggaaacaaga acattttgga gctgattgag ttctttgaag atgacacaag | | | | 600 |
| gttttacttg gtctttgaga aattgcaagg aggttccatc ttagcccaca tccagaagca | | | | 660 |
| aaagcacttc aatgagcgag aagccagccg agtggtgcgg gacgttgctg ctgcccttga | | | | 720 |
| cttcctgcat accaaagaca agtctctct ctgtcaccta ggctggagtg ctatggcgcc | | | | 780 |
| atcagggctc actgcagccc aacctccct gggctccagt gatcctccca cctcagcctc | | | | 840 |
| ccaagtagct gggactacag gcattgctca tcgtgatctg aaaccagaaa atatattgtg | | | | 900 |
| tgaatctcca gaaaaggtgt ctccagtgaa aatctgtgac tttgacttgg gcagtgggat | | | | 960 |
| gaaactgaac aactcctgta cccccataac acaccagag ctgaccaccc catgtggctc | | | | 1020 |
| tgcagaatac atggccctg aggtagtgga ggtcttcacg gaccaggcca cattctacga | | | | 1080 |
| caagcgctgt gacctgtgga gcctgggcgt ggtcctctac atcatgctga gtggctaccc | | | | 1140 |
| acccttcgtg ggtcactgcg gggccgactg tggctgggac cggggcgagg tctgcagggt | | | | 1200 |
| gtgccagaac aagctgtttg aaagcatcca ggaaggcaag tatgagtttc ctgacaagga | | | | 1260 |
| ctgggcacac atctccagtg aagccaaaga cctcatctcc aagctcctgg tgcgagatgc | | | | 1320 |

```
aaagcagaga cttagcgccg cccaagttct gcagcaccca tgggtgcagg ggcaagctcc    1380
agaaaaggga ctccccacgc cgcaagtcct ccagaggaac agcagcacaa tggacctgac    1440
gctcttcgca gctgaggcca tcgcccttaa ccgccagcta tctcagcacg aagagaacga    1500
actagcagag gagccagagg cactagctga tggcctctgc tccatgaagc tttcccctcc    1560
ctgcaagtca cgcctggccc ggagacgggc cctggcccag gcaggccgtg gtgaagacag    1620
gagcccgccc acagcactct gaaatgctcc agtcacacct tataggccct aggcctggcc    1680
aggcattgtc ccctggaaac ctgtgtggct aaagtctgct gagcaggcag cagcctctgc    1740
tctgtggctc cattcaggct ttttcatcta cgaaggccct gaggttccca tcaaccccca    1800
tttccctagg gtcctggagg aaaaagcttt tccaaaggg gttgtctttg aaaaggaaag     1860
caatcacttc tcactttgca taattgcctg cagcaggaac atctcttcac tgggctccac    1920
ctgctcaccc gcctgcagat ctgggatcca gcctgctctc accgctgtag ctgtggcggc    1980
tggggctgca gcctgcaggg agaagcaaga agcatcagtt gacagaggct gccgacacgt    2040
gcctcttccc tctcttctct gtcaccctcc tctggcggtc cttccacctt cctctgtcct    2100
ccggatgtcc tctttgcccg tcttctccct tggctgagca aagccatccc ctcaattcag    2160
ggaagggcaa ggagccttcc tcattcagga aatcaaatca gtcttccggt ctgcagcacg    2220
gaaaagcaca taatctttct ttgctgtgac tgaaatgtat ccctcgttta tcatcccctt    2280
tgtttgtgat tgctgctaaa gtcagtagta tcgttttttt aaaaaaaaag tttggtgttt    2340
ttaaccatgc tgttccagca aagatgatac cttaaactcc cactgcaagc ccatgaactt    2400
cccagagagt ggaacggctt gctcttcttt ctagaatgtc catgcacttg ggttttaatc    2460
agcagttccc tattattctg attttaagct gttcctgtga tgaacttaga gacagcatcg    2520
gtgtctgctg ctgtgtcccc aggtcttgtg tgggtggcac agatctgggc agttagatag    2580
tgctctgtgc ctaaggtgaa gccacactag ggtgaagcct cacttccctg tttgagcaat    2640
gcagtgcctg ctgcccgtgt gcatgaaggt acagccattc agataagtgg aactattgag    2700
ttacataaag aaaatagatt tgcatttgtc aggcagacgt ttatacaaca ccacggtgct    2760
tttatacatt gtgcttattt taataaaact gaaattctat gtgtggccta aaaaaaaaaa    2820
aaaaaaa                                                              2827
```